US010828368B2

(12) United States Patent
Gulati

(10) Patent No.: US 10,828,368 B2
(45) Date of Patent: Nov. 10, 2020

(54) THERAPEUTIC TREATMENTS USING CENTHAQUIN

(71) Applicant: MIDWESTERN UNIVERSITY, Downers Grove, IL (US)

(72) Inventor: Anil Gulati, Naperville, IL (US)

(73) Assignee: MIDWESTERN UNIVERSITY, Downers Grove, IL (US)

( * ) Notice: Subject to any disclaimer, the term of this patent is extended or adjusted under 35 U.S.C. 154(b) by 0 days.

(21) Appl. No.: 15/714,008

(22) Filed: Sep. 25, 2017

(65) Prior Publication Data

US 2018/0085461 A1 Mar. 29, 2018

Related U.S. Application Data

(63) Continuation of application No. 13/266,205, filed as application No. PCT/US2010/032942 on Apr. 29, 2010, now abandoned.

(60) Provisional application No. 61/174,257, filed on Apr. 30, 2009.

(51) Int. Cl.
| A61K 31/496 | (2006.01) |
| A61K 45/06 | (2006.01) |
| A61K 31/4025 | (2006.01) |
| A61K 31/42 | (2006.01) |
| A61K 31/506 | (2006.01) |

(52) U.S. Cl.
CPC .......... *A61K 45/06* (2013.01); *A61K 31/4025* (2013.01); *A61K 31/42* (2013.01); *A61K 31/506* (2013.01); *A61K 2300/00* (2013.01)

(58) Field of Classification Search
CPC .................................................. A61K 31/496
USPC ..................................................... 514/253.01
See application file for complete search history.

(56) References Cited

U.S. PATENT DOCUMENTS

| 3,954,987 | A | 5/1976 | Simpson |
| 3,983,121 | A | 9/1976 | Murthi et al. |
| 4,088,659 | A | 5/1978 | Bhati et al. |
| 4,761,417 | A | 8/1988 | Maroko |
| 5,055,470 | A | 10/1991 | Boissard et al. |
| 5,922,681 | A | 7/1999 | Doherty et al. |
| 6,369,114 | B1 | 4/2002 | Weil et al. |
| 6,372,226 | B2 | 4/2002 | Aoki et al. |
| 6,545,048 | B1 | 4/2003 | Patterson et al. |
| 7,030,082 | B2 | 4/2006 | Soltero et al. |
| 8,623,823 | B2 | 1/2014 | Gulati |
| 8,980,874 | B2 | 3/2015 | Gulati |
| 9,493,524 | B2 | 11/2016 | Gulati |
| 10,112,981 | B2 | 10/2018 | Gulati |
| 10,561,704 | B2 | 2/2020 | Gulati |
| 2002/0082285 | A1 | 6/2002 | Lebwohl |
| 2003/0100507 | A1 | 5/2003 | Gulati |
| 2003/0104976 | A1 | 6/2003 | Davar et al. |
| 2003/0232787 | A1 | 12/2003 | Dooley |
| 2003/0236235 | A1 | 12/2003 | Gulati |
| 2004/0044008 | A1 | 3/2004 | Daugan et al. |
| 2004/0063719 | A1 | 4/2004 | Adams et al. |
| 2004/0138121 | A1 | 7/2004 | Gulati |
| 2004/0176274 | A1 | 9/2004 | Davar et al. |
| 2006/0079553 | A1 | 4/2006 | Hargreaves et al. |
| 2007/0066568 | A1 | 3/2007 | Dalton et al. |
| 2010/0004166 | A1 | 1/2010 | Pittner et al. |
| 2010/0189802 | A1 | 7/2010 | Childs et al. |
| 2010/0209433 | A1 | 8/2010 | Bergmann et al. |
| 2011/0312936 | A1 | 12/2011 | Lanter et al. |
| 2012/0083447 | A1 | 4/2012 | Gulati |
| 2012/0093798 | A1 | 4/2012 | Gulati |
| 2012/0308644 | A1 | 12/2012 | Bromley et al. |
| 2015/0250782 | A1 | 9/2015 | Gulati et al. |
| 2016/0151450 | A1 | 6/2016 | Gulati |

FOREIGN PATENT DOCUMENTS

| CN | 102458399 A | 5/2012 |
| DE | 2421382 A1 | 11/1975 |
| EP | 0410114 A2 | 1/1991 |
| EP | 2890376 A1 | 7/2015 |
| JP | 1975149692 | 11/1975 |
| JP | 1985-006612 | 1/1985 |
| JP | 2010-536868 A | 12/2010 |
| JP | 2012502952 A | 2/2012 |
| WO | WO-2002/43654 A2 | 6/2002 |
| WO | WO-03/009805 A2 | 2/2003 |
| WO | WO-2004/037235 A2 | 5/2004 |
| WO | WO-2004/045592 A2 | 6/2004 |
| WO | WO-2008/043102 A2 | 4/2008 |
| WO | WO-2009/026282 A2 | 2/2009 |
| WO | WO-2009/026828 A1 | 3/2009 |
| WO | WO-2010/127096 A2 | 11/2010 |
| WO | WO-2010/127197 A2 | 11/2010 |
| WO | WO-2012/138043 A2 | 10/2012 |
| WO | WO-2014/035446 A1 | 3/2014 |
| WO | WO-2019/213558 A1 | 11/2019 |

OTHER PUBLICATIONS

Abo-Zena et al., "Hypertensive Urgency Induced by an Interaction of Mirtazapine and Clinidine," Pharmacotherapy 20:476-478 (2000).
Arya, "Centhaquin," Drugs of the Future 9(2):104-105 (1984).
Backo et al., "Clonidine-Induced Hypertension in a Patient with a Spinal Lesion," Ann Pharmacother 36:1396-1398 (2002).
Bajpai et al., "Fourier transform infrared spectra and normal mode analysis of 1-(3-methyl phenyl piperazin-1-yl)-2-(quinolin-2-ypethane (Centhaquin): a potent centrally acting anti-hypertensive agent," J. Molecular Structure 516:15-21 (2000).
Bennett, "The LANSS Pain Scale: the Leeds assessment of neuropathic symptoms and signs," Pain. 92:147-157 (2001).
Bertolini et al., "The Adrenocorticotropic Hormone (ACTH)—Induced Reversal of Hemorrhagic Shock," Resuscitation 18(2-3):253-267 (1989).

(Continued)

*Primary Examiner* — Raymond J Henley, III
(74) *Attorney, Agent, or Firm* — Marshall, Gerstein & Borun LLP

(57) ABSTRACT

Methods of treating hypertension, pain, and resuscitative hemorrhagic shock using an adrenergic agent, like centhaquin, are disclosed. The methods treat mammals, including humans.

10 Claims, 17 Drawing Sheets

(56) References Cited

OTHER PUBLICATIONS

Bhatnagar et al., "Effect of Centhaquine on Spontaneous and Evoked Norepinephrine Release from Isolated Perfused Rabbit Heart," Drug Res. 35(I):693-697 (1985).
Bousquet et al., "Pharmacological Tools for the Study of the Central Vasomotor Control," Biochem Pharmacol 32:1459-1465 (1983).
Brondani et al., "Levels of vascular cell adhesion molecule-1 and endothelin-1 in ischemic stroke: A longitudinal prospective study," Clin Biochem 40:282-284 (2007).
Carlsson, "Assessment of Chronic Pain. I. Aspects of the Reliability and Validity of the Visual Analogue Scale," Pain 16:87-101 (1983).
Carpy et al., "Structure of 1-(3-Methylphenyl)-4-(2-β-quinolylethyl)piperazone: Centhaquin," Acta Crystallographica C47:227-229 (1991).
Carrier et al., "Enhancement of Alpha-1 and Alpha-2 Adrenerigic Agonist-Induced Vasoconstriction by Removal of Endothelium in Rat Aorta," J Pharmacol Exp Ther 232:682-687 (1985).
Chan et al., "Effects of endothelin-1 on portal-systemic collaterals of common bile duct-ligated cirrhotic rats," European Journal of Clinical Investigation 34(4):290-296 (2004).
Charu et al., "Inhaled corticosteroids and long term outcome in adults with asthma," Thorax 61:1011-1012 (2006).
Chen et al., "Physical Conditioning Decreases Norepinephrine-Induced Vasoconstriction in Rabbits—Possible Roles of Norepinephrine-Evoked Endothelium-Derived Relaxing Factor," Circulation 90:970-975 (1994).
Consigny, "Endothelin-1 increases arterial sensitivity to 5-hydroxytryptamine," Eur J Pharmacol 186:239-245 (1990).
Cowburn et al., "Selective or non-selective endothelin receptor antagonists for chronic heart failure: what do we know so far?", Journal of Clinical and Basic Cardiology 2(1):41-44 (1999).
D'Angelo et al., "In vivo evidence for endothelin-1-mediated attenuation of $\alpha_1$-adrenergic stimulation," Am J Physiol Heart Circ Physiol 290:H1251-1258 (2006).
Dillon et al., "A bioassay of Treatment of Hemorrhagic Shock," Archives of Surgery, 93(4):537-555, plus abstract (1966).
Fagura et al., "Pharmacological classification of $\alpha1$-adrenoceptors mediating contractions of rabbit isolated ear artery: comparison with rat isolated thoracic aorta," Br J Pharmacol 120:247-258 (1997).
Gondre et al., "Endothelin-1-Induced Alterations in Phenylephrine-Induced Contractile Responses are Largely Additive in Physiologically Diverse Rabbit Vasculature," J Pharmacol Exp Ther 286:635-642 (1998).
Gulati et al., "Central Serotonergic Uptake Mechanisms in Hypertensive Rats: Effects of Clonidine and Centhaquin," European Journal of Pharmacology 231(2):151-156 (1993).
Gulati et al., "Effect of Repeated Administration of Centhaquin, a Centrally Acting Hypotensive Drug, on Adrenergic, Cholinergic (Muscarinic), Dopaminergic, and Serotonergic Receptors in Brain Regions of Rat," Drug Development Research 23:307-323 (1991).
Gulati et al., "Effect of Repeated Administration of Clonidine on Adrenergic, Cholinergic (Muscarinic), Dopaminergic, and Serotonergic Receptors in Brain Regions of Rats," Drug Development Research 22:141-152 (1991).
Gulati et al., "Endothelin antagonizes the hypotension and potentiates the hypertension induced by clonidine," Eur J Pharmacol 230:293-300 (1993).
Gulati et al., "Role of sympathetic nervous system in cardiovascular effects of centrally administered endothelin-1 in rats," Am J Physiol 273:H1177-1186 (1997).
Gulati, "Evidence for Antagonistic Activity of Endothelin for Clonidine Induced Hypotension and bradycardia," Life Sci 50:153-160 (1992).
Gulati, et al. "Effect of centrally administered endothelin agonists on systemic and regional blood circulation in the rat: role of sympathetic nervous system," Neuropeptides 31:301-309 (1997).
Gulati, et al., "Cardiovascular effects of centrally administered endothelin-1 in rats," Journal of cardiovascular pharmacology 26 Suppl 3:S244-246 (1995).
Guyenet et al. "Inhibition of Sympathetic Preganglionic Neurons by Catecholamines and Clonidine: Mediation by an $\alpha$-Adrenergic Receptor," J Neurosci 1:908-917 (1981).
Hegde et al., "Attenuation in Rat Brain Nitric Oxide Synthase Activity in the Coarctation Model of Hypertension," Pharmacol Res 36:109-114 (1997).
Hickey et al., "Characterization of a coronary vasoconstrictor produced by cultured endothelial cells," Am J Physiol 248:C550-556 (1985).
Hunyor et al., "Clonidine overdose," Br Med J 4:23 (1975).
Ikeda et al., "A New Endothelin Receptor Antagonist, TAK-044, Shows Long-Lasting Inhibition of Both $ET_A$- and $ET_B$-Mediated Blood Pressure Responses in Rats," J Pharmacol Exp Ther 270:728-733 (1994).
International Search Report in international application No. PCT/US2010/032942, dated Jan. 24, 2011.
Ishikawa et al., "Biochemical and pharmacological profile of a potent and selective endothelin B-receptor antagonist, BQ-788," Proc Natl Acad Sci USA 91(11):4892-4896 (1994).
Jarajapu et al. "The $_{\alpha1A}$-adrenoceptor subtype mediates contraction in rat femoral resistance arteries," Eur J Pharmacol 422:127-135 (2001).
Kennedy et al., "Centrally Acting Imidazolines Stimulate Vascular Alpha 1A-Adrenergic Receptors in Rat-Tail Artery," Cell Mol Neurobiol 26:645-657 (2006).
Kobinger et al. "Kreislaufuntersuchungen mit 2-(2,6-Dichlorphenylamino)-2-imidazolin-hydrochlorid," Arzneimittelforschung 17:292-300 (1967).
Kobinger, "Central $\alpha$-Adrenergic Systems as Targets for Hypotensive Drugs," Rev Physiol Biochem Pharmacol 81:39-100 (1978).
Kuwaki et al., "Modulatory Effects of Rat Endothelin on Central Cardiovascular Control in Rats," Jpn J Physiol 40:97-116 (1990).
Langer et al, "Recent Developments in Noradrenergic Neurotransmission and its Relevance to the Mechanism of Action of Certain Antihypertensive Agents," Hypertension 2:372-382 (1980).
Lowry et al., "Protein Measurement with the Folin Phenol Reagent," J Biol Chem 193:265-275 (1951).
Meller et al., "The Possible Role of Flia in Nociceptive Processing and Hyperalgesia in the Spinal Cord of the Rat," Neuropharmacol. 33:1471-8 (1994).
Murti et al., Synthesis and Osar of 1-aryl-4-(β-2-quinolyl/1-isoquinolylethyl)piperazines and some related compounds as hypotensive agents' Indian Journal of Chemistry 28B:934-942 (1989).
Naftchi et al., "Autonomic Dysreflexia: Pharmacological Management of Hypertensive Crises in Spinal Cord Injured Patients," J Spinal Cord Med 20:355-360 (1997).
Nakayama et al., "Potentiation by endothelin-1 of 5-hydroxytryptamine-induced contraction in coronary artery of the pig," Br J Pharmacol 104:978-986 (1991).
Nowicki et al., "Endothelin-1 in Human Intestine Resected for Necrotizing Enterocolitis," J Pediatr 146:805-810 (2005).
Ouchi et al., "Central effect of endothelin on blood pressure in conscious rats," Am J Physiol 256:H1747-H1751 (1989).
Pacher et al., "Measurement of cardiac function using pressure-volume conductance catheter technique in mice and rats," Nat Protoc 3:1422-1434 (2008).
Pai et al., "Clonidine Poisoning," Pediatrics 58:749-750 (1976).
Radovits et al., "Endothelial dysfunction after hypoxia-reoxygenation: Do in vitro models work," Vascul Pharmacol 51:37-43 (2009).
Rebello et al., "Systemic hemodynamic and regional circulatory effects of centrally administered endothelin-1 are mediated through $ET_A$ receptors," Brain Research 676:141-150 (1995).
Sakamoto et al., "Distinct Subdomains of Human Endothelin Receptors Determine Their Selectivity to Endothelin$_A$-selective Antagonist and Endothelins-selective Agonists," J Biol Chem 268:8547-8553 (1993).
Schmitt et al., "Localization of the Hypotensive Effect of 2-(2-6-Dichlorophenylamino)-2-Imidazoline Hydrochloride (St 155, Catapresan)," Eur J Pharmacol 6:8-12 (1969).
Shetty et al. Biochem Biophys Res Commun 191:459-464 (1993).

(56) References Cited

OTHER PUBLICATIONS

Souza et al., "Increased Cardiac Sympathetic Drive and Reduced Vagal Modulation Following Endothelin Receptor Antagonism in Healthy Conscious Rats," Clin Exp Pharmacol Physiol 35:751-756 (2008).
Srimal et al., "Pharmacological studies on 2-(2-(4-(3-methylphenyl)-1-Piperazinyl)Ethyl) Quinoline (Centhaquin). I. Hypotensive Activity," Journal of the Italian Pharmac Pharmacol Res 22:319-329 (1990).
Stein et al, "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," J Med Chem 37:329-331 (1994).
Supplementary European Search Report in counterpart foreign Application No. EP10770318, dated Oct. 23, 2012.
Tabuchi et al., "Endothelin Inhibits Presynaptic Adrenergic Neurotransmission in Rat Mesenteric Artery," Biochem Biophys Res Commun 161:803-808 (1989).
Timmermans et al., "Postsynaptic $a_1$- and $a_2$-Adrenoceptors in the Circulatory System of the Pithed Rat: Selective Stimulation of the $a_2$-Type by B-HT 933," Eur J Pharmacol 63:199-202 (1980).
Troncoso et al., "Hypertensive Urgency with Clonidine and Mirtazepine," Psychosomatics 45:449-450 (2004).
U'Prichard et al., "Binding Characteristics of a Radiolabeled Agonist and Antagonist at Central Nervous System Alpha Noradrenergic Receptors," Mol Pharmacol 13:454-473 (1977).
Van Zwieten et al., "The Hypotensive Activity and Side Effects of Methyldopa, Clonidine, and Guanfacine," Hypertension 6:1128-33 (1984).
Vazquez-Prado et al., "Activation of Endothelin ETA Receptors Induces Phosphorylation of $\alpha_{1b}$-Adrenoreceptors in Rat-1 Fibroblasts," J Biot Chem 272:27330-27337 (1997).
Watts, "5-Hydroxytryptamine-Induced Potentiation of Endothelin-1- and Norepinephrine-lnduced Contraction Is Mitogen-Activated Protein Kinase Pathway Dependent," Hypertension 35:244-248 (2000).
Watts, "The love of a lifetime: 5-HT in the cardiovascular system," Am J Physiol Regul lntegr Comp Physiol $252-R256 (2009).
Wiklund et al., "Inhibition of adrenergic neuroeffector transmission by endothelin in the guinea-pig femoral artery," Acta Physiol Scand 134:311-312 (1988).
Williamson et al., "Pain: a review of three commonly used pain rating scales," J. Clin Nurs. 14:798-804 (2005).
Wu et al., "Recent discovery and development of endothelin receptor antagonists," Exp. Opin. Ther. Patents 10(11):1653-1668 (2000).
Yanagisawa et al., "A Novel potent vasoconstrictor peptide produced by vascular endothelial cells," Nature 332:411-415 (1988).
Ahmed, et al. "Curcuminoids Enhance Memory in an Amyloid-Infused Rat Model of Alzheimer's Disease," Neuroscience 169:1296-1306 (2010).
Andres et al. "Human neural stem cells enhance structural plasticity and axonal transport in the ischaemic brain," Brain 134:1777-1789 (2011).
Area-Gomez et al., "Mitochondria-associated ER membranes and Alzheimer Disease," Curr Opin Genet Dev. 38:90-96 (2016).
Asano, et al. "Endothelin: a potential modulator of cerebral vasospasm," European journal of pharmacology 190:365-372 (1990).
Bacigaluppi et al., "Delayed post-ischaemic neuroprotection following systemic neural stem cell transplantation involves multiple mechanisms," Brain : a journal of neurology 132:2239-2251 (2009).
Baquer, et al. "A metabolic and functional overview of brain aging linked to neurological disorders," Biogerontology 10:377-413 (2009).
Barone, et al. "Selective antagonism of endothelin-A-receptors improves outcome in both head trauma and focal stroke in rat," Journal of cardiovascular pharmacology 36:S357-361 (2000).
Barone, et al. "The endothelin receptor antagonist SB 217242 reduces cerebral focal ischemic brain injury," Journal of cardiovascular pharmacology 26 Suppl 3:S404-407 (1995).
Bath, et al. "ABC of arterial and venous disease, Acute stroke," BMJ 320:920-923 (2000).

Bell et al., Effect of endothelin-1 and sarafotoxin S6c on blood flow in a rat tumor, J. Cardiovasc. Pharmacol., 26(Suppl. 3):5222-5 (1995).
Bell et al., Modification of blood flow in the HSN tumour and normal tissues of the rat by the endothelin ETb receptor agonist, IRL 1620, Int. J. Cancer, 80:295-302 (1999).
Bell, et al. "Neurovascular mechanisms and blood-brain barrier disorder in Alzheimer's disease," Acta neuropathologica 118:103-113 (2009).
Bomber et al., Propranolol hydrochloride enhancement of tumor perfusion and uptake of gallium-67 in a mouse sarcoma, J. Nucl. Med., 27(2):243-5 (1986).
Bonvallet et al., "BQ123, an $ET_A$-receptor antagonist, attenuates hypoxic pulmonary hyertension in rats," Am J Physiol 266:H1327-1331 (1994).
Bork, "Powers and Pitfalls in Sequence Analysis: The 70% Hurdle," Genome Res. 10(4):398-400 (2000).
Brasch et al., Assessing tumor angiogenesis using macromolecular MR imaging contrast media, JMRI, 7:68-74 (1997).
Bredesen, et al. "Cell death in the nervous system," Nature 443:796-802 (2006).
Breier, et al. "The role of vascular endothelial growth factor in blood vessel formation," Trends in cell biology 6:454-456 (1996).
Brenner, "Errors in genome annotation," Trends in Genetics, 15(4):132-3 (1999).
Briyal et al., "IRL-1620 prevents beta amyloid (Aβ) induced oxidative stress and cognitive impairment," Journal of Clinical PHarmacology 51(9):1349, Abstract No. 1123022 (2011).
Briyal, et al. "Effect of combination of endothelin receptor antagonist (TAK-044) and aspirin in middle cerebral artery occlusion model of acute ischemic stroke in rats," Methods Find Exp Clin Pharmacol 29:257-263 (2007).
Briyal, et al. "Endothelin-A receptor antagonist BQ123 potentiates acetaminophen induced hypothermia and reduces infarction following focal cerebral ischemia in rats," European journal of pharmacology 644:73-79 (2010).
Briyal, et al. "Endothelin-A receptor antagonists prevent amyloid-beta-induced increase in ETA receptor expression, oxidative stress, and cognitive impairment," Journal of Alzheimer's disease : JAD 23:491-503 (2011).
Briyal, et al. "Repeated administration of centhaquin to pregnant rats did not affect postnatal development and expression of endothelin receptors in the brain, heart or kidney of pups," Arzneimittel-Forschung 62:670-676 (2012b).
Briyal, et al. "Repeated administration of exendin-4 reduces focal cerebral ischemia-induced infarction in rats," Brain research 1427:23-34 (2012a).
Brooks et al., Identification and function of putative ETB receptor subtypes in the dog kidney, J. Cardiovasc. Pharmacol., 26(Suppl 3):S322-5 (1995).
Cali et al., "Enhanced parkin levels favor ER-mitochondria crosstalk and guarantee $Ca^{2+}$ transfer to sustain cell bioenergetics," Biochimica et Biophysica Acta 1832:495-508 (2013).
Carmichael, "Cellular and molecular mechanisms of neural repair after stroke: making waves," Annals of neurology 59:735-742 (2006).
Casadesus, et al. "Indices of metabolic dysfunction and oxidative stress," Neurochemical research 32:717-722 (2007).
Chakrabarti et al., "Therapeutic potential of endothelin receptor antagonists in diabetes," Expert Opinion on Investigational Drugs 9(12):2873-2888 (2000).
Chen, et al. "Niaspan increases angiogenesis and improves functional recovery after stroke," Annals of neurology 62:49-58 (2007).
Chuquet, et al. "Selective blockade of endothelin-B receptors exacerbates ischemic brain damage in the rat," Stroke; a journal of cerebral circulation 33:3019-3025 (2002).
Cirrito, et al. "Synaptic activity regulates interstitial fluid amyloid-beta levels in vivo," Neuron 48:913-922 (2005).
Cuervo, "Autophagy: In Sickness and in Health," Trends Cell Biol 14:70-77 (2004).
Cutler, et al. "Involvement of oxidative stress-induced abnormalities in ceramide and cholesterol metabolism in brain aging and

(56) References Cited

OTHER PUBLICATIONS

Alzheimer's disease," Proceedings of the National Academy of Sciences of the United States of America 101:2070-2075 (2004).
De la Torre, "Impaired brain microcirculation may trigger Alzheimer's disease," Neuroscience and biobehavioral reviews 18:397-401 (1994).
De la Torre, et al. "Hippocampal nitric oxide upregulation precedes memory loss and A beta 1-40 accumulation after chronic brain hypoperfusion in rats," Neurological research 25:635-641 (2003).
Deb, et al. "Pathophysiologic mechanisms of acute ischemic stroke: An overview with emphasis on therapeutic significance beyond thrombolysis," Pathophysiology 17:197-218 (2010).
Dembowski, et al. "Phenotype, intestinal morphology, and survival of homozygous and heterozygous endothelin B receptor—deficient (spotting lethal) rats," *J Pediatr Surg* 35:480-488 (2000).
Dimyan, et al. "Neuroplasticity in the context of motor rehabilitation after stroke," Nature reviews Neurology 7:76-85 (2011).
Ding, et al. "Magnetic resonance imaging investigation of axonal remodeling and angiogenesis after embolic stroke in sildenafil-treated rats," Journal of Cerebral Blood Flow and Metabolism, 28:1440-1448 (2008).
Doerks et al., Protein annotation: detective work for function prediction, Trends Genet., 14(6):248-50 (1998).
Donnan, et al. "Stroke," Lancet 371:1612-1623 (2008).
Ehrenreich, "The astrocytic endothelin system: toward solving a mystery focus on distinct pharmacological properties of ET-1 and ET-3 on astroglial gap junctions and Ca(2+) signaling" The American journal of physiology 277:C614-615 (1999).
Ehrenreich, et al. "Endothelin b receptor deficiency is associated with an increased rate of neuronal apoptosis in the dentate gyrus," Neuroscience 95:993-1001 (2000).
Ehrenreich, et al. "Endothelin B receptor-deficient rats as a subtraction model to study the cerebral endothelin system," Neuroscience 91:1067-1075 (1999).
Ellman, "Tissue sulfhydryl groups," Archives of biochemistry and biophysics 82:70-77 (1959).
Ethell, "An amyloid-notch hypothesis for Alzheimer's disease," The Neuroscientist 16:614-617 (2010).
Feigin, et al. "Worldwide stroke incidence and early case fatality reported in 56 population-based studies: a systematic review," Lancet Neurol 8:355-369 (2009).
Fisher, et al., The International Agenda for Stroke, in 1st Global Conference on Healthy Lifestyles and Noncommunicable Diseases Control (Association AH ed), American Heart Association, Moscow (2011).
Font, et al., "Angiogenesis, neurogenesis and neuroplasticity in ischemic stroke," Current cardiology reviews 6:238-244 (2010).
Gil-Mohapel, et al., "Hippocampal cell loss and neurogenesis after fetal alcohol exposure: insights from different rodent models," Brain Res Rev 64:283-303 (2010).
Goligorsky, et al. "Co-operation between endothelin and nitric oxide in promoting endothelial cell migration and angiogenesis," Clinical and experimental pharmacology & physiology 26:269-271 (1999).
Gora-Kupilas, et al., "The neuroprotective function of vascular endothelial growth factor (VEGF)," Folia neuropathologica / Association of Polish Neuropathologists and Medical Research Centre, Polish Academy of Sciences 43:31-39 (2005).
Goto, et al., "Endothelin activates the dihydropyridine-sensitive, voltage-dependent Ca2+ channel in vascular smooth muscle," Proceedings of the National Academy of Sciences of the United States of America 86:3915-3918 (1989).
Graf et al., Determination of optimal time window for liver scanning with CT during arterial portography, Radiology, 190:43-7 (1994).
Gulati, et al. "Cardiovascular effects of centrally administered endothelin-1 and its relationship to changes in cerebral blood flow," Life sciences 58:437-445 (1996).
Gupta, et al. "Effect of endothelin antagonist (TAK-044) on cerebral ischemic volume, oxidative stress markers and neurobehavioral parameters in the middle cerebral artery occlusion model of stroke in rats," Life sciences 77:15-27 (2005).
Han, et al., "Cerebrovascular dysfunction in amyloid precursor protein transgenic mice: contribution of soluble and insoluble amyloid-beta peptide, partial restoration via gamma-secretase inhibition," The Journal of neuroscience : the official journal of the Society for Neuroscience 28:13542-13550 (2008).
Hara et al., "Suppression of Basal Autophagy in Neural Cells Causes Neurodegenerative Disease in Mice," Nature 441:885-889 (2006).
Hardy, et al. "The amyloid hypothesis of Alzheimer's disease: progress and problems on the road to therapeutics," Science 297:353-356 (2002).
Harvey et al., Imaging of tumour therapy responses by dynamic CT, Eur. J. Radiology, 30:221-6 (1999).
Hawkins, et al. "The blood-brain barrier/neurovascular unit in health and disease," Pharmacological reviews 57:173-185 (2005).
Hensley, et al., "A model for beta-amyloid aggregation and neurotoxicity based on free radical generation by the peptide: relevance to Alzheimer disease," Proceedings of the National Academy of Sciences of the United States of America 91:3270-3274 (1994).
Hermann, et al., "Implications of vascular endothelial growth factor for postischemic neurovascular remodeling," Journal of cerebral blood flow and metabolism : official journal of the International Society of Cerebral Blood Flow and Metabolism 29:1620-1643 (2009).
Hoehn, et al. "VEGF mRNA expressed in microvessels of neonatal and adult rat cerebral cortex," Brain Res Mol Brain Res 101:103-108 (2002).
Iadecola, et al. "Threats to the mind: aging, amyloid, and hypertension," Stroke; a journal of cerebral circulation 40:S40-44 (2009).
International preliminary report on patentability from PCT/US2014/045748 dated Jan. 12, 2016.
International search report from PCT/US2014/045748 dated Nov. 13, 2014.
International Search Report in international application No. PCT/US2008/073581, dated Jul. 15, 2009.
International Search Report in international application No. PCT/US2010/033083, dated Jan. 25, 2011.
Ishizuka et al., Endothelin-1 enhances vascular cell adhesion molecule-1 expression in tumor necrosis factor alpha-stimulated vascular endothelial cells, Eur. J. Pharmacol., 369(2):237-45 (1999).
Janson, et al., "Increased risk of type 2 diabetes in Alzheimer disease," Diabetes 53:474-481 (2004).
Johnson, et al., "Cognitive profiles in dementia: Alzheimer disease vs healthy brain aging," Neurology 71:1783-1789 (2008).
Kakkar, et al., "A modified spectrophotometric assay of superoxide dismutase," Indian journal of biochemistry & biophysics 21:130-132 (1984).
Katayama, Current trends in the treatment of acute ischemic stroke, Nichiidaishi, 65(3):4-9 (1999).
Kaundal, et al., "Targeting endothelin receptors for pharmacotherapy of ischemic stroke: current scenario and future perspectives," Drug Discov Today 17:793-804 (2012).
Kitazono, et al., "Enhanced responses of the basilar artery to activation of endothelin-B receptors in stroke-prone spontaneously hypertensive rats," Hypertension 25:490-494 (1995).
Kohzuki, et al., "Endothelin receptors in ischemic rat brain and Alzheimer brain," Journal of cardiovascular pharmacology 26 Suppl 3:S329-331 (1995).
Kojima, et al. Circulating levels of endothelin and atrial natriuretic factor during postnatal life' Acta Paediatr 81:676-677 (1992).
Kopito et al., "Conformational Disease," Nat Cell Biol 2:E207-209 (2000).
Koyama, et al. "I.c.v administration of an endothelin ET(B) receptor agonist stimulates vascular endothelial growth factor-A production and activates vascular endothelial growth factor receptors in rat brain," Neuroscience 192:689-698 (2011).
Koyama, et al., "Endothelins reciprocally regulate VEGF-A and angiopoietin-1 production in cultured rat astrocytes: implications on astrocytic proliferation," Glia 60:1954-1963 (2012).
Laziz I, et al. "Endothelin as a neuroprotective factor in the olfactory epithelium," Neuroscience 172:20-29 (2011).

(56) References Cited

OTHER PUBLICATIONS

Lee, et al., "The endothelin receptor-B is required for the migration of neural crest-derived melanocyte and enteric neuron precursors," Dev Biol 259:162-175 (2003).
Leonard, et al., "Endothelin B receptor agonist, IRL-1620, enhances angiogenesis and neurogenesis following cerebral ischemia in rats," Brain research 1528:28-41 (2013).
Leonard, et al., "Endothelin B receptor agonist, IRL-1620, provides long-term neuroprotection in cerebral ischemia in rats," Brain research 1464:14-23 (2012).
Leonard, et al., "Endothelin B receptor agonist, IRL-1620, reduces neurological damage following permanent middle cerebral artery occlusion in rats," Brain research 1420:48-58 (2011).
Leonard, et al., "Repeated administration of ET(B) receptor agonist, IRL-1620, produces tachyphylaxis only to its hypotensive effect," Pharmacological research : the official journal of the Italian Pharmacological Society 60:402-410 (2009).
Levin, "Endothelins," The New England journal of medicine 333:356-363 (1995).
Li, et al., "The requirement of extracellular signal-related protein kinase pathway in the activation of hypoxia inducible factor 1 alpha in the developing rat brain after hypoxia-ischemia," Acta neuropathologica 115:297-303 (2008).
Liu, et al., "Contralesional axonal remodeling of the corticospinal system in adult rats after stroke and bone marrow stromal cell treatment," Stroke; a journal of cerebral circulation 39:2571-2577 (2008).
Loo, et al. "Cortical expression of endothelin receptor subtypes A and B following middle cerebral artery occlusion in rats," Neuroscience 112:993-1000 (2002).
Lopes, et al., "Neurodegeneration in an Abeta-induced model of Alzheimer's disease: the role of Cdk5," Aging cell 9:64-77 (2010).
Ly, et al. "Neuroprotection and thrombolysis: combination therapy in acute ischaemic stroke," Expert Opin Pharmacother 7:1571-1581 (2006).
Malik, et al., "Neurogenesis continues in the third trimester of pregnancy and is suppressed by premature birth," The Journal of neuroscience : the official journal of the Society for Neuroscience 33:411-423 (2013).
Mark, et al., "A role for 4-hydroxynonenal, an aldehydic product of lipid peroxidation, in disruption of ion homeostasis and neuronal death induced by amyloid beta-peptide," Journal of neurochemistry 68:255-264 (1997).
Mathers, et al., "Global and regional causes of death," Br Med Bull 92:7-32 (2009).
Matus et al., "Protein Folding Stress in Neurodegenerative Diseases: A Glimpse Into the ER," Curr Opin Cell Biol 23:239-252 (2011).
Meier-Ruge, et al. "Changes in brain glucose metabolism as a key to the pathogenesis of Alzheimer's disease," Gerontology 40:246-252 (1994).
Merkwirth et al., "Loss of Prohibitin Membrane Scaffolds Impairs Mitochondrial Architecture and Leads to Tau Hyperphosphorylation and Neurodegeneration," PLOS Genetics 8(11):e1003021, 13 pages (2012).
Micieli, et al., "Safety and efficacy of alteplase in the treatment of acute ischemic stroke," Vasc Health Risk Manag 5:397-409 (2009).
Minami, et al. "Endothelin-1-like immunoreactivity in cerebral cortex of Alzheimer-type dementia" Progress in neuropsychopharmacology & biological psychiatry 19:509-513 (1995).
Morris, "Developments of a water-maze procedure for studying spatial learning in the rat," Journal of neuroscience methods 11:47-60 (1984).
Murphy, "Plasticity during stroke recovery: from synapse to behaviour," Nature reviews Neuroscience 10:861-872 (2009).
Murray, et al., "Membrane-mediated amyloidogenesis and the promotion of oxidative lipid damage by amyloid beta proteins," The Journal of biological chemistry 282:9335-9345 (2007).
Murray, et al., "Promotion of oxidative lipid membrane damage by amyloid beta proteins," Biochemistry 44:12606-12613 (2005).
Muruganandham et al., Diltiazem enhances tumor blood flow: MRI study in a murine tumor, Int. J. Radiation Oncology Biol. Phys., 43(2):413-21 (1999).
Nassif et al., "Autopagy impairment: a crossroad between neurodegeneration and tauopathies," BMC Biology 10(78), 4 pages (2012).
Ngo et al., The Protein Folding Problem and Tertiary Structure Prediction, Chapter 14 in Computational Complexity Protein Structure Prediction and the Levinthal Paradox, pp. 492-495 (1995).
Nitta, et al. "B-Amyloid protein-induced Alzheimer's disease animal model," Neuroscience letters 170:63-66 (1994).
Niwa, et al. "Exogenous Aβ1-40 reproduces cerebrovascular alterations resulting from amyloid precursor protein overexpression in mice," Journal of cerebral blood flow and metabolism : official journal of the International Society of Cerebral Blood Flow and Metabolism 20:1659-1668 (2000).
Niwa, et al., "Aβ-peptides enhance vasoconstriction in cerebral circulation," American journal of physiology Heart and circulatory physiology 281:H2417-2424 (2001).
Niwa, et al., "Cerebrovascular autoregulation is profoundly impaired in mice overexpressing amyloid precursor protein," American journal of physiology Heart and circulatory physiology 283:H315-323 (2002).
Nowacka, et al., "Vascular endothelial growth factor (VEGF) and its role in the central nervous system: a new element in the neurotrophic hypothesis of antidepressant drug action," Neuropeptides 46:1-10 (2012).
Nunomura, et al., "Oxidative damage is the earliest event in Alzheimer disease," Journal of neuropathology and experimental neurology 60:759-767 (2001).
Nv et al., N-Suc-[Glu9, Ala11, 15]ET-1(8-21) increases blood perfusion and enhances paclitaxel delivery to the tumor, 96th Annual Meeting of the American Association for Cancer Research, Abstract 5741 (2005).
Ogunshola, et al. "Neuronal VEGF expression correlates with angiogenesis in postnatal developing rat brain," Brain research Developmental brain research 119:139-153 (2000).
Ohkawa, et al. "Assay for lipid peroxides in animal tissues by thiobarbituric acid reaction," Analytical biochemistry 95:351-358 (1979).
Pannen et al., "Role of Endothelins and Nitric Oxide in Hepatic Reperfusion Injury in the Rat," Hepatology, 27(3):755-764 (1998).
Paris, et al. "Nilvadipine antagonizes both Abeta vasoactivity in isolated arteries, and the reduced cerebral blood flow in APPsw transgenic mice," Brain research 999:53-61 (2004).
Patel et al., Endothelin receptor mediated constriction and dilatation in feline cerebral resistance arterioles in vivo, Eur. J. Pharmacol., 307:41-8 (1996).
Patel, et al., "Therapeutic potential of endothelin receptor antagonists in experimental stroke," Journal of cardiovascular pharmacology 26 Suppl 3:S412-415 (1995).
Phillips, "The challenge of gene therapy and DNA delivery," J. Pharm. Pharmacol., 53(9):1169-74 (2001).
Quinn, "Comparing rat's to human's age: how old is my rat in people years?" Nutrition 21:775-777 (2005).
Rai et al., Evidence for the involvement of ET(B) receptors in ET-1-induced changes in blood flow to the rat breast tumor, Cancer Chemother. Pharmacol., 51(1):21-8 (2003).
Rao et al., "Misfolded proteins, endoplasmic reticulum stress and neurodegeneration," Curr Opin Cell Biol. 16(6):653-662 (2004).
Rebello, et al. "Elevated levels of endothelin-1 following unilateral cerebral-ischemia in rats," Faseb Journal 9:A937-A (1995).
Recht et al., The sequencing of chemotherapy and radiation therapy after conservative surgery for early-stage breast cancer, NEJM, 334(21):1356-61 (1996).
Riechers, et al. "Endothelin B receptor deficient transgenic rescue rats: a rescue phenomenon in the brain," Neuroscience 124:719-723 (2004).
Roger, et al. "Heart disease and stroke statistics—2012 update: a report from the American Heart Association," Circulation 125:e2-e220 (2012).
Rosenstein, et al., "VEGF in the nervous system," Organogenesis 6:107-114 (2010).

(56) References Cited

OTHER PUBLICATIONS

Rubinsztein, "The roles of intracellular protein-degradation pathways in neurodegeneration," Nature 443:780-786 (2006).
Ruetten et al., "Effects of the endothelin receptor antagonist, SB 209670, on circulatory failure and organ injury in endotoxic shock in the anaesthetized rat," British Journal of Pharmacology, 118(1):198-204 (1996).
Sardanelli et al., Dynamic helical CT of breast tumors, J. Comp. Assisted Tomography, 22(3):398-407 (1998).
Schiffrin, et al. "Clinical significance of endothelin in cardiovascular disease," Curr Opin Cardiol 12:354-367 (1997).
Schinelli, "Pharmacology and physiopathology of the brain endothelin system: an overview," Curr Med Chem 13:627-638, (2006).
Schneider, et al, "Contrasting actions of endothelin ET(A) and ET(B) receptors in cardiovascular disease," Annu Rev Pharmacol Toxicol 47:731-759 (2007).
Search Report from European Application No. 14823205.1 dated Jan. 4, 2017.
Selkoe, "Folding Proteins in Fatal Ways," Nature 426:900-904 (2003).
Shin, et al., "Age-dependent cerebrovascular dysfunction in a transgenic mouse model of cerebral amyloid angiopathy," Brain : a journal of neurology 130:2310-2319 (2007).
Sims, et al., "Mitochondria, oxidative metabolism and cell death in stroke," Biochimica et biophysica acta pp. 80-91 (2009).
Skolnick et al., "From genes to protein structure and function: novel applications of computational approaches in the genomic era," Trends Biotechnol., 18(1):34-9 (2000).
Smith, et al. "Soluble beta-amyloid (A beta) 40 causes attenuation or potentiation of noradrenaline-induced vasoconstriction in rats depending upon the concentration employed," Neuroscience letters 367:129-132 (2004).
Smyth et al., Use of vasoactive agents to increase tumor perfusion and the antitumor efficacy of drug-monoclonal antibody conjugates, J. Natl. Cancer Inst., 79(6):1367-73 (1987).
Sonveaux et al., Endothelin-1 is a critical mediator of myogenic tone in tumor arterioles: implications for cancer treatment, Cancer Res., 64(9):3209-14 (2004).
Steinwachs, et al., "The future of cardiology: utilization and costs of care," J Am Coll Cardiol 35:91B-98B (2000).
Strong, et al. "Preventing stroke: saving lives around the world," Lancet Neurol 6:182-187 (2007).
Suo, et al. "Soluble Alzheimers beta-amyloid constricts the cerebral vasculature in vivo," Neuroscience letters 257:77-80 (1998).
Takagawa et al., Efficacy of the drugs administered to the patients with cerebral vascular diseases from a viewpoint of cerebral blood flow measurement, 48(9):667-93 (1994).
Taylor et al., "Toxic Proteins in Neurodegenerative Disease," Science 296:1991-1995 (2002).
Tirapelli, et al., "Functional characterization and expression of endothelin receptors in rat carotid artery: involvement of nitric oxide, a vasodilator prostanoid and the opening of K+ channels in ETB-induced relaxation," British journal of pharmacology 146:903-912 (2005).
Toda, et al., "Cerebral blood flow regulation by nitric oxide: recent advances," Pharmacological reviews 61:62-97 (2009).
Trollmann, et al., "HIF-1-regulated vasoactive systems are differentially involved in acute hypoxic stress responses of the developing brain of newborn mice and are not affected by levetiracetam," Brain research 1199:27-36 (2008).
Tsukahara, et al., "Molecular and functional characterization of the non-isopeptide-selective ETB receptor in endothelial cells," Receptor coupling to nitric oxide synthase. The Journal of biological chemistry 269:21778-21785 (1994).
Tsukuda, et al., "Cognitive deficit in amyloid-β-injected mice was improved by pretreatment with a low dose of telmisartan partly because of peroxisome proliferator-activated receptor-γ activation," Hypertension 54:782-787 (2009).

Vidovic, et al., "Deficiency in endothelin receptor B reduces proliferation of neuronal progenitors and increases apoptosis in postnatal rat cerebellum," Cellular and molecular neurobiology 28:1129-1138 (2008).
Viossat, et al., "Elevated tissue endothelin content during focal cerebral ischemia in the rat," Journal of cardiovascular pharmacology 22 Suppl 8:S306-309 (1993).
Virgintino, et al. "VEGF expression is developmentally regulated during human brain angiogenesis," Histochem Cell Biol 119:227-232 (2003).
Weller, et al., "Cerebral amyloid angiopathy: amyloid beta accumulates in putative interstitial fluid drainage pathways in Alzheimer's disease," The American journal of pathology 153:725-733 (1998).
Wells, "Additivity of Mutational Effects in Proteins," Biochem., 29(37):8509-17 (1990).
Wikipedia article, "Ketoacidosis" (Sep. 10, 2008) downloaded from https://web.archive.org/web/20080910125816/http://en.wikipedia.org/wiki/K- etoacidosis on Oct. 19, 2014).
Wise, et al. "New clinical guidelines for stroke published," BMJ 320:823 (2000).
Written opinion from PCT/US2014/045748 dated Nov. 13, 2014.
Yagami, et al. "Effects of an endothelin B receptor agonist on secretory phospholipase A2-IIa-induced apoptosis in cortical neurons," Neuropharmacology 48:291-300 (2005).
Yagami, et al. "Effects of endothelin B receptor agonists on amyloid beta protein (25-35)-induced neuronal cell death," Brain research 948:72-81 (2002).
Yoshizawa, et al. "Cerebrospinal fluid endothelin-1 in Alzheimer's disease and senile dementia of Alzheimer type," Neuropeptides 22:85-88 (1992).
Zhang, et al. "A selective endothelin ET(A) receptor antagonist, SB 234551, improves cerebral perfusion following permanent focal cerebral ischemia in rats," Brain research 1045:150-156 (2005).
Zhang, et al. "Astrocytes in Alzheimer's disease express immunoreactivity to the vaso-constrictor endothelin-1," Journal of the neurological sciences 122:90-96 (1994).
Zhang, et al., "Neurorestorative therapies for stroke: underlying mechanisms and translation to the clinic," Lancet Neurol 8:491-500 (2009).
Zhang, et al., "Synergistic effect of an endothelin type A receptor antagonist, S-0139, with rtPA on the neuroprotection after embolic stroke," Stroke; a journal of cerebral circulation 39:2830-2836 (2008).
Zlokovic, "New therapeutic targets in the neurovascular pathway in Alzheimer's disease," Neurotherapeutics : the journal of the American Society for Experimental NeuroTherapeutics 5:409-414 (2008).
Zuccarello, M., et al., "Endothelin B Receptor Antagonists Attenuate Subarachnoid Hemorrhage-Induced Cerebral Vasospasm," Stroke, Journal of the American Heart Association, Sep. 1998, vol. 29, No. 9, pp. 1924-1929.
Acosta et al., "Lethal Injuries and Time to Death in a Level I Trauma Center," J Am Coll Surg 186(5):528-33 (1998).
Alam et al., "Effect of different resuscitation strategies on neutrophil activation in a swine model of hemorrhagic shock," Resuscitation 60:91-99 (2004).
Alam et al., New developments in fluid resuscitation, Surg. Clin. North Am., 87(1):55-72, vi (2007).
Altman et al., Abnormal regulation of the sympathetic nervous system in alpha2A-adrenergic receptor knockout mice, Mol. Pharmacol., 56(1):154-61 (1999).
Andurkar et al., Assessment of the analgesic effect of centhaquin in mouse tail flick and hot-plate tests, Pharmacology, 88(5-6):233-41 (2011).
Angus et al., Epidemiology of severe sepsis in the United States: analysis of incidence, outcome, and associated costs of care, Crit. Care. Med., 29(7):1303-10 (2001).
Ayuste et al., "Hepatic and Pulmonary Apoptosis After Hemorrhagic Shock in Swine Can Be Reduced Through Modifications of Conventional Ringer's Solution," J Trauma 60(1):52-63 (2006).
Balogh et al., Both primary and secondary abdominal compartment syndrome can be predicted early and are harbingers of multiple organ failure, J. Trauma, 54(5):848-59; discussion 859-61 (2003).

(56) References Cited

OTHER PUBLICATIONS

Barcroft et al., On the vasodilatation in human skeletal muscle during post-haemorrhagic fainting, J. Physiol., 104(2):161-75 (1945).

Bastin et al., Salt selection and optimisation procedures for pharmaceutical new chemical entitites, Org. Process Res. & Dev., 4:427-36 (2000).

Bellamy, The causes of death in conventional land warfare: implications for combat casualty care research, Mil. Med., 149(2):55-62 (1984).

Berge et al., Pharmaceutical salts, J. Pharm. Sci., 66(1):1-19 (Jan. 1977).

Bickell et al., "The detrimental effects of intravenous crystalloid after aortotomy in swine," Surgery 110(3):529-36 (1991).

Bickell et al., "Use of Hypertonic Saline/Dextran Versus Lactated Ringer's Solution as a Resuscitation Fluid After Uncontrolled Aortic Hemorrhage in Anesthetized Swine," Ann Emerg Med 21(9):1077-85 (1992).

Bickell et al., Immediate versus delayed fluid resuscitation for hypotensive patients with penetrating torso injuris, N. Engl. J. Med., 331(17):1105-9 (1994).

Brierley et al., Clinical practice parameters for hemodynamic support of pediatric and neonatal septic shock: 2007 update from the American College of Critical Care Medicine, Crit. Care Med., 37(2):666-88 (2009).

Briyal et al., "Alterations in Endothelin Receptors Following Hemorrhage and Resuscitation by Centhaquin," Physiological Research 67(1):199-214 (2018).

Bulger et al., Out-of-hospital hypertonic resuscitation after traumatic hypovolemic shock: a randomized, placebo controlled trial, Ann. Surg., 253(3):431-41 (2011).

Bulger et al., Out-of-hospital hypertonic resuscitation following severe traumatic brain injury: a randomized controlled trial, JAMA, 304(13):1455-64 (2010).

Bylund et al., International Union of Pharmacology nomenclature of adrenoceptors, Pharmacol. Rev., 46(2):121-36 (1994).

Cai et al., Novel insights for systemic inflammation in sepsis and hemorrhage, Mediators Inflamm. 2010:642462 (2010).

Cavun et al., Evidence that hemorrhagic hypotension is mediated by the ventrolateral periaqueductal gray region, Am. J. Physiol. Regul. lntegr. Comp. Physiol., 281(3):R747-52 (2001).

Chappell et al., A rational approach to perioperative fluid management, Anesthesiology, 109(4):723-40 (2008).

De Boode, Clinical monitoring of systemic hemodynamics in critically ill newborns, Early Hum. Dev., 86(3):137-41 (2010).

Drabek et al., Intravenous hydrogen sulfide does not induce hypothermia or improve survival from hemorrhagic shock in pigs, Shock, 35(1):67-73 (2011).

Dries et al., "Hyotensive Resuscitation," Shock 6(5):311-316 (1996).

Dubick et al., Issues of concern regarding the use of hypertonic/hyperoncotic fluid resuscitation of hemorrhagic hypotension, Shock, 25(4):321-8 (2006).

Dung et al., Fluid replacement in dengue shock syndrome: a randomized, double-blind comparison of four intravenous-fluid regimens, Clin. Infect. Dis., 29(4):787-94 (1999).

Engstrom et al., "Acidosis Impairs the Coagulation: A Thromboelastograhic Study," J Trauma 61(3):624-8 (2006).

First Office Action (English translation), Chinese patent application No. 201280076674.9, dated Jun. 20, 2016.

Ganster et al., Effects of hydrogen sulfide on hemodynamics, inflammatory response and oxidative stress during resuscitated hemorrhagic shock in rats, Crit. Care, 14(5):R165 (2010).

Gavras et al., "The $\alpha_2$-adrenergic receptors in hypertension and heart failure: experimental and clinical studies," Journal of Hypertension 19(12):2115-24 (2001).

Gill et al., "Effects of agmatine on the survival rate in rats bled to hemorrhage," Arzneimittelforschung 61(4):229-33 (2011).

Gonzales et al., "Hepatoprotection and Lethality Rescue by Histone Daecetylase Inhibitor Valproic Acid in Fatal Hemorrhagic Shock," J Trauma 65:554-565 (2008).

Gubler, The changing epidemiology of yellow fever and dengue, 1900 to 2003: full circle?, Comp. Immunol. Microbiol. Infect. Dis., 27(5):319-30 (2004).

Gulati et al., "Endothelin Receptor Alteration Following Hemorrhagic Shock and Resuscitation by Centhaquin," Circulation 136(1), 2 pages, Abstract 20622 (2017).

Gulati et al., "Role of adrenergic mechanisms in the pressor effect of diaspirin cross-linked hemoglobin," J Lab Clin Med 124(1):125-33 (1994).

Gulati et al., "Role of endothelin-converting enzyme in the systemic hemodynamics and regional circulatory effects of proendothelin-1 (1-38) and diaspirin cross-linked hemoglobin in rats," J Lab Clin Med 126(6):559-70 (1995).

Gulati et al., "Role of ET and NO in resuscitative effect of diaspirin cross-linked hemoglobin after hemorrhage in rat," Am J Physiol 273(2 Pt 2):H827-36 (1997).

Gulati et al., Centhaquin improves resuscitative effect of hypertonic saline in hemorrhaged rats, J. Surg. Res., 178(1):415-23 (2012).

Guzman et al., Dengue: a continuing global threat, Nat. Rev. Microbiol., 8(12 suppl):S7-16 (2010).

Guzman et al., Dengue: an update, Lancet Infect. Dis., 2(1):33-42 (2002).

Guzman et al., Update on the global spread of dengue, Int. J. Antimicrob. Agents, 36 Suppl 1:S40-2 (2010).

Hardy et al., Massive transfusion and coagulopathy: pathophysiology and implications for clinical management, Can. J. Anaesth., 53(6 Suppl):S40-58 (2006).

Hein et al., Two functionally distinct alpha2-adrenergic receptors regulate sympathetic neurotransmission, Nature, 402(6758):181-4 (1999).

Henrion et al., Potentiation of norepinephrine-induced contractions by endothelin-1 in the rabbit aorta, Hypertension, 22(1):78-83 (1993).

Heslop et al., "Haemorrhage-Evoked Compensation and Decompensation are Mediated by Distinct Caudal Midline Medullary Regions in the Urethane-Anaesthetised Rat," Neuroscience 113(3):555-67 (2002).

Hierholzer et al., Essential role of induced nitric oxide in the initiation of the inflammatory response after hemorrhagic shock, J. Exp. Med., 187(6):917-28 (1998).

Ho et al., "Excessive Use of Normal Saline in Managing Traumatized Patients in Shock: A Preventable Contributor to Acidosis," J Trauma 51(1):173-7 (2001).

Hsia et al., A hemoglobin-based multifunctional therapeutic: polynitroxylated pegylated hemoglobin, Artif. Organs, 36(2):215-20 (2012).

International Search Report and Written Opinion in international application No. PCT/US2019/030652 dated Jul. 25, 2019.

International Search Report and Written Opinion, International Application No. PCT/US12/60257, dated Mar. 18, 2013.

Jansen et al., "Blood lactate monitoring in critically ill patients: A systematic health technology assessment," Crit Care Med 37(10):2827-2839 (2009).

Kauvar et al., Impact of hemorrhage on trauma outcome: an overview of epidemiology, clinical presentations, and therapeutic considerations, J. Trauma, 60(6 Suppl):53-11 (2006).

Khongphatthanayothin et al., "Myocardial depression in dengue hemorrhagic fever: Prevalence and clinical description," Pediat Crit Care Med 8(6):524-9 (2007).

Kovács et al., "Alpha2 antagonist yohimbine suppresses maintained firing of rat prefrontal neurons in vivo," Neuroreport 14(6):833-6 (2003).

Kowalenko et al., Improved outcome with hypotensive resuscitation of uncontrolled hemorrhagic shock in a swine model, J. Trauma, 33(3):349-53 (1992).

Kumar et al., Nationwide Trends of Severe Sepsis in the 21st Century (2000-2007) Chest 140(5):1223-31 (2011).

Li et al., Ideal permissive hypotension to resuscitate uncontrolled hemorrhagic shock and the tolerance time in rats, Anesthesiology, 114(1):111-9 (2011).

Lima et al., The prognostic value of the subjective assessment of peripheral perfusion in critically ill patients, Crit. Care Med., 37(3):934-8 (2009).

(56) References Cited

OTHER PUBLICATIONS

Liu et al., Hemorrhage-induced vascular hyporeactivity to norepinephrine in select vasculatures of rats and the roles of nitric oxide and endothelin, Shock, 19(3):208-14 (2003).

Makaritsis et al., Role of alpha(2)-adrenergic receptor subtypes in the acute hypertensive response to hypertonic saline infusion in anephric mice, Hypertension, 35(2):609-13 (2000).

Makaritsis et al., Role of the alpha2B-adrenergic receptor in the development of salt-induced hypertension, Hypertension, 33(1):14-7 (1999).

Malone et al., Massive transfusion practices around the globe and a suggestion for a common massive transfusion protocol, J. Trauma, 60(6 Suppl):S91-6 (2006).

Martini et al., "Acidosis and Coagulopathy—The Differential Effects on Fibrinogen Synthesis and Breakdown in Pigs," Annals of Surgery 246(5):831-835 (2007).

Merck Manual 17th edition Japanese version (English translation), pp. 1709-1706 (1999).

Morens et al., Dengue and hemorrhagic fever: a potential threat to public health in the United States, JAMA, 299(2):214-6 (2008).

Morissette et al., High-throughput crystallization: polymorphs, salts, co-crystals and solvates of pharmaceutical solids, Adv. Drug Deliv. Rev., 56(3):275-300 (Feb. 2004).

Morrison et al., "Hypotensive Resuscitation Strategy Reduces Transfusion Requirements and Severe Postoperative Coagulopathy in Trauma Patients with Hemorrhagic Shock: Preliminary Results of a Randomized Controlled Trial," The Journal of Trauma Injury, Infection, and Critical Care 70(3):652-663 (2011).

Notification of Reasons for Refusal (English translation), Japanese patent application No. 2015-529776, dated Apr. 12, 2016.

Pfeifer et al., Role of hemorrhage in the induction of systemic inflammation and remote organ damage: analysis of combined pseudo-fracture and hemorrhagic shock, J. Orthop. Res., 29(2):270-4 (2011).

Philipp et al., "Placental $_2$-adrenoceptors control vascular development at the interface between mother and embryo," Nature Genetics 31(3):311-315 (2002).

Premaratna et al., Should colloid boluses be prioritized over crystalloid boluses for the management of dengue shock syndrome in the presence of ascites and pleural effusions?, BMC Infect. Dis., 11:52 (2011).

Ranjit et al., "Aggressive managemenet of dengue shock syndrome may decrease mortality rate: A suggested protocol," Pediatr Crit Care Med 6(4):412-9 (2005).

Reagan-Shaw et al., Dose translation from animal to human studies revisited, FASEB J., 22(3):659-61 (Mar. 2008).

Rhee et al., A study of the safety and efficacy of travoprost 0.004%/timolol 0.5% ophthalmic solution compared to latanoprost 0.005% and timolol 0.5% dosed concomitantly in patients with open-angle glaucoma or ocular hypertension, Clin. Ophthalmol., 2(2):313-9 (2008).

Rhee et al., Searching for the optimal resuscitation method: recommendations for the initial fluid resuscitation of combat casualties, J. Trauma, 54(5Suppl):S52-62 (2003).

Sakai et al., Hemoglobin vesicles and red blood cells as carriers of carbon monoxide prior to oxygen for resuscitation after hemorrhagic shock in a rat model, Shock, 31(5):507-14 (2009).

San Martin et al., The epidemiology of dengue in the americas over the last three decades: a worrisome reality, Am. J. Trop Med. Hyg., 82(1):128-35 (2010).

Santry et al., Fluid resuscitation: past, present, and the future, Shock, 33(3):229-41 (2010).

Schadt et al., "Hemodynamic and neurohumoral responses to acute hypovolemia in conscious mammals," Am J Physiol 260(2 Pt 2):H305-18 (1991).

Shackford et al., "The Epidemiology of Traumatic Death," Arch Surg 128(5):571-5 (1993).

Sharma et al., "Yohimbine modulates diaspirin crosslinked hemoglobin-induced systemic hemodynamics and regional circulatory effects," Critical Care Medicine 23(5):874-84 (1995).

Singhi et al., Dengue and dengue hemorrhagic fever: management issues in an intensive care unit, J. Pediatr. (Rio J.), 83(2Suppl):S22-35 (2007).

Srimal et al., "Studies on 2-(2-(4-(3-Methylphenyl)1-Piperazinyl)Ethyl Quinoline (Centhaquin), a Centrally Acting Antihypertensive II.Effect on Cardiohaemodynamics," Asia Pacific Journal of Pharmacology 5:185-190 (1990).

Tabuchi et al., "Endothelin Enhances Adrenergic Vasoconstriction in Perfused Rat Mesenteric Arteries," 159(3):1304-1308 (1989).

Tavares et al., Localization of alpha 2A- and alpha 2B-adrenergic receptor subtypes in brain, Hypertension, 27(3 Pt 1):449-55 (1996).

Tolentino, et al. "Role of Centhaquin in the Resuscitatin of Hemorrhagic Shock," Chest. 2011.

Vacher et al., "Rigid Analogues of the α2-Adrenergic Blocker Artipamezole: Small Changes, Big Consequences," Journal of Medicinal Chemistry 53(19):6986-95 (2010).

Vincenzi et al, "Small volume resuscitation with 3% hypertonic saline solution decrease inflammatory response and attenuates end organ damage after controlled hemorrhagic shock," Am J Surg 198(3):407-14 (2009).

Vippagunta et al., Crystalline solids, Adv. Drug Deliv. Rev., 48(1):3-26 (May 2001).

Virtanen et al., "Highly Selective and Specific Antagonism of Central and Peripheral α2-Adrenoceptors by Atipamezole," Arch. Int. Pharmacodyn. 297:190-204 (1989).

Watters et al., "Fluid Resuscitation Increases Inflammatory Gene Transcription After Traumatic Injury," J Trauma 61(2):300-309 (2006).

Watts et al., Hypothermic coagulopathy in trauma: effect of varying levels of hypothermia on enzyme speed, platelet function, and fibrinolytic activity, J. Trauma, 44(5):846-54 (1998).

Wills et al., Comparison of three fluid solutions for resuscitation in dengue shock syndrome, N. Engl. J. Med., 353(9):877-89 (2005).

Wu et al., Low-volume resuscitation from traumatic hemorrhagic shock with Na+/H+ exchanger inhibitor, Crit. Care Med., 37(6):1994-9 (2009).

Zacharias et al., "Histone Deacetylase Inhibitors Prevent Apoptosis following Lethal Hemorrhagic Shock in Rodent Kidney Cells," Resuscitation 82(1):105-109 (2011).

Figure 1
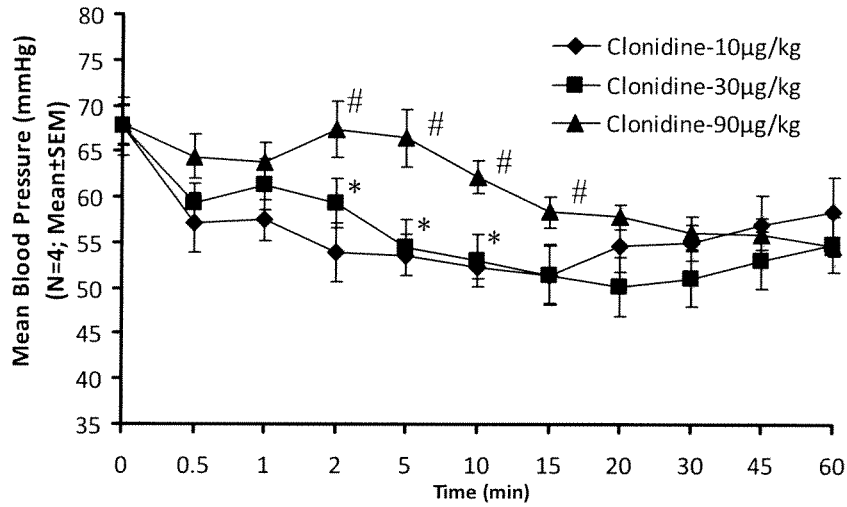
Figure 1A
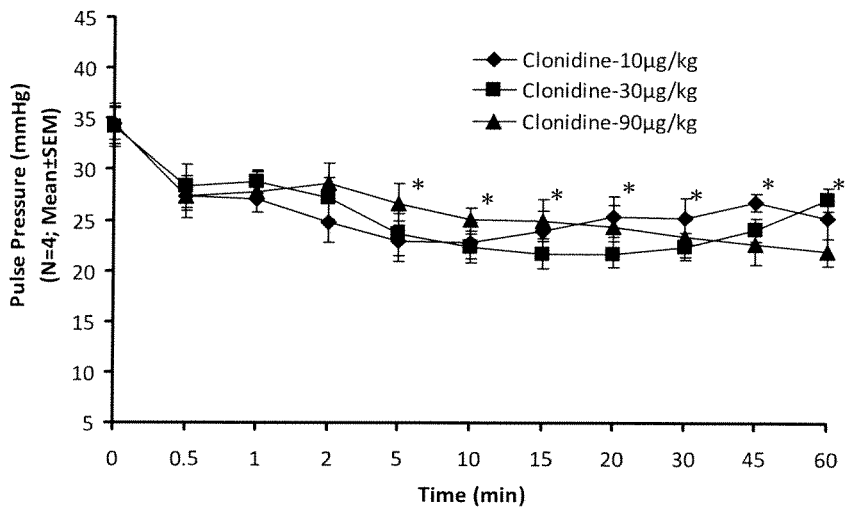
Figure 1B
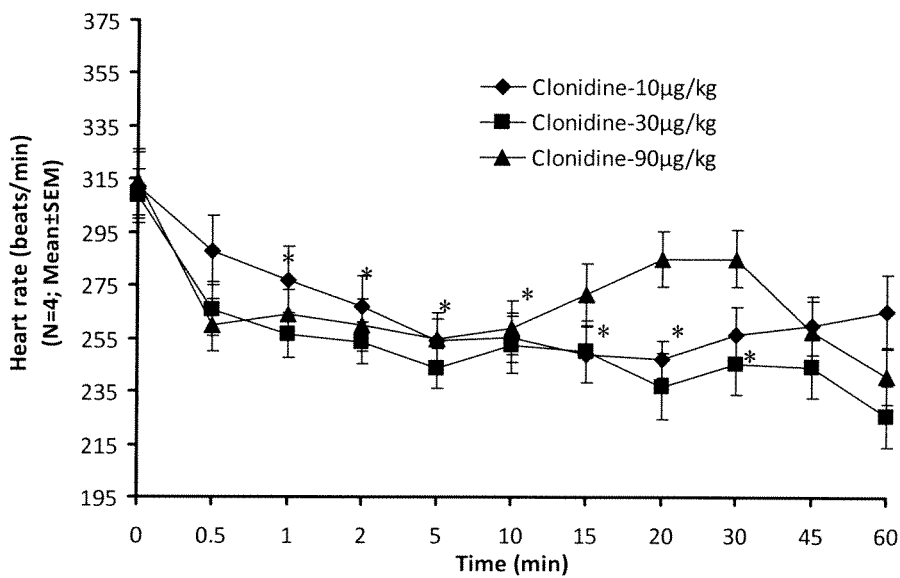
Figure 1C

Figure 2
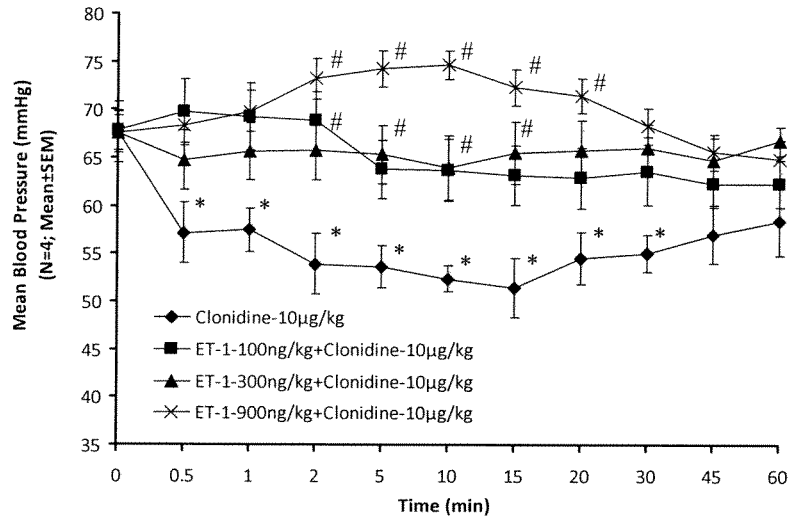
Figure 2A
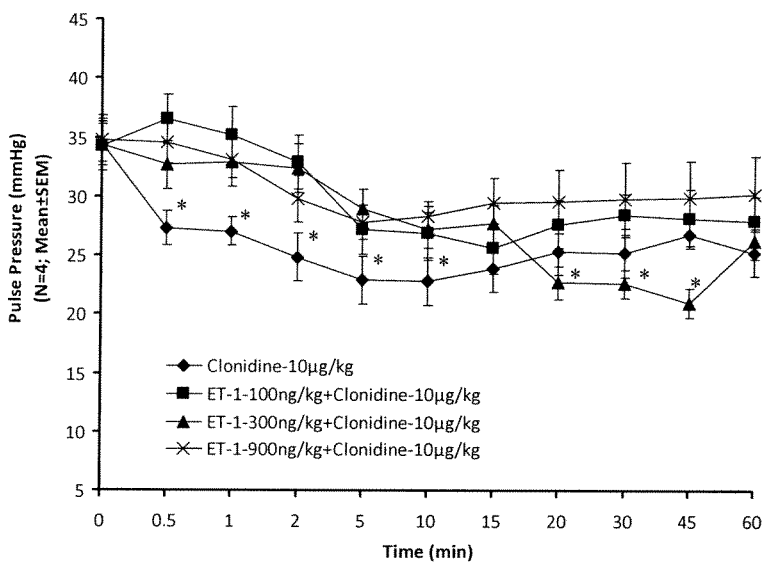
Figure 2B
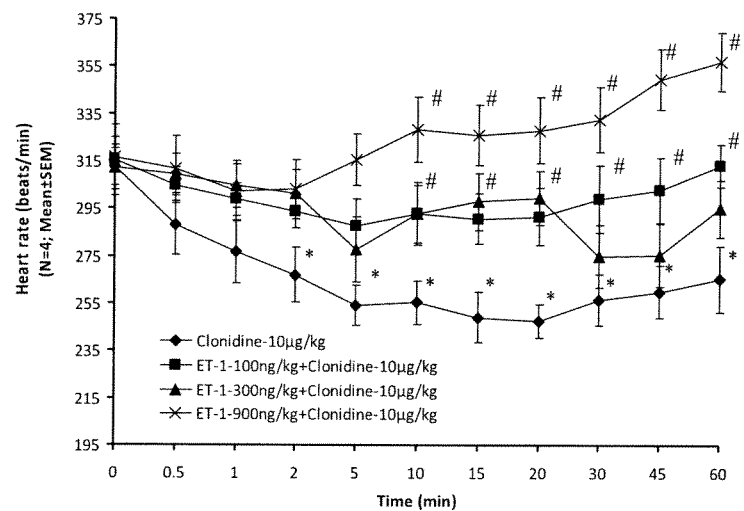
Figure 2C

Figure 3
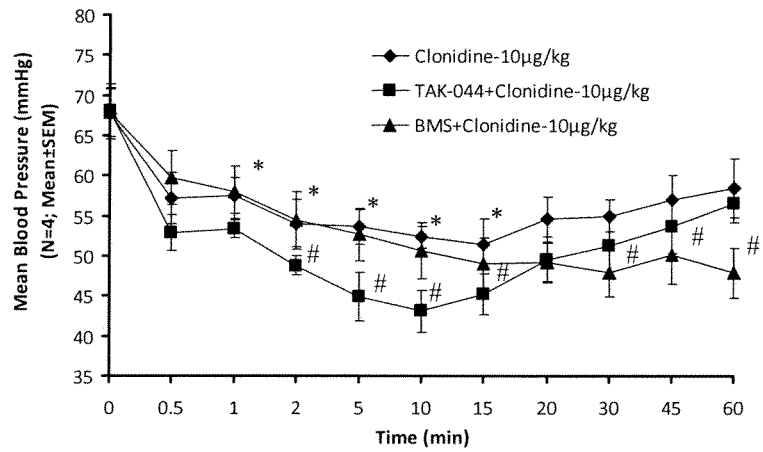
Figure 3A
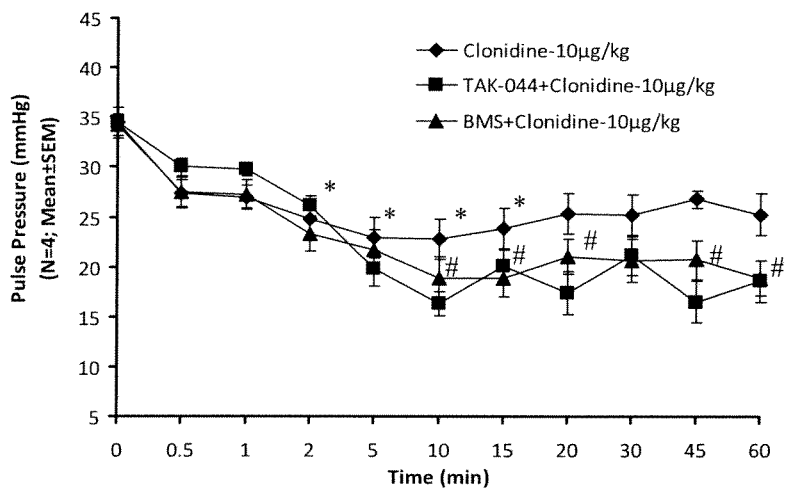
Figure 3B
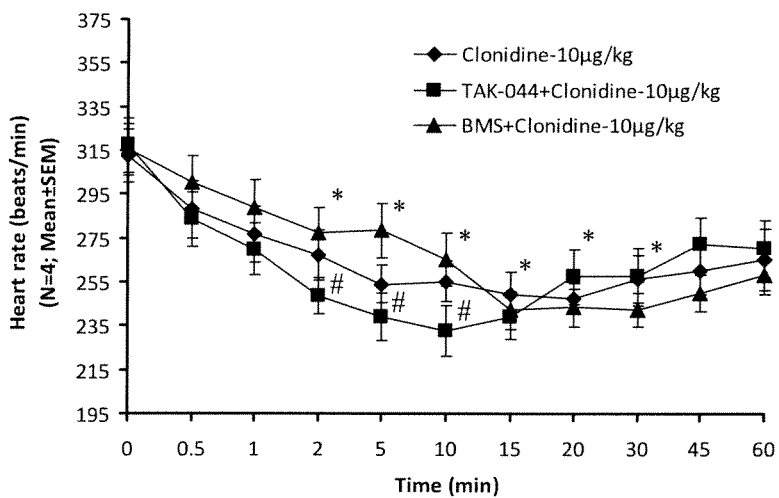
Figure 3C

Figure 4
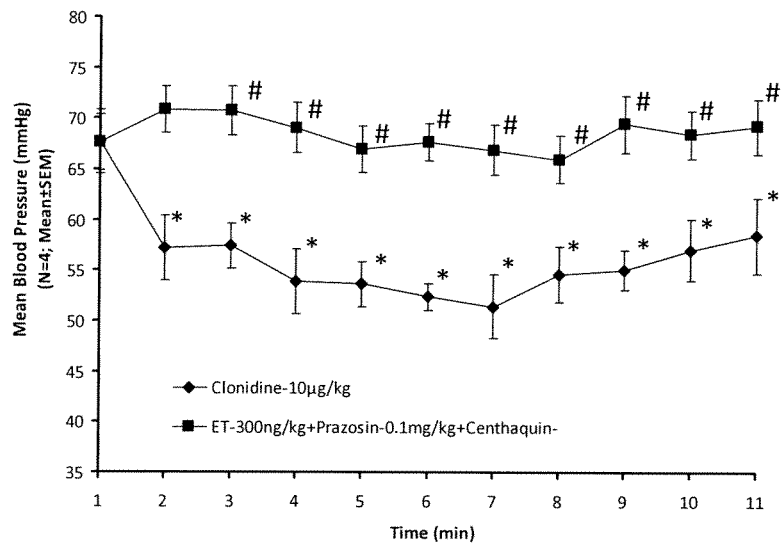
Figure 4A
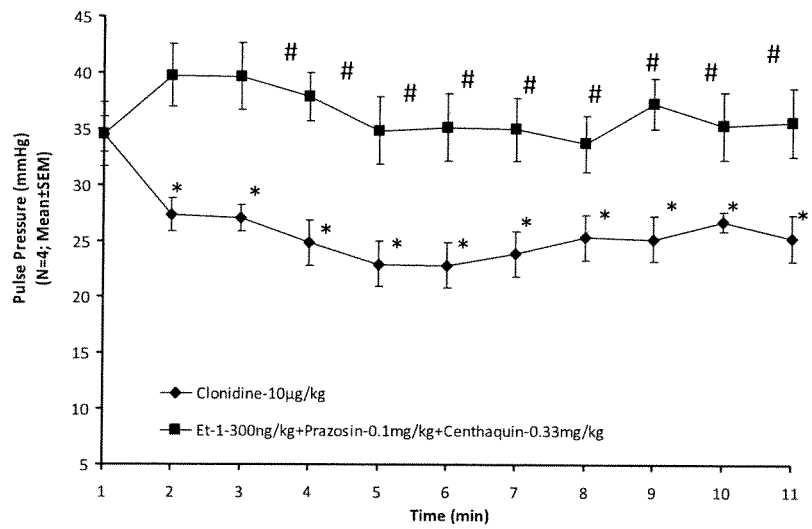
Figure 4B
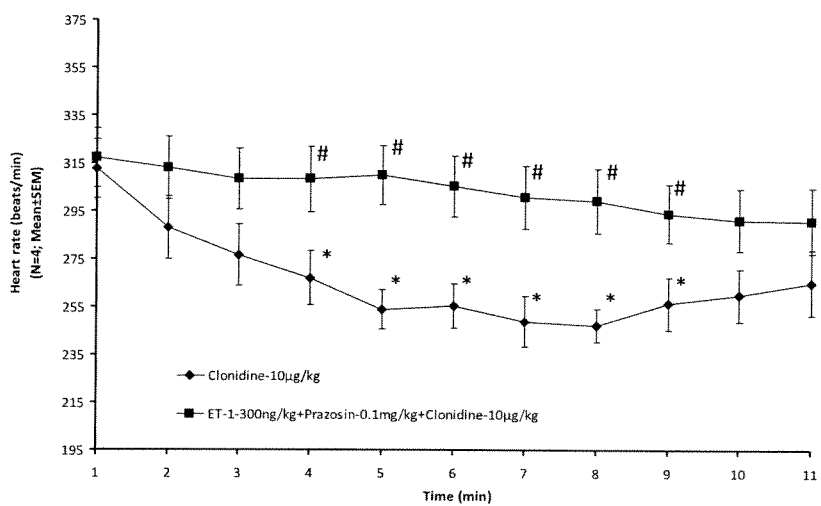
Figure 4C

Figure 5
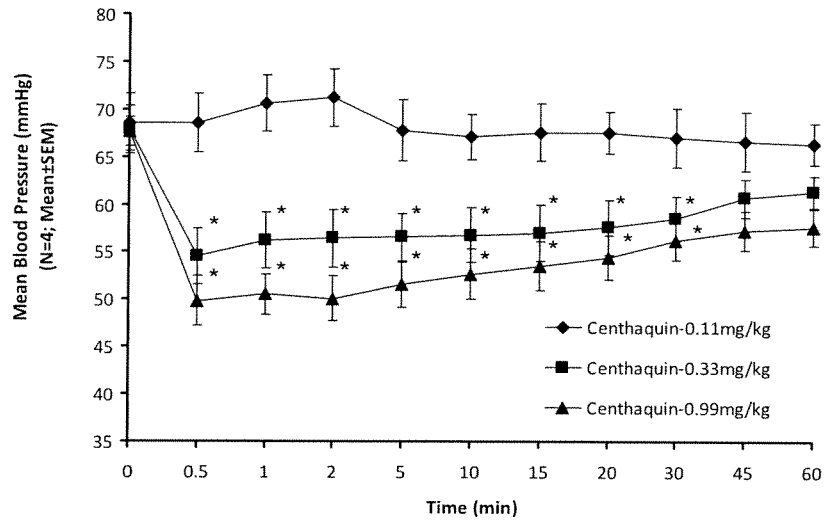
Figure 5A
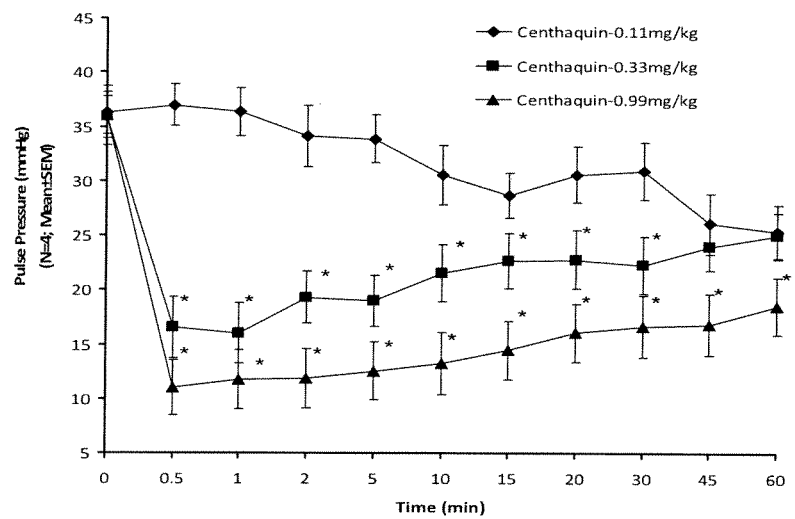
Figure 5B
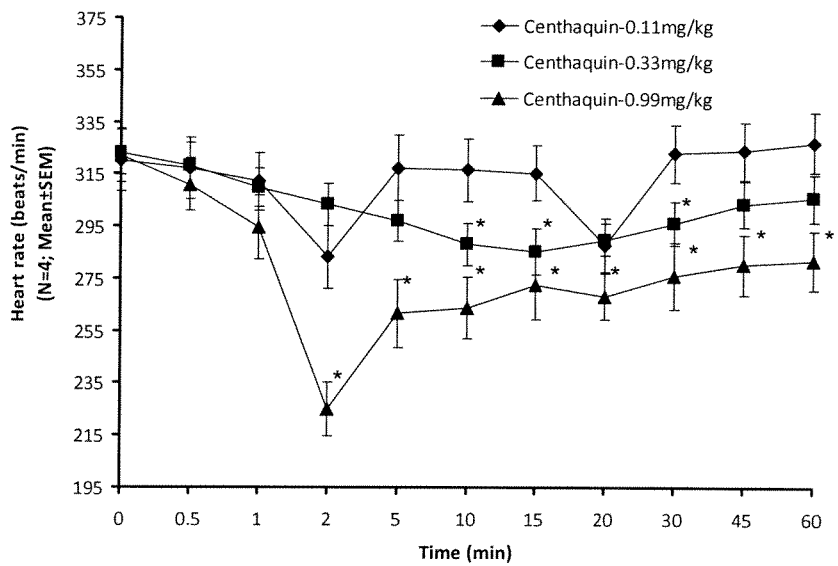
Figure 5C

Figure 6
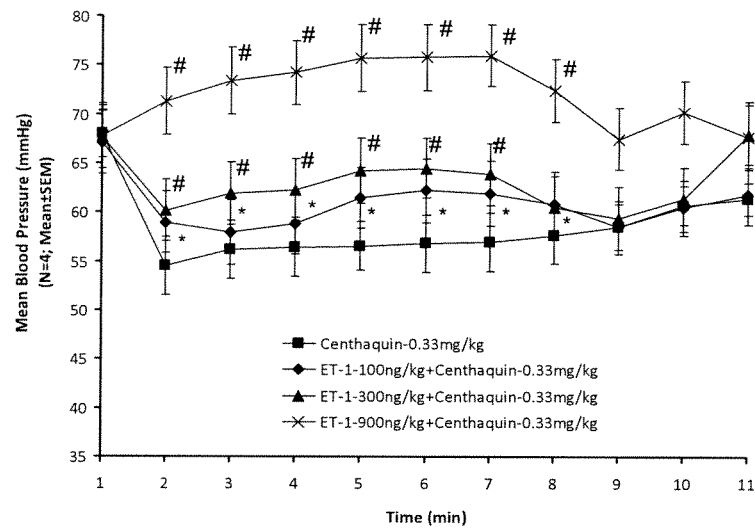
Figure 6A
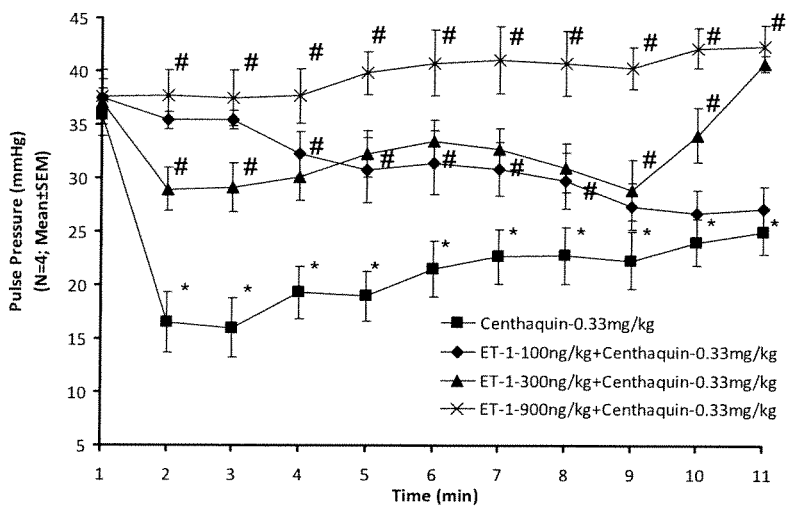
Figure 6B
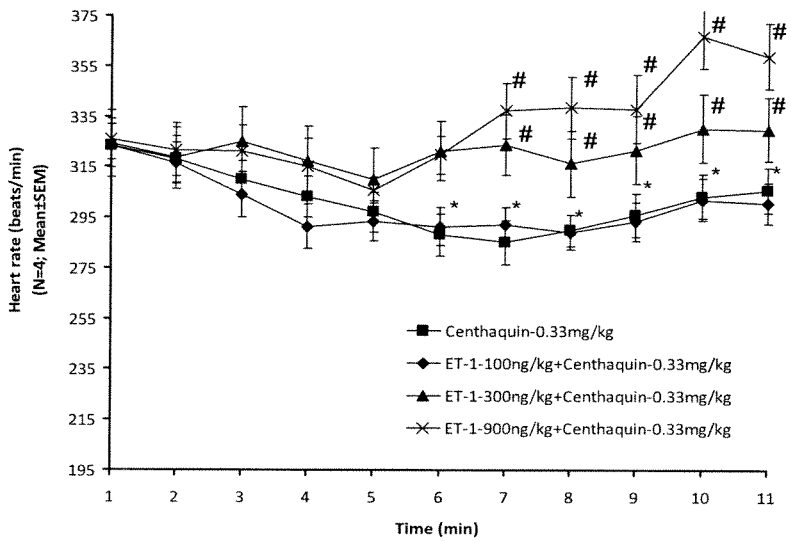
Figure 6C

Figure 7
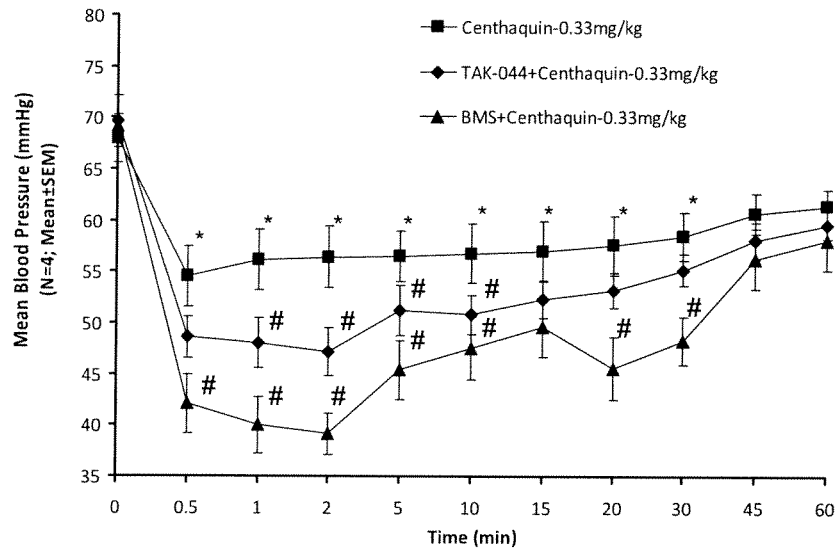
Figure 7A
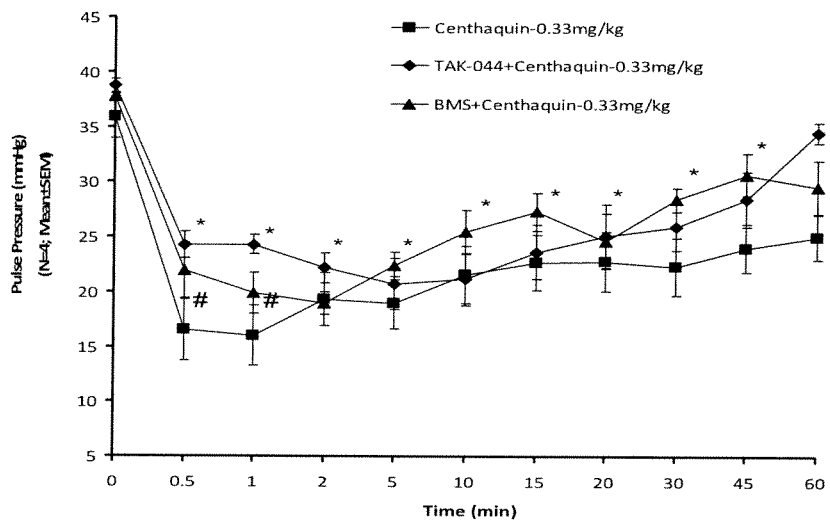
Figure 7B
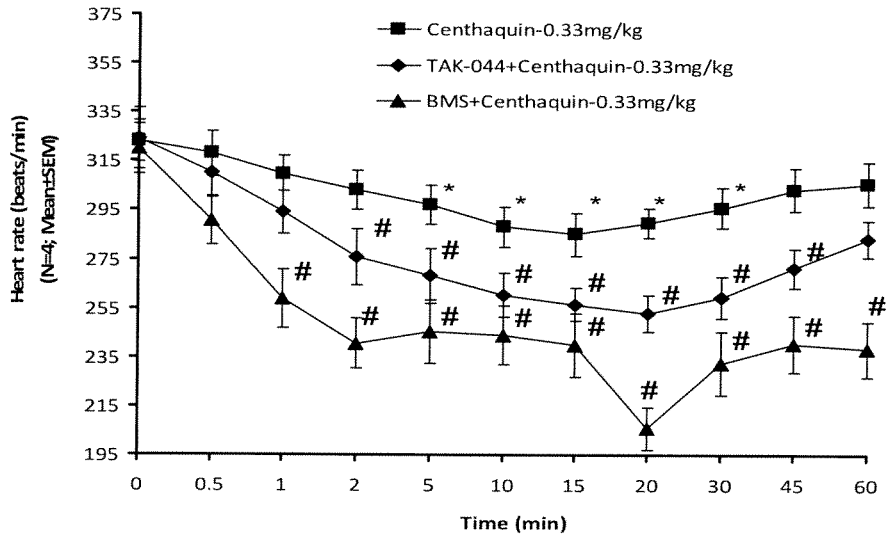
Figure 7C

Figure 8
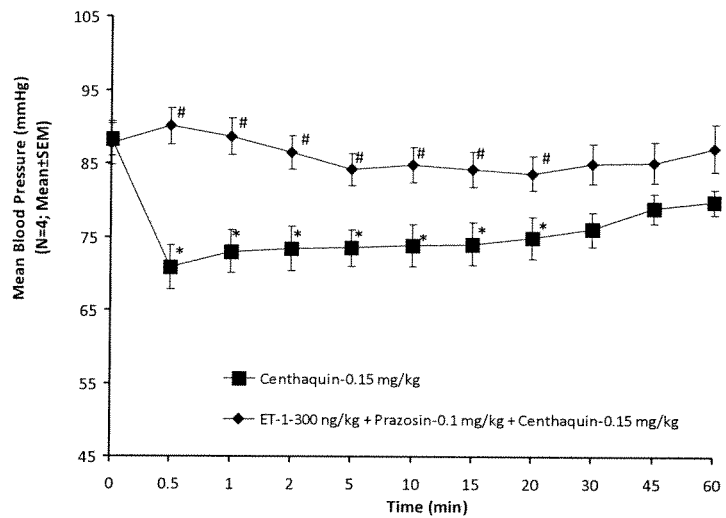
Figure 8A
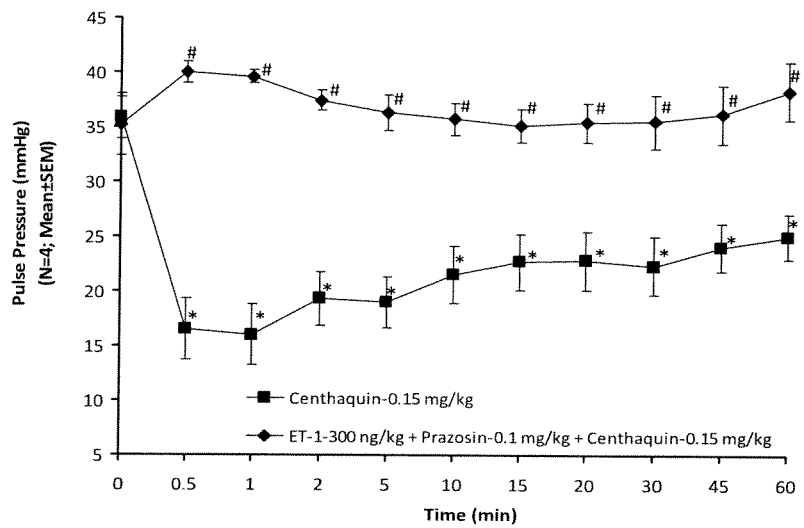
Figure 8B
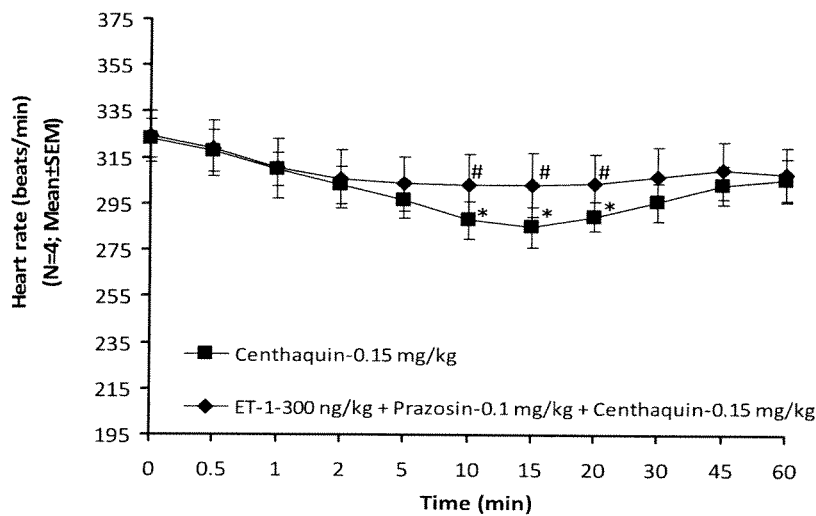
Figure 8C

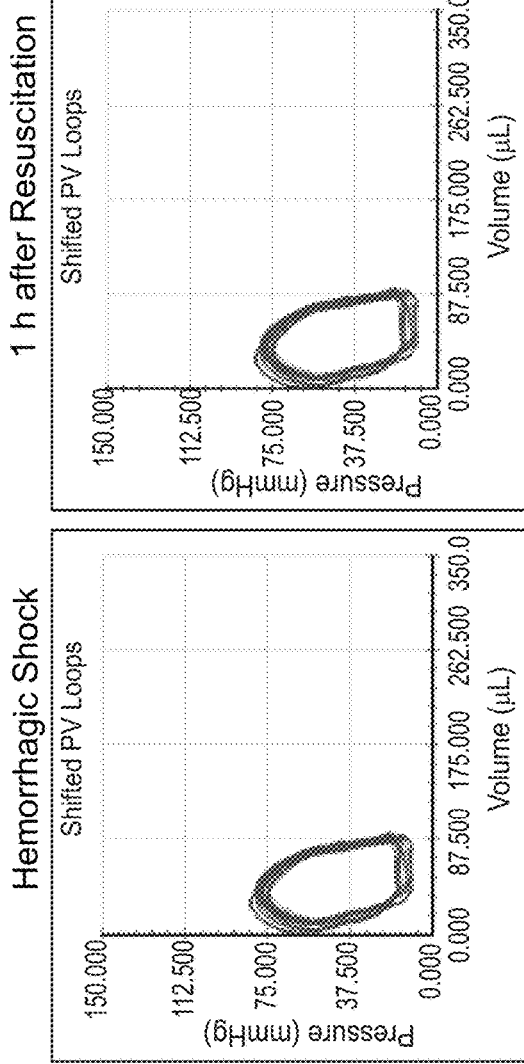
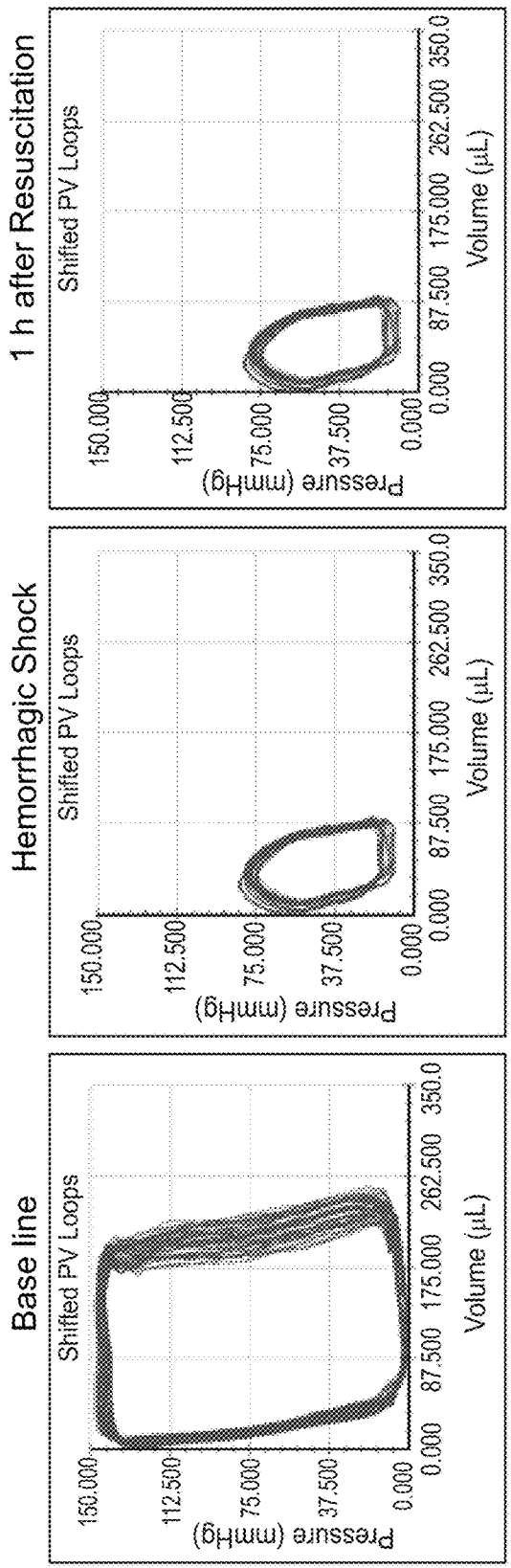
Fig. 19A  Fig. 19B  Fig. 19C
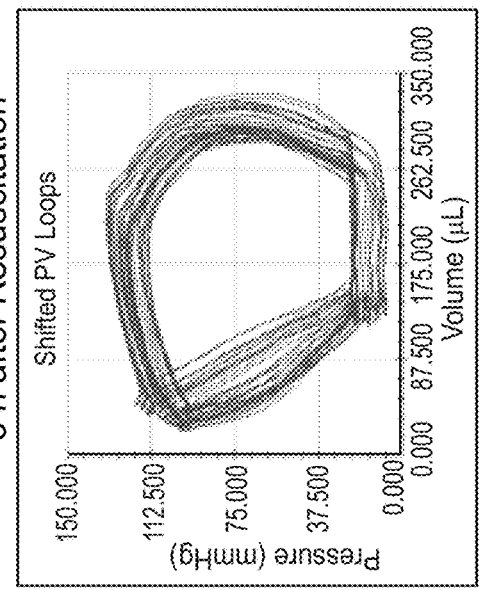
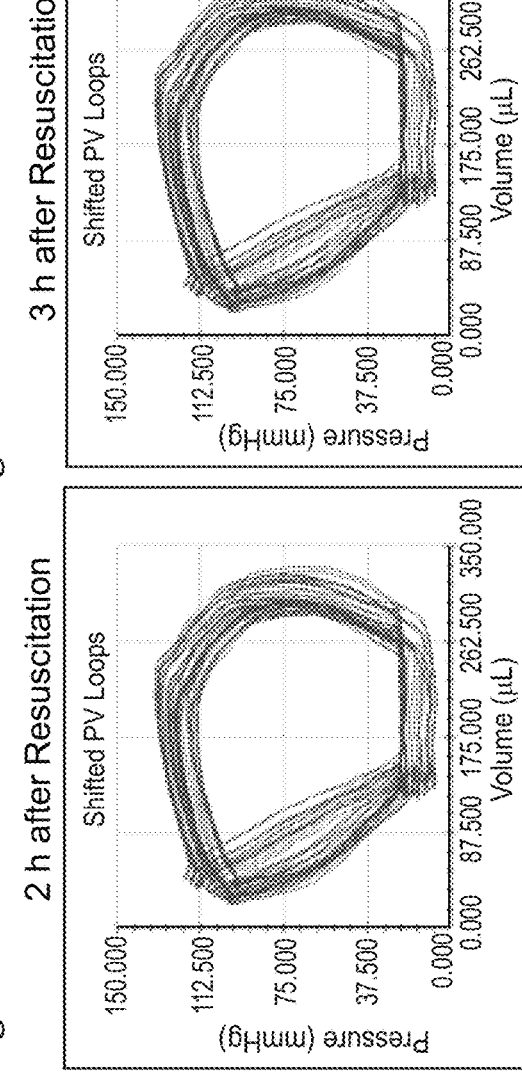
Fig. 19D  Fig. 19E

THERAPEUTIC TREATMENTS USING CENTHAQUIN

CROSS-REFERENCE TO RELATED APPLICATIONS

This application is a Continuation of U.S. application Ser. No. 13/266,205, filed Dec. 9, 2011 (now abandoned), which is the U.S. national phase of International Application No. PCT/US2010/032942, filed Apr. 29, 2010, which claims the benefit of U.S. provisional patent Application No. 61/174,257, filed Apr. 30, 2009, incorporated herein in its entirety by reference.

FIELD OF THE INVENTION

The present invention relates to novel therapeutic treatments using centhaquin. In one embodiment, centhaquin is used in conjunction with an endothelin antagonist in the treatment of hypertension. In a second embodiment, centhaquin is used as an analgesic in the treatment of pain. In a third embodiment, centhaquin is used in the treatment of resuscitative hemorrhagic shock.

BACKGROUND OF THE INVENTION

Hypertension is a serious disease that afflicts many people all over the world. It is estimated that one in three Americans suffer from high blood pressure, with as much as one-third of them are unaware of the problem. Beyond lifestyle changes such as exercise, losing weight, and reducing salt intake, most antihypertensive therapy involves the use of one or more antihypertensive drugs. In addition to diuretics, $Ca^{++}$-channel blockers, adrenergic blockers, ACE inhibitors, and angiotensin-II receptor blockers, centrally acting hypotensive drugs are available for the treatment of moderate to severe hypertension.

Clonidine, N-(2,6-dichlorophenyl)-4,5-dihydro-1H-imidazol-2-amine, is a widely used antihypertensive drug that mediates its hypotensive effects via stimulation of central $\alpha_2$-adrenergic receptors (Kobinger, 1978; Guyenet and Cabot, 1981). It has an approximately 10-fold higher binding affinity for the $\alpha_2$-adrenergic receptors than the $\alpha_1$-adrenoreceptors (U'Prichard et al., 1977). Centrally acting antihypertensive drugs are used to treat uncontrolled or refractory hypertension. However, use is limited due to dual action. When administered, first they stimulate peripheral $\alpha_1$-adrenergic receptors resulting in vasoconstriction and an increase in blood pressure, and second they act on the central $\alpha_2$-adrenergic receptors to inhibit sympathetic drive resulting in vasodilatation and a decrease in blood pressure. The central action predominates over the peripheral, and hence the overall effect of clonidine is decrease in blood pressure.

Centhaquin (2-[2-(4-(3-methylphenyl)-1-piperazinyl) ethyl-quinoline) is a centrally acting antihypertensive drug. The structure of centhaquin was determined (Bajpai et al., 2000) and the conformation of centhaquin was confirmed by X-ray diffraction (Carpy and Saxena, 1991). Although structurally different from clonidine, centhaquin produces a fall in mean arterial pressure (MAP) and heart rate (HR) similar to that seen with clonidine in anesthetized cats and rats (Srimal et al., 1990). In mice, it has LD50 of 600 mg/kg intraperitoneal and produces a dose-dependent fall in MAP in various species. Centhaquin (0.05 to 0.2 mg/kg, iv) produced a dose-dependent decrease in MAP and HR in urethane anesthetized rats. However, in cervical sectioned rats, intravenously administered centhaquin did not produce any effect on MAP or HR (Gulati et al., 1991a). Intrathecal administration of centhaquin did not produce any effect on MAP or HR (Gulati et al., 1991a). Intraduodenal administration of centhaquin (1.0 to 2.5 mg/kg) produced a 40 to 50 mmHg fall in MAP, which was not affected by pretreatment with antihistaminics and atropine (Murthi et al., 1976; Srimal et al., 1990). In spontaneously hypertensive rats, centhaquin (0.5 to 1.0 mg/kg) was effective in lowering the MAP by 50 to 60 mmHg. Repeated administration of centhaquin once a day for 15 days did not produce any potentiation or tolerance (Murthi et al., 1976).

Centhaquin (0.1, 1.0 and 10.0 µg/ml) was found to produce an initial increase followed by decrease of spontaneous release of norepinephrine (NE) and inhibited norepinephrine release evoked by potassium chloride and dimethyl phenyl piperazinium chloride indicating that centhaquin inhibits norepinephrine release (Bhatnagar et al., 1985). Upon chronic administration in rats, both centhaquin and clonidine produced hypotension and bradycardia associated with an up-regulation in $\alpha$-adrenergic receptors in the hypothalamus and medulla (Gulati et al., 1991a; Gulati et al., 1991b). It is possible that a decrease in release of norepinephrine in the synapse leads to an increase in the density of $\alpha$-adrenergic receptors.

The central regulation of blood pressure has been linked to an endogenous 21-residue peptide, endothelin (ET). ET was discovered two decades ago in porcine arterial epithelial cells, and has since been recognized as one of the most potent vasoconstrictors (Hickey et al., 1985; Yanagisawa et al., 1988). There are three structurally and functionally distinct isopeptides (ET-1, ET-2, and ET-3), which in turn bind to three different receptors ($ET_A$, $ET_{B1}$, and $ET_{B2}$). $ET_A$ and $ET_{B2}$ receptors are located on the vascular smooth muscle where they produce vasoconstriction via the increase in intracellular $Ca^{++}$. On the other hand, $ET_{B1}$ receptors are found on the vascular endothelium where they mediate vasorelaxation via the synthesis and release of nitric oxide and prostacyclin (Sakamoto et al., 1993; Shetty et al., 1993). Administration of ET-1 intravenously produces a dose-dependent, biphasic alteration in blood pressure, characterized by a brief hypotensive phase followed by a sustained hypertension along with an increase in HR (Ouchi et al., 1989; Kuwaki et al., 1990). ET is present in the brain, and central ET has been shown to regulate sympathetic nervous system (Gulati et al., 1997a; Gulati et al., 1997b).

It previously was found that ET can modify the cardiovascular effects of clonidine. Pre-treatment with ET in rats produced an antagonistic effect on the hypotension and bradycardia induced by clonidine. A postulated mechanism is that ET increased the sensitivity of peripheral $\alpha$-adrenergic receptors, leading to potentiation of the peripheral hypertensive effects of clonidine (Gulati, 1992; Gulati and Srimal, 1993). Studies have shown that ET attenuates the pressor response and [$^3$H]norepinephrine release during stimulation of the rat mesenteric artery and the guinea pig femoral artery, thereby resulting in presynaptic inhibition and a subsequent increase in sympathetic tone (Wiklund et al., 1988; Tabuchi et al., 1989). It is therefore possible that the central hypotensive and bradycardic effects of clonidine could be antagonized by ET due to ET-mediated inhibition of presynaptic neuronal transmission.

It is known that there is a significant alteration of clonidine-induced cardiovascular parameters by ET and few ET antagonists already in market for the treatment of pulmonary hypertension and several are in pipeline. The effect of ET and their antagonists on adrenergic antihypertensive agent-induced changes in cardiovascular parameters therefore was studied. Structurally different compounds clonidine and centhaquin have been shown to have similar effects on blood pressure by acting on central and peripheral α-adrenergic receptors. The inventors therefore explored the involvement of ET in the modulation of peripheral adrenergic effects of clonidine and centhaquin. The study was conducted in rats using ET agonist (ET-1) and antagonists (BMS-182874 ($ET_A$-specific antagonist) and TAK-044 ($ET_{A/B}$ non-specific antagonist)) to investigate their effect on clonidine and centhaquin induced changes in MAP, pulse pressure (PP), and HR.

Analgesics are agents that relieve pain by acting centrally to elevate pain threshold, preferably without disturbing consciousness or altering other sensory functions. A mechanism by which analgesic drugs obtund pain (i.e., raise the pain threshold) has been formulated.

National Center for Health Statistics (2006) estimates more than one-quarter of Americans (26%) over the age of 20 years, and more than 76.5 million Americans, report that they have had a problem with pain of any sort that persisted for more than 24 hours in duration and over 191 million acute pain events occurred in the United States. Opioids are the most commonly used analgesics for the clinical management of acute and chronic pain. There are various side effects associated with the long-term use of opioids including the development of tolerance, which results in inadequate pain relief. There are several existing regimens designed to enhance analgesia and effectively manage pain, including nonsteroidal anti-inflammatory drugs (NSAIDS), additional opioids, and non-opioids in combination with opioid therapy. Although these approaches provide symptomatic relief, they have little effect on the underlying mechanisms that contribute to the development of tolerance and pose a significant risk of toxicity, dependence, and addiction.

Thus there exists a need in the art to identify agents, or combinations of agents that reduce tolerance to opioid analgesics and reduce pain symptoms, and that can act as effective non-opioid analgesics.

SUMMARY OF THE INVENTION

The present invention is directed to administration of an endothelin antagonist in combination with centhaquin or other adrenergic agents to an individual in need thereof. More particularly, administration of centhaquin or other adrenergic agents in combination with an endothelin antagonist potentiates the antihypertensive effect of the centhaquin.

Adrenergic agents useful in accordance with the present invention include, but are not limited to, centhaquin, clonidine, guanfacine, guanabenz, guanoxbenz, methyldopa, prazosin, tamsulosin, doxazosin, terazosin, phentolamine, phenoxybenzamine, mirtazapine, and mixtures thereof. The adrenergic agent is administered in conjunction with an endothelin antagonist in the treatment of hypertension. The adrenergic agents can be administered individually or in any combination, together with one or more endothelin antagonist to treat hypertension.

Another aspect of the present invention is administration of centhaquin to an individual in need thereof as an analgesic to treat pain. In another aspect of the present invention, the centhaquin is coadministered with an opiate analgesic to an individual in need thereof in a treatment for pain.

Still another aspect of the present invention is administration of centhaquin to an individual in need thereof to treat resuscitative hemorrhagic shock.

Yet another aspect of the present invention is to provide an article of manufacture for human pharmaceutical use comprising (a) a package insert, (b) a container, and either (c1) a packaged composition comprising centhaquin or (c2) a packaged composition comprising an endothelin antagonist and a packaged composition comprising centhaquin. The package insert includes instructions either for treating pain or resuscitative hemorrhagic shock (c1) or for treating hypertension (c2).

These and other aspects of the present invention will become apparent from the following detailed description of the preferred embodiments of the invention.

BRIEF DESCRIPTION OF THE FIGURES

FIGS. 1A-1C contain graphs of Mean Blood Pressure (mmHz) vs. time (min), Pulse Pressure (mmHz) vs. time (min), and Heart Rate (beats/min) for administration of 10, 30, and 90 ug/kg of clonidine to rats;

FIGS. 2A-C contain graphs of Mean Blood Pressure (mmHz) vs. time (min), Pulse Pressure (mmHz) vs. time (min), and Heart Rate (beats/min) for administration of clonidine (10 μg/kg) alone and with 100, 300, or 900 μg/kg of ET-1;

FIGS. 3A-C contain graphs of Mean Blood Pressure (mmHz) vs. time (min), Pulse Pressure (mmHz) vs. time (min), and Heart Rate (beats/min) for administration of clonidine (10 μg/kg) and with TAK-044 or BMS-182874;

FIGS. 4A-C contain graphs of Mean Blood Pressure (mmHz) vs. time (min), Pulse Pressure (mmHz) vs. time (min), and Heart Rate (beats/min) for administration of clonidine (10 μg/kg) alone and with ET-1, prazosin, and centhaquin or clonodine;

FIGS. 5A-C contain graphs of Mean Blood Pressure (mmHz) vs. time (min), Pulse Pressure (mmHz) vs. time (min), and Heart Rate (beats/min) for administration of 0.05, 0.15, and 0.45 mg/kg of centhaquin;

FIGS. 6A-C contain graphs of Mean Blood Pressure (mmHz) vs. time (min), Pulse Pressure (mmHz) vs. time (min), and Heart Rate (beats/min) for administration of centhaquin (0.15 mg/kg) alone and with 100, 300, and 900 mg/kg of ET-1;

FIGS. 7A-C contain graphs of Mean Blood Pressure (mmHz) vs. time (min), Pulse Pressure (mmHz) vs. time (min), and Heart Rate (beats/min) for administration of centhaquin (0.15 mg/kg) alone and with TAK-044 or BMS182874;

FIGS. 8A-C contain graphs of Mean Blood Pressure (mmHz) vs. time (min), Pulse Pressure (mmHz) vs. time (min), and Heart Rate (beats/min) for administration of centhaquin (0.15 mg/kg) alone or with ET-1 (300 mg/kg) and prazosin (0.1 mg/kg);

FIGS. 18A-D and 19A-E contain pressure-volume loops for rats resuscitated with Ringer's lactate.

DETAILED DESCRIPTION OF THE PREFERRED EMBODIMENTS

Figure 9:
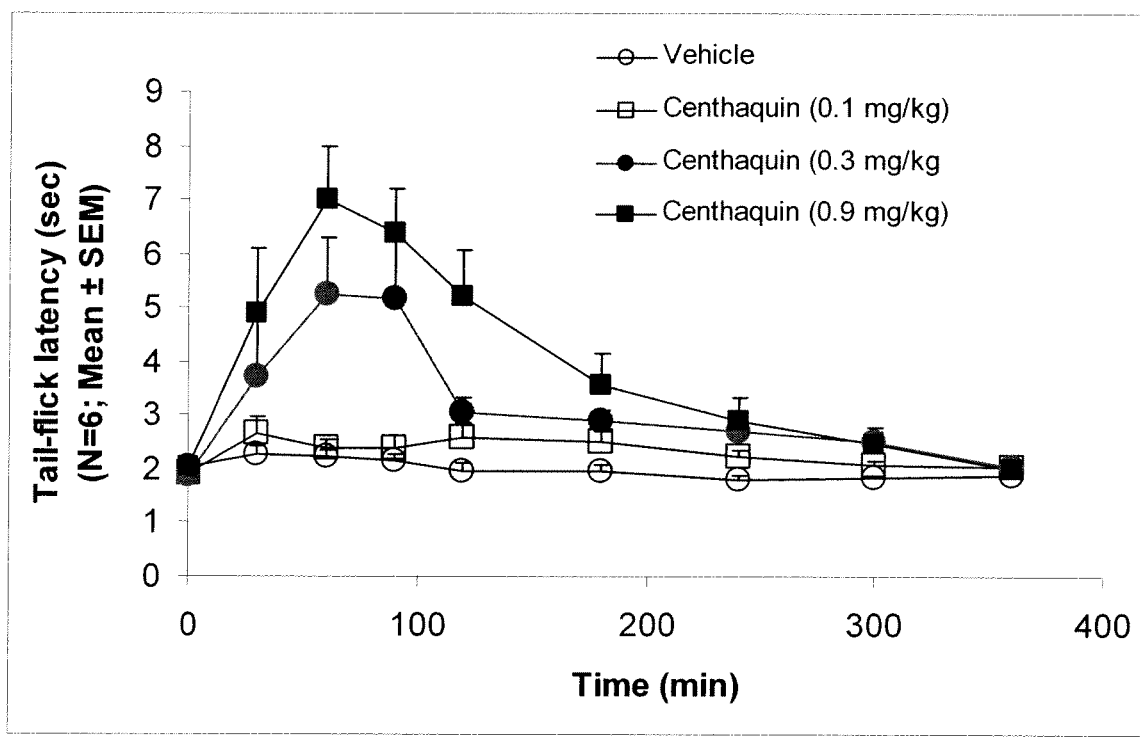
FIG. 9 contains graphs of tail-flick latency (sec) vs. time (min) for vehicle and centhaquin (0.1, 0.3, or 0.9 mg/kg)
Figure 10:
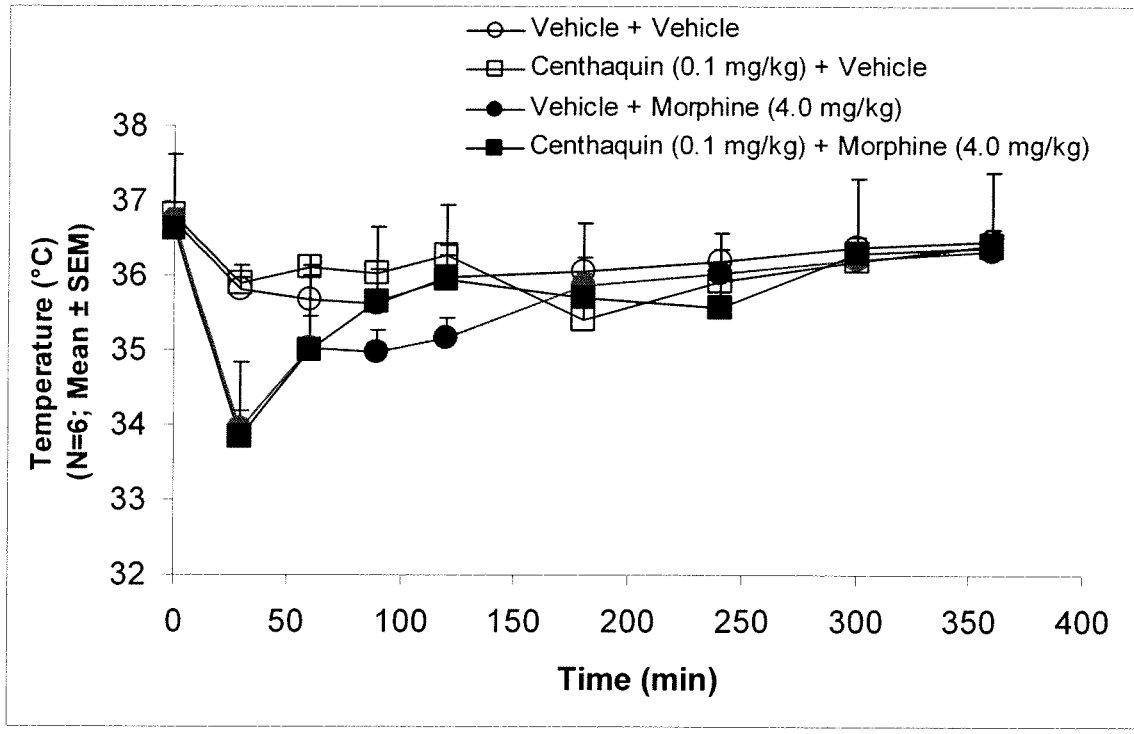
FIG. 10 contains graphs of temperature (° C.) vs. time (min) for rats treated with vehicle, centhaquin, morphine, or centhaquin and morphine.
Figure 11:
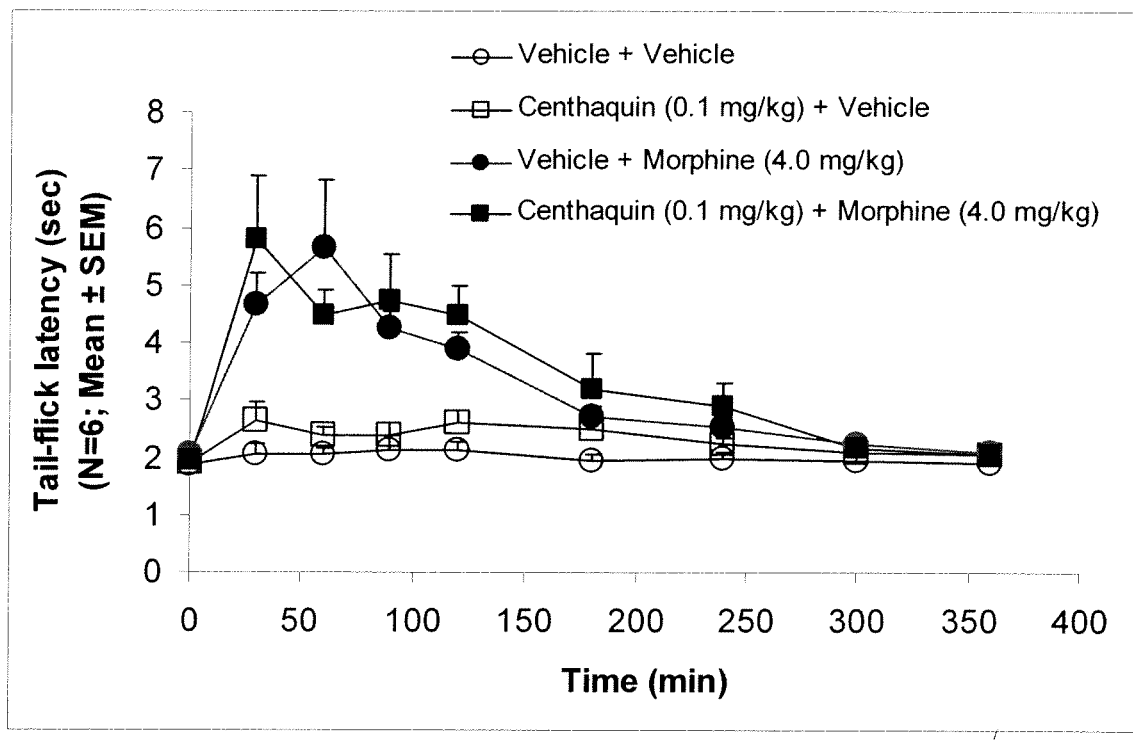
FIGS. 11-13 contain graphs of tail-flick latency (sec) vs. time (min) for rats treated with vehicle, centhaquin, morphine, or centhaquin and morphine.
Figure 12:
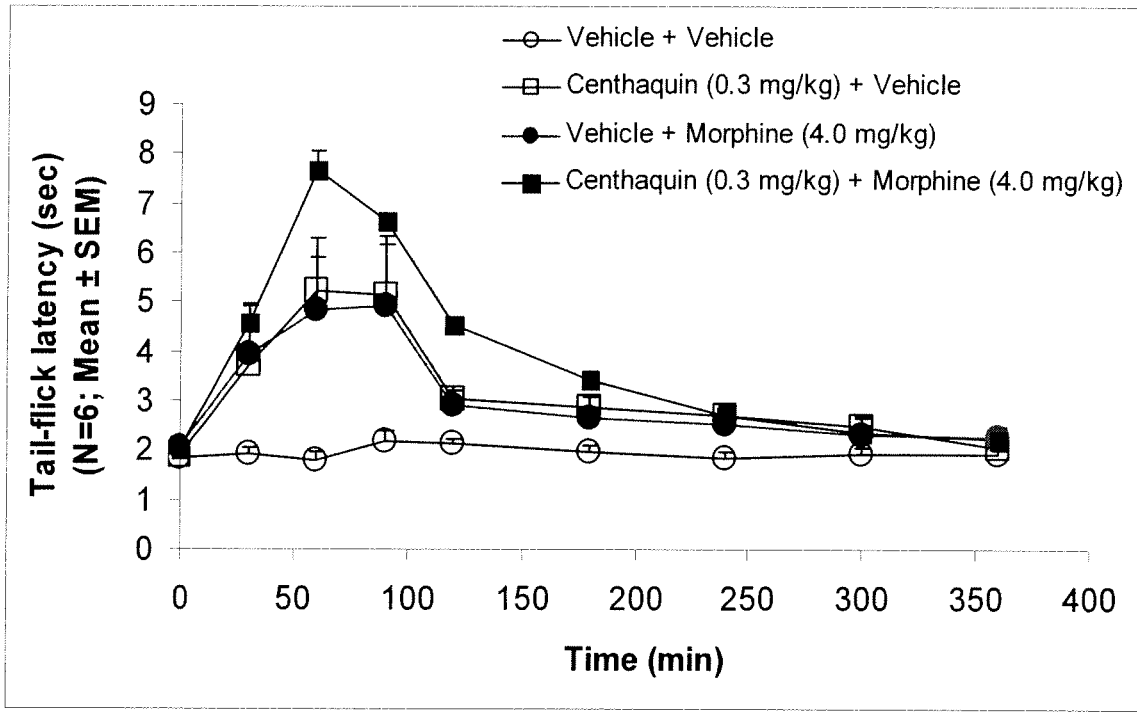
Figure 13:
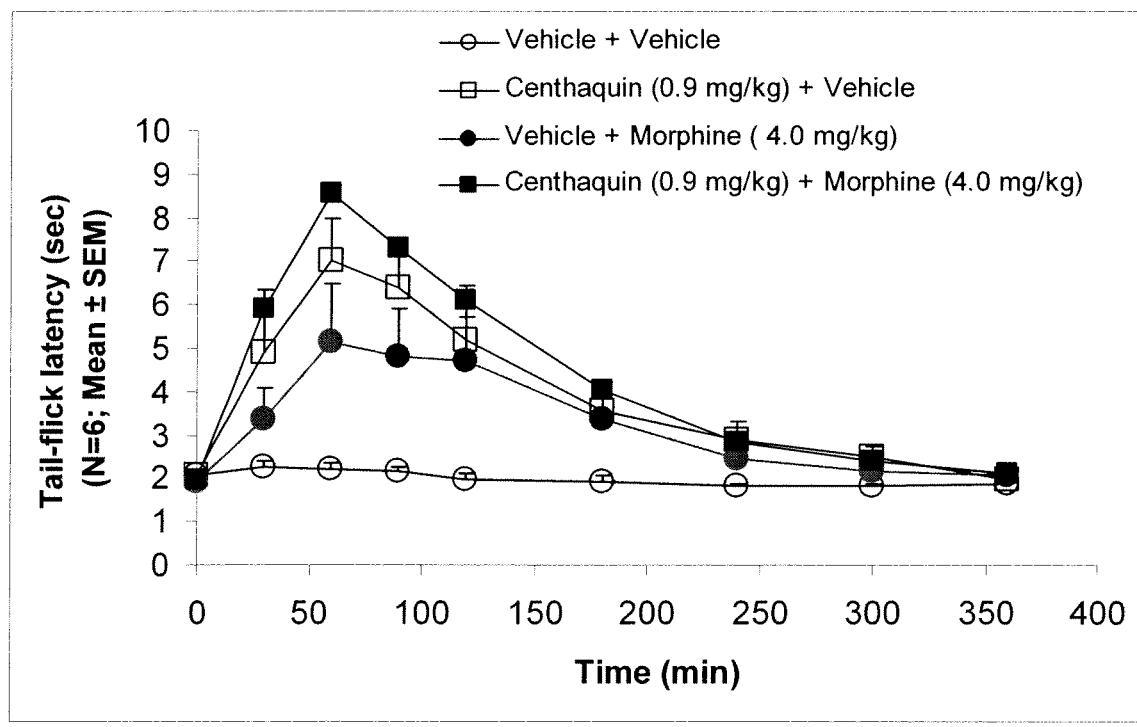

The present invention is directed to the administration of centhaquin or other adrenergic agents and an endothelin antagonist to treat hypertension. The present invention also is directed to administration of centhaquin to treat pain or resuscitative hemorrhagic shock.

The methods described herein benefit from the use of an adrenergic agent, like centhaquin, and an endothelin antagonist in the treatment of hypertension. The adrenergic agent and the endothelin antagonist can be administered simultaneously or sequentially to achieve the desired effect.

For the purposes of the invention disclosed herein, the term "treatment" includes lowering, ameliorating, or eliminating pain, hypertension, or resuscitative hemorrhagic shock, and associated symptoms of each conditions. As such, the term "treatment" includes medical therapeutic administration and, in the treatment of pain, a prophylactic administration.

The term "container" means any receptacle and closure therefore suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The term "adrenergic agent" means a compound that stimulates the sympathetic nervous system, e.g., that mimic the effects of norepinephrine and epinephrine. As used herein the term "adrenergic agent" is singular or plural.

ET is an extremely potent endothelium derived vasoconstriction factor (Hickey et al., 1985) that was isolated, sequenced, and cloned (Yanagisawa et al., 1988). Endothelins are 21 amino acid, highly potent vasoconstrictive peptides with two disulfide bonds. Endothelins are produced biologically by enzymatically cleaving preproendothelin to proendothelin, then to endothelin by endothelin-converting enzymes. ET exerts biological effects by binding to cell surface receptors, which are 7-transmembrane receptors coupled to G-proteins. There are two distinct types of endothelin receptors: (a) the ET-1 selective $ET_A$ receptors primarily found on vascular smooth muscle and responsible for vasoconstriction, and (b) nonselective $ET_B$ receptors primarily found in vascular endothelium and responsible for vasodilation.

The vasoconstrictive effects of ET-1 are mediated predominantly by G-protein coupled $ET_A$ receptors. ET-1 also is made in high concentrations by prostate, metastatic cancers, and CNS. ET in the CNS is produced by endothelial cells and nonendothelial cells, such as neurons, astrocytes, and glial cells.

The global distribution of ET and its binding sites in the brain suggests that, in addition to being a vasoconstrictor, it may be acting as an important neuropeptide in the CNS (Gulati et al., 1992). Endothelin (ET) receptor antagonists, in particular selective $ET_A$ or balanced antagonists $ET_A/ET_B$, represent a therapeutic area for diseases such as congestive heart failure (CHF) and pulmonary hypertension. BQ-123 and BMS-182874 are specific antagonists of $ET_A$ receptors (Stein et al., 1994). Endothelin antagonists have profound effects on the pulmonary vasculature and the right heart, whereas ACE inhibitors primarily affect the peripheral vessel and the left heart.

Several studies indicate that the central ET receptors are predominantly of $ET_B$ subtype. Rat cerebral astrocytes have been shown to express mainly $ET_B$ type of receptors and glial cells also were found to intensely express $ET_B$ receptor mRNA. However, the central administration of a highly selective $ET_B$ receptor agonist, IRL-1620, does not produce any effect on the cardiovascular system, and the systemic and regional circulatory effects of centrally administered ET-1 have been shown to be mediated through the $ET_A$ receptors (Gulati et al., 1995; Rebello et al., 1995).

Intracerebroventricular administration of ET-1 produces a transient rise followed by sustained fall in the mean arterial blood pressure (BP). The pressor effect was accompanied by an increase in renal sympathetic nerve activity and plasma levels of catecholamines and arginine-vasopres sin.

It also has been shown that the effects of central administration of ET-1 are mediated through activation of the sympathetic nervous system because these effects were attenuated by ganglion blockers. Intracisternal administration of ET-1 elicited a transient increase in BP, renal sympathetic nerve activity, and phrenic nerve activity. A subsequent fall in BP was accompanied by a decrease in renal sympathetic nerve activity and phrenic nerve activity. The observation that central ET-1 induced increase in pressor response was suppressed by pretreatment with phenoxybenzamine (Ouchi et al., 1989) further implicates the active participation of sympathetic nervous system in the initial pressor phase.

An endothelin antagonist utilized in the present invention can be any of the endothelin receptor antagonists known in the art. As used herein, the term "endothelin receptor antagonist" and "endothelin antagonist" are synonymous and are used interchangeably, and refer to administration of one or more of the antagonists. Endothelin is a potent vasoconstrictor. Endothelin antagonists are used to treat acute heart failure, congestive/chronic heart failure, pulmonary arterial hypertension, pulmonary edema, subarachnoid hemorrhage, chronic obstructive pulmonary disease, myocardial infarction, acute cerebral ischemia, acute coronary syndromes, acute renal failure, post-operative treatment in liver operations, and prostate cancer. No adverse effects are expected when a patient is administered an endothelin antagonist.

Preferred ET antagonists are antagonists selective for endothelin A ($ET_A$) receptors or are balanced $ET_A$/endothelin B ($ET_B$) antagonists. Such ET antagonists are set forth in Appendices A and B herein. However, endothelin B antagonists and miscellaneous endothelin antagonists, as set forth in Appendices C and D herein, also can be used in a composition or method of the present invention. Additional useful endothelin antagonists can be found in U.S. Patent Application Publication Nos. US 2002/0082285 and US 2003/0232787, and in Wu, *Exp. Opin. Ther. Patents* (2000), 10(11), pages 1653-1668, each incorporated herein by reference in its entirety.

Specific examples of endothelin antagonists useful in the present invention include, but are not limited to, atrasentan, tezosentan, bosentan, sitaxsentan, enrasentan, BMS-207940 (Bristol-Myers Squibb), BMS-193884, BMS-182874, J-104132 (Banyu Pharmaceutical), VML 588/Ro 61-1790 (Vanguard Medica), T-0115 (Tanabe Seiyaku), TAK-044 (Takeda), BQ-788, BQ123, YM-598, LU 135252, PD 145065, A-127722, ABT-627, A-192621, A-182086, TBC3711, BSF208075, S-0139, TBC2576, TBC3214, PD156707, PD180988, ABT-546, ABT-627, Z1611, RPR118031A, SB247083, SB217242, S-Lu302872, TPC10950, SB209670, and mixtures thereof.

BQ123 is a specific endothelin A antagonist, and is the sodium salt of cyclo(-D-Trp-D-Asp-Pro-D-Val-Leu-). BQ-788 is a specific endothelin B antagonist, and is the sodium salt of N-cis-2,6-dimethylpiperidinocarbonyl-L-gamma-methylleucyl-D-1-methoxycarbonyl triptophanyl-DNIe (see *Proc. Natl. Acad. Sci. USA,* 91, pp. 4892-4896 (1994)).

In addition to a conventional endothelin antagonist, a compound that inhibits the formation of endogenous endothelin also can be used as the endothelin antagonist in the present invention. Such compounds are useful because they prevent endothelin formation, and, therefore, decrease the activity of endothelin receptors. One class of such compounds is the endothelin converting enzyme (ECE) inhibitors.

Useful ECE inhibitors include, but are not limited to, CGS34225 (i.e., N-((1-((2(S)-(acetylthio)-1-oxopentyl)-amino)-1-cyclopentyl)-carbonyl-S-4-phenylphenyl-alanine methyl ester) and phosphoramidon (i.e., N-(a-rhamnopyranosyloxyhydroxyphosphinyl)-Leu-Trp).

Tests were conducted to illustrate the effects of an endothelin antagonist on an adrenergic agent, like clonidine and centhaquin, administered to a mammal, including humans. Tests also were conducted to illustrate the effects of centhaquin on analgesia and resuscitative hemorrhagic shock.

The tests and data show that a combination of an adrenergic agent, like centhaquin or clonidine, and an endothelin antagonist can be administered to mammals in methods of treating hypertension. The tests and data also show that centhaquin can be administered to mammals, alone or with an opiate analgesic, in methods of treating pain, and in methods of treating resuscitative hemorrhagic shock. The adrenergic agent and endothelin antagonist, or the centhaquin alone, can be formulated in suitable excipients for oral administration, or for parenteral administration. Such excipients are well known in the art. The active agents (e.g., centhaquin and, in some embodiments, an endothelin antagonist and adrenergic agent) typically are present in such a composition in an amount of about 0.1% to about 75% by weight, either alone or in combination.

For each of the embodiments disclosed herein, pharmaceutical compositions containing the active agents of the present invention are suitable for administration to humans or other mammals. Typically, the pharmaceutical compositions are sterile, and contain no toxic, carcinogenic, or mutagenic compounds that would cause an adverse reaction when administered.

The method of the invention can be accomplished using the active agents as described above, or as a physiologically acceptable salt or solvate thereof. The active agents, salts, or solvates can be administered as the neat compounds, or as a pharmaceutical composition containing either or both entities.

The active agents can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Administration of the active agents can be performed before, during, or after the onset of pain.

The pharmaceutical compositions include those wherein the active ingredients are administered in an effective amount to achieve their intended purpose. More specifically, a "therapeutically effective amount" means an amount effective to eliminate or to alleviate pain or hypertension. Determination of a therapeutically effective amount is well within the capability of those skilled in the art, especially in light of the detailed disclosure provided herein.

A "therapeutically effective dose" refers to the amount of the active agents that results in achieving the desired effect. Toxicity and therapeutic efficacy of such active agents can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained from such data can be used in formulating a range of dosage for use in humans. The dosage of the active agents preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amounts and intervals can be adjusted individually to provide levels of active agents that are sufficient to maintain therapeutic effects.

The amount of active agents administered is dependent on the subject being treated, on the subject's weight, the severity of the affliction, the manner of administration, and the judgment of the prescribing physician.

Specifically, for administration to a human in the curative treatment of hypertension, oral dosages of the adrenergic agent and the endothelin antagonist, individually generally are about 0.01 to about 200 mg daily for an average adult patient (70 kg), typically divided into two to three doses per day. Thus, for a typical adult patient, individual tablets or capsules contain about 0.1 to about 200 mg centhaquin and about 0.1 to about 50 mg endothelin antagonist, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The active agents of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active agents into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active agents are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% of an active agent of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active agents, and preferably about 1% to about 50% of an active agents.

When a therapeutically effective amount of the active agents is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

Suitable active agents can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active agents with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the active agents also can be formulated as a depot preparation. Such long-acting formulations can be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, the active agents can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. An active agent also can be injected parenterally, for example, intravenously, intramuscularly, subcutaneously, intrathecally, intracisternally, or intracoronarily. For parenteral administration, the active agent is best used in the form of a sterile aqueous solution which can contain other substances, for example, salts, or monosaccharides, such as mannitol or glucose, to make the solution isotonic with blood.

For veterinary use, the active agents are administered as a suitably acceptable formulation in accordance with normal veterinary practice. The veterinarian can readily determine the dosing regimen and route of administration that is most appropriate for a particular animal.

Adrenergic Agents as Centrally Acting Antihypertensive Agents

Clonidine is an antihypertensive agent that acts through central $\alpha_2$-adrenergic receptors to lower mean arterial pressure (MAP), but it also acts on peripheral $\alpha$-adrenergic receptors ($\alpha$-ARs) to produce vasoconstriction. Endothelin (ET) has been shown to modulate the action of peripheral adrenergic receptors. The present tests show the involvement of ET in the cardiovascular effects of clonidine and centhaquin. Clonidine (10, 30, and 90 µg/kg, i.v.) produced a dose-dependent fall in mean arterial pressure (MAP), pulse pressure (PP), and a decrease in heart rate (HR). Treatment with ET-1 (100, 300 and 900 ng/kg, i.v.), significantly attenuated clonidine (10 µg/kg, i.v.)-induced fall in MAP in a dose-dependent manner. In rats treated with a high dose of ET-1 (900 ng/kg, i.v.) clonidine produced 42.58% increase in MAP compared to untreated rats. Clonidine (10 µg/kg, i.v.) produced 37.42% increase in HR in rats treated with ET-1 (900 ng/kg, i.v.) compared to untreated rats. An $ET_{A/B}$ antagonist, TAK-044 (1 mg/kg, i.v.), and an $ET_A$ antagonist, BMS-182874 (9 mg/kg, i.v.), potentiated the hypotensive effect of clonidine by 17.68% and 4.81%, respectively, compared to untreated rats.

Also studied was the interaction of ET with centhaquin which produces a fall in MAP similar to clonidine. Centhaquin (0.05, 0.15, and 0.45 mg/kg, i.v.) produced a dose-dependent fall in MAP, and a decrease in HR. It did not affect arterial blood pH, $pO_2$, and $pCO_2$. Neither plasma ET-1 levels were altered. Treatment with ET-1 (100, 300, and 900 ng/kg) significantly attenuated centhaquin (0.15 mg/kg, i.v.)-induced fall in MAP in a dose-dependent manner. In rats treated with 900 ng/kg dose of ET-1, centhaquin produced 33.48% increase in MAP compared to untreated rats. Centhaquin produced 21.44% increase in HR in rats treated with ET-1 compared to untreated rats. The hypotensive effect of centhaquin was significantly potentiated in rats treated with TAK-044 (1 mg/kg) by 16.48% or BMS-182874 (9 mg/kg) by 30.67% compared to untreated rats. Centhaquin-induced bradycardia was significantly potentiated in rats treated with TAK-044 by 12.74% or BMS-182874 by 29.00% compared to untreated rats.

Prazosin, an α-adrenergic receptor antagonist, pretreatment (0.1 mg/kg, i.v.) completely blocked ET-1 induced changes in cardiovascular effects of clonidine, as well as centhaquin. It was concluded therefore that ET modulates the vascular effects adrenergic receptors leading to alterations in the cardiovascular effects of clonidine and centhaquin. This is the first showing that ET antagonists can potentiate the antihypertensive effects of clonidine and centhaquin, i.e., an adrenergic agent, by increasing the responsiveness of vascular adrenergic receptors to the constrictor effect of centhaquin. A combination of ET antagonist with clonidine or centhaquin, or other adrenergic agent, therefore is a useful option to treat hypertension.

Materials and Methods

Animals

Male Sprague-Dawley rats weighing 250 to 300 g (Harlan, Indianapolis, Ind.) were housed for at least 4 days before being used in a room with controlled temperature (23±1° C.), humidity (50±10%) and light (6:00 A.M. to 6:00 P.M.). Food and water were made available continuously. Animal care and use for experimental procedures were approved by the Institutional animal care and use committee. All anesthetic and surgical procedures were in compliance with the guidelines established by the Animal Care Committee.

Drugs and Chemicals

Centhaquin: 2-[2-(4-(3-methyphenyl)-1-piperazinyl) ethyl-quinoline (Central Drug Research Institute, Lucknow, India), clonidine, prazosin, urethane (Sigma-Aldrich St Louis, Mo., USA), BMS-182874 hydrochloride: (5-Dimethylamino)-N-(3,4-dimethyl-5-isoxazolyl)-1-naphthalene sulfonamide hydrochloride) an $ET_A$-specific antagonist (Tocris Bioscience, Ellisville, Mo., USA); TAK-044: cyclo [D-α-aspartyl-3-[(4-phenylpiperazin-1-yl) carbonyl]-L-alanyl-L-α-aspartyl-D-2-(2-thienyl)glycyl-L-leu-Cyl-D-tryptOphyljdisodium salt) an $ET_{A/B}$ non-specific antagonist (Takeda Chemical Industries, Osaka, Japan), Endothelin-1 (Research Biochemicals International, Natick, Mass., USA), Endothelin-1 Enzyme Immunometric Assay (EIA) Kit (Catalog No. 900-020A, Assay Designs, Inc., Ann Arbor, Mich., USA). Other reagents used were of the highest grade commercially available.

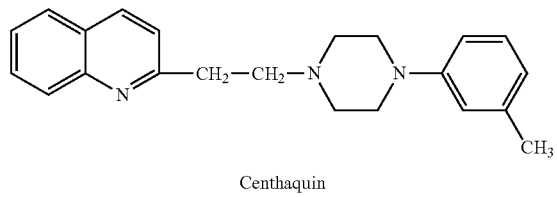

Centhaquin

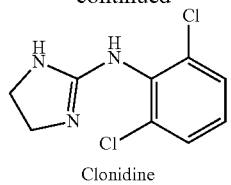

Clonidine

Determination of Cardiovascular Response of Drugs in Anaesthetized Rats

Rats were anaesthetized with urethane (1.5 g/kg i.p.) and prepared for the determination of hemodynamic parameters (Gulati and Srimal, 1993; Gulati et al., 1997b). The anesthetized rats were shaved and immobilized to prepare for cannulation. A 2-3 cm incision was made above the femoral vein and artery, and the vessels were dissected and cleaned. The left femoral vein was cannulated (PE-50 tubing, Clay Adams, Parsipanny, N.J.) and secured for drug administration. An ultra-miniature Pressure transducer SPR-320 (2F Polyurethane), with a single pressure sensor side mounted at the tip (Millar Instruments, Houston, Tex.), was inserted in the left femoral artery to acquire the hemodynamic signals. Pressure transducer was connected to bridge amplifier (ML221 Bridge Amp; AD Instruments, Mountain View, Calif., USA) with Viking connector (AEC-10C) and the signals were continuously acquired at a sampling rate of 1000 $S^{-1}$ using Millar PowerLab 16/30 data acquisition system (AD Instruments, Mountain View, Calif., USA). MAP, HR, and PP were determined and analyzed with LabChart-5.00 software program (Millar Instruments). After the experiment was completed, the animals were euthanized with higher dose of urethane (3 gm/kg).

Determination of ET-1 Level in Rat Plasma

In order to analyze the change in ET-1 level, blood samples were withdrawn after drug treatment through right femoral artery from the anaesthetized rats before and 1 h after drug treatment and were collected into chilled EDTA tubes (1 mg/ml blood) containing aprotinin (500 KIU/mL of blood). The blood samples were centrifuged at 1,600×g for 15 minutes at 0° C. and plasma separated was stored at −70° C. until analyzed. ET-1 level was estimated using Assay's Design's Endothelin-1 Enzyme Immunometric Assay Kit (Nowicki et al., 2005; Brondani et al., 2007). Briefly, plasma samples and standards were added to wells coated with a monoclonal antibody specific for ET-1. The plate then was washed after 24 hr of incubation, leaving only bound ET-1 on the plate. A solution of horseradish peroxidase (HRP) labeled monoclonal antibody to ET-1 then was added, which binds to the ET-1 captured on the plate. The plate was incubated for 30 min, then washed to remove excess HRP labeled antibody. A solution of 3,3',5,5'-tetramethylbenzidine (TMB) substrate was added which generates a blue color when catalyzed by the HRP. Hydrochloric acid (1N) was added, to stop the substrate reaction, and the resulting yellow color was read at 450 nm using DTX 800 Multimode detector. The data was analyzed with Multimode Detection Software (Beckman Coulter, Inc., Harbor Boulevard, Fullerton, Calif.). The measured optical density is directly proportional to the concentration of ET-1.

Blood Gas Analysis

Arterial blood pH, $pO_2$, $pCO_2$, $Na^+$, $K^+$, and lactate were monitored prior to and after drug administration. Blood samples were drawn from the arterial cannula using blood gas sampling syringes (Innovative Medical Technologies, Inc. Leawood, Kans.) and analyzed using a GEM Premier 3000 unit (Instrument Laboratory, Lexington, Mass.).

Determination of Clonidine Response on the Abdominal Aortic Ring

The abdominal aorta was isolated and dissected out from urethane (1.5 g·kg$^{-1}$ i.p.) anesthetized rats and was transferred to Krebs bicarbonate buffer pH 7.4 (composition in mM, NaCl, 112.0; KCl, 4.7; KH$_2$PO$_4$, 1.2; MgSO$_4$, 1.2; CaCl$_2$, 2.5; NaHCO$_3$, 25.0; glucose, 11.0) with continuous supply of 95% O$_2$ and 5% CO$_2$ at 37±1° C. The tissue was cut into ring segments (3 mm in length) and mounted in organ baths using 10 mm Radnoti glass ring supports. Extra care was taken while cutting and mounting the ring segment to prevent loss of endothelial layer. Tissue was equilibrated for 45 min by applying 2 g of tension with regular buffer change after every 15 min. Vessels were pre-contracted with 100 mM KCl to determine the viability. Clonidine-induced contractions of aortic ring were measured using Radnoti 8 unit tissue bath (Radnoti Glass Technology, Monrovia, Calif.) and the force transducer coupled with a Grass P7D polygraph. The dose response was recorded for 0.25, 0.5, 1, 2, 4, 6, 8, and 10 µM of clonidine with or without ET-1 (4 nM) treatment and ED$_{50}$ value was calculated. Experiments were performed in Group 1: Vehicle+Clonidine (0.25 to 10 µM); and Group 2: ET-1 (4 nM)+Clonidine (0.25 to 10 µM) using (n=6) rats in each group.

Determination of ET$_A$r Expression in the Brain and Abdominal Aorta

Brain and abdominal aorta isolated from vehicle and clonidine treated rats were homogenized in RIPA buffer (20 mM Tris-HCl pH 7.5, 120 mM NaCl, 1.0% Triton X100, 0.1% SDS, 1% sodium deoxycholate, 10% glycerol, 1 mM EDTA and 1× protease inhibitor, Roche). Proteins were isolated in solubilized form and concentrations were measured by Folin-Ciocalteu's phenol reagent. Solubilized protein (10 µg) was denatured in Laemmli sample buffer (Bio-Rad), resolved in 10% SDS-PAGE and transferred on nitrocellulose membrane followed by blocking of membrane with 5% BSA (w/v) in TBST (10 mM Tris, 150 mM NaCl, 0.1% Tween 20). The membranes were incubated with rabbit polyclonal anti-ETA antibodies (1:1000), followed by HRP-conjugated secondary antibodies (1:1000) and visualized by ECL Plus western blotting detection system (GE Healthcare, Buckinghamshire UK). Stripped membranes were re-probed with β-actin primary antibody (1:1000) for a protein loading control.

Study Design

The animals were allowed to stabilize for at least 20 min following surgical procedures.

Studies on Clonidine:

Following studies were performed to determine the involvement of ET in clonidine induced cardiovascular (MAP, HR, and PP) effects.

Study 1: Determine the Cardiovascular Effects of Clonidine (N=4).

Group 1: Clonidine (10 µg/kg, i.v.); Group 2: Clonidine (30 µg/kg, i.v.); and Group 3: Clonidine (90 µg/kg, i.v.)

Study 2: Determine the Effect of ET-1 on Clonidine-Induced Cardiovascular Effects (N=4).

Group 1: ET-1 (100 ng·kg$^{-1}$); Group 2: ET-1 (300 ng·kg$^{-1}$); Group 3: ET-1 (900 ng·kg$^{-1}$); Group 4: Vehicle (1 ml·kg$^{-1}$)+clonidine (10 µg·kg$^{-1}$); Group 5: ET-1 (100 ng·kg$^{-1}$)+clonidine (10 µg·kg$^{-1}$); Group 6: ET-1 (300 ng·kg$^{-1}$)+clonidine (10 µg·kg$^{-1}$); and Group 7: ET-1 (900 ng·kg$^{-1}$)+clonidine (10 µg·kg$^{-1}$).

Study 3: Determine the Effect of TAK-044 (Non Selective ET$_A$/ET$_B$ Receptor Blocker) and BMS-182874 (Selective ET$_B$ Receptor) on Clonidine-Induced Cardiovascular Effects (N=4).

Group 1: TAK-044 (1 mg·kg$^{-1}$); Group 2: BMS-182874 (9 mg·kg$^{-1}$); Group 3: Vehicle (1 ml·kg$^{-1}$)+clonidine (10 µg·kg$^{-1}$); Group 4: TAK-044 (1 mg·kg$^{-1}$)+clonidine (10 µg·kg$^{-1}$); and Group 5: BMS-182874 (9 mg·kg$^{-1}$)+clonidine (10 µg·kg$^{-1}$).

Study 4: Determine the Effect of Prazosin on ET-1 Induced Changes in Cardiovascular Responses of Clonidine (N=4)

Group 1: Vehicle (1 ml·kg$^{-1}$)+clonidine (10 µg·kg$^{-1}$); Group 2: Prazosin (0.1 mg·kg$^{-1}$)+clonidine (10 µg·kg$^{-1}$); and Group 3: ET-1 (300 ng·kg$^{-1}$)+prazosin (0.1 mg·kg$^{-1}$)+clonidine (10 µg·kg$^{-1}$).

Study 5: Determine Plasma ET-1 Level in Clonidine Treated Rats (N=4)

Group 1: Vehicle (1 ml/kg, i.v.); Group 2: Clonidine (10 µg/kg, i.v.); and Group 3: Clonidine (90 µg/kg, i.v.)

Studies on Centhaquin:

Following studies were performed to determine the involvement of ET in centhaquin induced cardiovascular (MAP, HR, and PP) effects.

Study 1: Determine the Cardiovascular Effects of Clonidine (N=5).

Group 1: Centhaquin (0.05 mg/kg, i.v.); Group 2: Centhaquin (0.15 mg/kg, i.v.); and Group 3: Centhaquin (0.45 mg/kg, i.v.)

Study 2: Determine the Effect of ET-1 on Centhaquin-Induced Cardiovascular Effects (N=4).

Group 1: ET-1 (100 ng·kg$^{-1}$); Group 2: ET-1 (300 ng·kg$^{-1}$); Group 3: ET-1 (900 ng·kg$^{-1}$); Group 4: Vehicle (1 ml·kg$^{-1}$)+centhaquin (0.15 mg·kg$^{-1}$); Group 5: ET-1 (100 ng·kg$^{-1}$)+centhaquin (0.15 mg·kg$^{-1}$); Group 6: ET-1 (300 ng·kg$^{-1}$)+centhaquin (0.15 mg·kg$^{-1}$); and Group 7: ET-1 (900 ng·kg$^{-1}$)+centhaquin (0.15 mg·kg$^{-1}$).

Study 3: Determine the Effect of TAK-044 (Non Selective ETA/ETB Receptor Blocker) and BMS-182874 (Selective ETB Receptor) on Centhaquin-Induced Cardiovascular Effects (N=4).

Group 1: TAK-044 (1 mg·kg$^{-1}$)+vehicle (1 ml·kg$^{-1}$); Group 2: BMS-182874 (9 mg·kg$^{-1}$)+vehicle (1 ml·kg$^{-1}$); Group 3: Vehicle (1 ml·kg$^{-1}$)+centhaquin (0.15 mg·kg$^{-1}$); Group 4: TAK-044 (1 mg·kg$^{-1}$)+centhaquin (0.15 mg·kg$^{-1}$); and Group 5: BMS-182874 (9 mg·kg$^{-1}$)+centhaquin (0.15 mg·kg$^{-1}$).

Study 4: Determine the Effect of Prazosin on ET-1 Induced Changes in Cardiovascular Responses of Centhaquin (N=4)

Group 1: Vehicle (1 ml·kg$^{-1}$)+centhaquin (0.15 mg·kg$^{-1}$); Group 2: Prazosin (0.1 mg·kg$^{-1}$)+centhaquin (0.15 mg·kg$^{-1}$); and Group 3: ET-1 (300 ng·kg$^{-1}$)+prazosin (0.1 mg·kg$^{-1}$)+centhaquin (0.15 mg·kg$^{-1}$).

Study 5: Determine Plasma ET-1 Level in Centhaquin Treated Rats (N=4)

Group 1: Vehicle (1 ml/kg, i.v.); Group 2: centhaquin (0.15 mg/kg, i.v.); and Group 3: centhaquin (0.45 mg/kg, i.v.)

In the above studies, all drugs were injected through the left femoral vein and changes in MAP, HR, and PP after clonidine and centhaquin injection were recorded for 1 hour using Millar PowerLab 16/30 data acquisition system.

Statistical Analysis of Data

Data are presented as mean±S.E.M. The significance of differences was estimated by one-way analysis of variance (intra group comparison with respect to base line data) and two-way analysis of variance (inter group comparison with respect to corresponding time points from each groups)

followed by application of the Dunnett's Multiple Comparisons and Bonferroni test respectively. A P value of less than 0.05 was considered to be significant. The statistical analysis was processed with GraphPad Prism software Version 5.00.
Results
Effect of Clonidine and Centhaquin on Arterial Blood Gases Arterial blood pH, $pO_2$, $pCO_2$, $Na^+$, $K^+$, lactate, and hematocrit were monitored before and one hour after administration of clonidine (90 µg/kg) and centhaquin (0.45 mg/kg), and it was found that there was no significant changes in these parameters with either clonidine or centhaquin (Table 1). Blood samples were drawn from the arterial cannula using blood gas sampling syringes (Innovative Medical Technologies, Inc. Leawood, Kans.) and analyzed using a GEM Premier 3000 unit (Instrument Laboratory, Lexington, Mass.).

Table 1 summarizes arterial blood pH, $pO_2$, $pCO_2$, $Na^+$, $K^+$, lactate, and hematocrit levels before and after administration of clonidine (90 µg/kg) and centhaquin (0.45 mg/kg). It was found that there were no significant changes in these parameters with either clonidine or centhaquin

| Treatment | pH | $pCO_2$ (mmHg) | $pO_2$ (mmHg) | $Na^+$ (mmol/L) | $K^+$ (mmol/L) | Lactate (mg/dL) | Hct (%) |
|---|---|---|---|---|---|---|---|
| Baseline | 7.28 ± 0.02 | 47 ± 3 | 114 ± 3 | 140 ± 2 | 3.6 ± 0.2 | 2.42 ± 0.32 | 46 ± 2 |
| Clonidine | 7.28 ± 0.03 | 46 ± 4 | 100 ± 14 | 139 ± 2 | 4.3 ± 0.6 | 1.35 ± 0.25 | 50 ± 4 |
| Baseline | 7.30 ± 0.03 | 47 ± 4 | 104 ± 1 | 144 ± 3 | 3.5 ± 0.3 | 2.42 ± 0.17 | 46 ± 2 |
| Centhaquin | 7.27 ± 0.02 | 53 ± 2 | 96 ± 9 | 140 ± 1 | 4.0 ± 0.2 | 1.25 ± 0.55 | 52 ± 1 |

Involvement of ET in Clonidine-Induced Cardiovascular Effects
Dose-Dependent Cardiovascular Effects of Clonidine Clonidine administered intravenously produced a significant decrease in MAP. Lower doses of clonidine (10 µg/kg) produced a fall in MAP of 24.02% (p<0.01; compared to baseline), while a dose of 30 µg/kg dose produced a fall in MAP of 26.15% (p<0.01; compared to baseline). The fall in MAP was 19.48% (p<0.01; compared to baseline) with 90 µg/kg dose of clonidine. The fall in MAP induced by clonidine with 10 and 30 µg/kg dose was significantly (p<0.01) more than that induced by 90 µg/kg dose of clonidine (FIG. 1A).

Administration of clonidine produced a significant reduction in PP. The decrease in PP was 33.81% with 10 µg/kg, 36.39% with 30 µg/kg, and 34.27% with 90 µg/kg dose of clonidine. The decrease in PP was statistically significant (p<0.01) compared to respective baseline. The decrease in PP was similar with all the doses of clonidine (FIG. 1B).

Clonidine produced a decrease in HR. A dose of 10 µg/kg produced a decrease in HR of 20.84%, while 30 µg/kg produced 23.18% decrease, and 90 µg/kg produced a 23.19% decrease. Clonidine induced bradycardia was similar with all the doses (FIG. 1C).

Effect of ET-1 on Clonidine Induced Cardiovascular Effects

In these experiments, a low dose of clonidine (10 µg/kg) was used and it was found that in rats treated with ET-1 (100, 300, or 900 ng/kg), the fall in MAP normally induced by clonidine was not observed. ET-1 (100 ng/kg) treatment significantly attenuated clonidine induced fall in MAP. The maximal attenuation was 27.63% (p<0.01) compared to vehicle treated rats receiving clonidine. Similarly, 300 ng/kg dose of ET-1 produced an attenuation of clonidine-induced decrease in MAP by 27.41% when compared to vehicle treated rats receiving clonidine. ET-1 treatment in the dose of 900 ng/kg produced significant attenuation (42.58%; p<0.001) of clonidine-induced decrease in MAP, compared to vehicle treated rats receiving clonidine. Statistical analysis showed that the attenuation of clonidine-induced decrease in MAP was similar in rats treated with different doses (100, 300, and 900 ng/kg) of ET-1 (FIG. 2A).

Clonidine-induced decrease in PP was attenuated by treatment with ET-1. The dose of 100 ng/kg of ET-1 was most effective in attenuating (33.66%) clonidine induced fall in PP and was found to be statistically significant (p<0.01). However, the doses of 300 and 900 ng/kg showed attenuation, but did not reach the level of statistical significance (FIG. 2B).

Rats treated with ET-1 (100, 300, or 900 ng/kg) when injected with clonidine did not show any significant reduction in HR compared to baseline. ET-1 treatment in the dose of 100 ng/kg showed 18.01% attenuation of clonidine-induced decrease in HR, while 300 ng/kg dose of ET-1 showed 21.00% attenuation and 900 ng/kg dose of ET-1 produced 37.42% (p<0.001) attenuation of HR compared to vehicle treated rats receiving clonidine (FIG. 2C).

Effect of ET Antagonists on Clonidine Induced Cardiovascular Effects

Rats treated with an $ET_A/ET_B$ receptor antagonist, TAK-044 (1 mg/kg), or an $ET_A$ receptor antagonist, BMS-182874 (9 mg/kg), when injected with clonidine (10 µg/kg) showed significant reduction in MAP by 36.59% and 29.44%, respectively when compared with the baseline. In rats treated with TAK-044, clonidine produced a maximal decrease of 17.68% (p<0.05) in MAP compared to vehicle treated rats receiving clonidine. However, in rats treated with BMS-182874, clonidine produced a maximal decrease of 4.81% in MAP compared to vehicle treated rats receiving clonidine (FIG. 3A).

Rats treated with TAK-044 or BMS-182874, when injected with clonidine, showed significant reduction in PP and a maximum decrease of 52.72% and 44.97%, respectively, compared to baseline. In rats treated with TAK-044, clonidine produced a maximal decrease of 31.42%, while those treated with BMS-182874 produced a 17.06% decrease in PP compared to vehicle treated rats receiving clonidine. The decrease in PP in TAK-044 treated rats was significantly more compared to those treated with BMS-182874 (FIG. 3B).

Clonidine produced a decrease in HR which was similar in rats treated with TAK-044 or BMS-182874. In rats treated with TAK-044, clonidine produced a maximal decrease of 8.83% in HR when compared to vehicle treated rats receiving clonidine. In rats treated with BMS-182874, clonidine produced a maximal decrease of 5.85% in HR when compared to vehicle treated rats receiving clonidine (FIG. 3C). Rats treated with TAK-044 (1 mg/kg) or BMS-182874 (9 mg/kg) alone showed no significant change in MAP, PP, and HR (FIGS. 3A, 3B, and 3C).

Effect of Prazosin on ET-1 Induced Changes in Cardiovascular Responses of Clonidine In rats treated with ET-1 (300 ng/kg) and prazosin (0.1 mg/kg), clonidine produced no change in MAP compared to baseline. Prazosin completely blocked the changes produced in MAP by clonidine in ET-1 treated rats (FIG. 4A).

Similarly, in rats treated with ET-1 and prazosin, clonidine produced no change in PP compared to baseline. Prazosin significantly attenuated the decrease in PP induced by clonidine in ET-1 treated rats (FIG. 4B).

In rats treated with ET-1 and prazosin, clonidine produced no significant change in HR compared to baseline. Prazosin significantly ($p<0.05$) attenuated the decrease in HR induced by clonidine in ET-1 treated rats (FIG. 4C).

Plasma ET-1 Level in Rats Treated with Clonidine

The plasma levels of ET-1 at baseline was found to be 12.18±0.42 pg/ml and after 1 hour of vehicle treatment plasma ET-1 levels were found to be 11.97±1.29 pg/ml. In rats treated with clonidine 10 μg/kg, baseline line ET-1 levels were 12.39±0.62 pg/ml and 1 hour of treatment did not produce any change in plasma ET-1 level (13.45±0.68 pg/ml). Similarly, in rats treated with a high dose of clonidine (90 μg/kg) the baseline ET-1 levels were 12.59±0.77 pg/ml and clonidine treatment did not produce any significant effect on plasma ET-1 levels (11.31±0.92 pg/ml).

Effect of Clonidine on Abdominal Aortic Ring

Clonidine produced a dose-dependent (0.25-10 μM) contraction in rat abdominal aortic ring, while in ET-1 pretreated aorta the contractile response of clonidine was significantly potentiated ($p<0.001$). The percent contraction of aorta produced by clonidine (2 μM), in vehicle and ET-1 (4 nM) treated aorta, was 51.017±1.70% and 75.95±1.36%, respectively, while with 4 μM dose of clonidine, the percent contraction in vehicle and ET-1 treated aorta was 80.27±2.48% and 96.83±0.54%, respectively. The $ED_{50}$ value of clonidine was 2.64±0.02 μM in vehicle treated aorta, while in ET-1 treated aorta the $ED_{50}$ value of clonidine was 1.81±0.04 μM, indicating a significant potentiation ($p<0.001$) of clonidine response by ET-1.

Involvement of ET in Centhaquin Induced Cardiovascular Effects

Dose-Dependent Cardiovascular Effects of Centhaquin

Centhaquin administered intravenously to rats, produced significant dose-dependent decrease in MAP. The doses of 0.05 mg·kg$^{-1}$, 0.15 mg·kg$^{-1}$, and 0.45 mg·kg$^{-1}$ centhaquin produced significant decrease of 15.64, 25.15, and 28.08% ($p<0.001$), respectively, compared to baseline. The decrease in MAP produced by 0.15 or 0.45 mg·kg$^{-1}$ doses was more significant compared to 0.05 mg·kg$^{-1}$ dose (FIG. 5A).

Rats administered with 0.05 mg·kg$^{-1}$, 0.15 mg/kg, and 0.45 mg·kg$^{-1}$ doses of centhaquin showed 10.49, 12.57, and 13.34% ($p<0.01$) reduction in HR, respectively, compared to baseline (FIG. 5B).

Effect of ET-1 on Centhaquin Induced Cardiovascular Effects

Rats treated with 100, 300, and 900 ng·kg$^{-1}$ doses of ET-1 showed a fall ($p<0.001$) followed by significant rise ($p<0.001$) in MAP (FIG. 6A), while no change in HR (FIG. 6B) was observed compared to baseline. A middle dose of 0.15 mg·kg$^{-1}$ of centhaquin was used for subsequent studies. Lower doses of ET-1 (100 and 300 ng·kg$^{-1}$) showed a small statistically insignificant attenuation of centhaquin-induced decrease in MAP, while a higher dose of 900 ng·kg$^{-1}$ showed significant (33.48%; $p<0.001$) attenuation of centhaquin-induced decrease in MAP compared to vehicle treated rats receiving centhaquin (FIG. 7A).

Administration of centhaquin (0.15 mg·kg$^{-1}$) produced a decrease in HR. The decrease in HR produced by centhaquin was similar in rats treated with vehicle or 100 ng·kg$^{-1}$ dose of ET-1. However, in rats treated with higher dose (300 ng·kg$^{-1}$) of ET-1, centhaquin-induced decrease in HR was significantly attenuated. The dose of 900 ng/kg of ET-1 produced a marked attenuation of 21.44% ($p<0.001$) in centhaquin-induced decrease in HR compared to vehicle treated rats receiving centhaquin (FIG. 7B).

Effect of ET Antagonists on Centhaquin Induced Cardiovascular Effects

Centhaquin (0.15 mg/kg) produced a decrease in MAP. However, in rats treated with the $ET_A/ET_B$ receptor antagonist TAK-044 (1 mg/kg), centhaquin produced a marked decrease of 32.31% ($p<0.01$) in MAP compared to baseline. In rats treated with the $ET_A$ receptor antagonist BMS-182874 (9 mg/kg), centhaquin produced even more significant decrease of 43.46% ($p<0.001$) in MAP compared to baseline. It was found that treatment with TAK-044 produced potentiation of centhaquin effect by 16.48% ($p>0.05$), while treatment with BMS-182874 produced a potentiation of 30.67% ($p<0.001$) compared to vehicle treated rats (FIG. 7A).

Centhaquin produced a decrease in PP. In rats treated with TAK-044, centhaquin produced a decrease in PP by 46.49% ($p<0.001$) compared to baseline. In rats treated with BMS-182874, centhaquin produced a decrease in PP by 49.68% ($p<0.001$) compared to baseline. The decrease in PP induced by centhaquin was similar in TAK-044 and BMS-182874 treated rats (FIG. 7B).

A decrease in HR was produced by centhaquin administration. In rats treated with TAK-044, centhaquin produced a decrease in HR by 21.94%, compared to baseline. However, in rats treated with BMS-182874, centhaquin produced a decrease in HR by 35.72% ($p<0.001$), compared to baseline. It was found that TAK-044 produced potentiation of centhaquin-induced decrease in HR by 12.74%, while BMS-182874 produced potentiation by 29.00% ($p<0.001$) in HR compared to vehicle treated rats. Potentiation of centhaquin induced decrease in HR by BMS-182874 was significantly more than that produced by TAK-044 treatment by 18.63% ($p<0.05$) (FIG. 7C). Rats treated with TAK-044 (1 mg/kg) or BMS-182874 (9 mg/kg) alone showed no significant change in MAP and HR (FIGS. 7A and 7B).

Effect of Prazosin on ET-1 Induced Changes in Cardiovascular Responses of Centhaquin In rats treated with ET-1 (300 ng/kg) and prazosin (0.1 mg/kg), centhaquin produced no change in MAP compared to baseline. Prazosin completely ($p<0.01$) blocked the changes produced in MAP by centhaquin in ET-1 treated rats (FIG. 8A).

Similarly, in rats treated with ET-1 and prazosin, centhaquin produced no change in PP compared to baseline. Prazosin significantly ($p<0.001$) attenuated the decrease in PP induced by centhaquin in ET-1 treated rats (FIG. 8B).

In rats treated with ET-1 and prazosin, centhaquin produced no significant change in HR compared to baseline. Prazosin significantly ($p<0.05$) attenuated the decrease in HR induced by centhaquin in ET-1 treated rats (FIG. 8C).

Prazosin also blocked the changes in MAP and HR provided by centhaquin in vehicle treated rats (FIGS. 8A and 8B).

Plasma ET-1 Level in Rats Treated with Centhaquin

The baseline plasma ET-1 levels were 12.18±0.42 pg/ml, and after 1 hour of vehicle treatment were 11.97±1.29 pg/ml. The plasma ET-1 levels did not show any change in vehicle treated rats. In rats treated with centhaquin (0.15 mg/kg), baseline ET-1 levels were 10.89±1.77 pg/ml and 1 hour of treatment did not produce any change in plasma ET-1 level (10.39±1.75 pg/ml). Similarly, in rats treated with a high dose of centhaquin (0.45 mg/kg), the baseline ET-1 levels were 11.83±1.04 pg/ml and centhaquin treatment did not produce any significant effect on plasma ET-1 level (11.67±1.41 pg/ml).

The present disclosure illustrates the interaction of ET agonists and antagonists with central acting antihypertensive drugs, clonidine and centhaquin.

Clonidine is an antihypertensive drug, which acts by stimulating α-adrenergic receptors in the brain (Schmitt, 1969; U'Prichard et al., 1977; Kobinger, 1978) leading to decrease in cardiac output, peripheral vascular resistance and blood pressure. It has specificity towards the presynaptic $\alpha_2$-adrenergic receptors in the vasomotor center in the brainstem (Schmitt, 1969; Kobinger, 1978). This decreases presynaptic calcium levels, and inhibits the release of norepinephrine and the net effect is a decrease in sympathetic tone (Langer et al., 1980; van Zwieten et al., 1984; Chen et al., 1994). Clonidine also has peripheral $\alpha_1$-adrenergic agonistic activity, which may produce transient vasoconstriction and hypertension when administered systemically in higher doses. It has an approximately 10-fold higher binding affinity for the $\alpha_2$-adrenergic receptors than the $\alpha_1$-adrenergic receptors, both in binding assays and in isolated organs (U'Prichard et al., 1977). The hypotensive effect of clonidine is mediated through the stimulation of $\alpha_2$-adrenergic receptors (Kobinger, 1978; Guyenet and Cabot, 1981), while centhaquin was administered, a marked hypertensive effect was produced such that their central hypotensive effect was masked and was not observed.

In order to confirm the involvement of endogenous ET in the modulation of peripheral adrenergic receptors studies were carried out using ET antagonists. Two different ET antagonists were used: TAK-044 (non-selective $ET_A/ET_B$ receptor blocker) (Ikeda et al., 1994) and BMS-18287 (selective $ET_A$ receptor blocker) (Stein et al., 1994). Rats pretreated with TAK-044 and BMS-182874 showed potentiation of the hypotensive effect of clonidine or centhaquin, indicating the involvement of endogenous ET in the peripheral hypertension caused by clonidine. The potentiation was found to be more prominent with TAK-044 compared to BMS-182874, indicating the possible involvement of $ET_B$ receptors in clonidine-induced peripheral effects (Table 2). Prazosin treatment also was used to determine whether α-adrenergic receptors are involved in ET-1 potentiation of clonidine- or centhaquin-induced cardiovascular effects. Rats treated with ET-1 and prazosin when injected with clonidine showed complete blockage of ET-1 induced attenuation of clonidine response, confirming that this effect is mediated through peripheral α-adrenergic receptors.

Table 2 summarizes the effect of non-selective $ET_A/ET_B$ receptor antagonist TAK-044 and selective $ET_A$ receptor antagonist BMS182874 on clonidine (10 μg/kg) and centhaquin (0.33 mg/kg) induced changes in mean arterial pressure, pulse pressure, and heart rate. A percent change is expressed compared to clonidine or centhaquin response in control rats.

|  | Hypotension | | Decrease in pulse pressure | | Bradycardia | |
| --- | --- | --- | --- | --- | --- | --- |
|  | Clonidine | Centhaquin | Clonidine | Centhaquin | Clonidine | Centhaquin |
| TAK-044 | ++ (17.68%) | ++ (16.48%) | ++++ (31.42%) | +++ (23.83%) | + (8.83%) | ++ (12.74%) |
| BMS-182874 | + (4.81%) | ++++ (30.67%) | ++ (17.06%) | +++ (28.72%) | + (5.85%) | ++++ (29.00%) | the hypertensive effect is due to the vasoconstriction caused by stimulation of peripheral $\alpha_1$-adrenergic receptors (Timmermans and Van Zwieten, 1980; Bousquet and Schwartz, 1983).

Although structurally different from clonidine, centhaquin produces a fall in MAP and HR similar to that seen with clonidine in anesthetized cats and rats (Srimal et al., 1990). Centhaquin, like clonidine, is thought to act mainly on the central $\alpha_2$-adrenoreceptors. Upon chronic administration in rats, both centhaquin and clonidine produced hypotension and bradycardia associated with an up-regulation in α-adrenergic receptors in the hypothalamus and medulla (Gulati et al., 1991a; Gulati et al., 1991b).

Clonidine or centhaquin administered intravenously produced a dose-dependent hypotension and bradycardia. Treatment with ET-1 completely attenuated clonidine- and centhaquin-induced hypotension and bradycardia. In rats treated with a high dose of ET-1, hypertension and tachycardia was observed when clonidine or centhaquin were administered. This attenuation of clonidine or centhaquin effect by ET-1 could be due to enhanced sensitization of peripheral adrenergic receptors resulting in functional blockage of hypotension induced by clonidine (Gulati and Srimal, 1993) or centhaquin. It can be theorized, but not relied upon, that ET-1 treatment increased the sensitivity of peripheral α-adrenergic receptors to the extent that, when clonidine or The involvement of peripheral adrenergic receptors in the modulation of clonidine effect by ET-1 has been demonstrated earlier by studies conducted in cervical sectioned rats where clonidine given intravenously did not produce any effect on blood pressure and heart rate indicating that due to cervical sectioning clonidine is not able to produce its action on CNS. However, significant hypertensive response was obtained when clonidine was administered following ET-1 treatment in cervical sectioned rats (Gulati and Srimal, 1993). These results confirmed the involvement of peripheral vascular system in the hypertensive effect of clonidine in ET-1 treated rats.

The present results are supported by studies showing that ET-1 is an important modulator of vasomotor tone and it has been demonstrated that ET-1 is capable of amplifying the contractile response of several vasoactive compounds (Consigny, 1990; Nakayama et al., 1991; Gondre and Christ, 1998). Cross-talk between $ET_A$ receptors and $\alpha_1$-adrenergic receptors has been reported. In rat fibroblasts transfected with hamster $\alpha_1$-adrenergic receptors, activation of $ET_A$ receptors resulted in $\alpha_1$-adrenergic receptor phosphorylation and inhibition of $\alpha_1$-adrenergic receptor activations (Vazquez-Prado et al., 1997; D'Angelo et al., 2006). The modulator role of endothelium in α-adrenergic agonist-induced vasoconstriction has been shown, because removal of endothelium enhanced the sensitivity and maximal contractile response to adrenergic agonists showing involvement of nitric oxide (Carrier and White, 1985). Results of the present study conducted in vivo clearly demonstrate that ET-1 alters the responses of adrenergic drugs, e.g., clonidine and centhaquin, by potentiating the peripheral vasoconstriction mediated via adrenergic receptors. Although clonidine is acting mainly on $\alpha_2$-adrenergic receptors and less on $\alpha_1$-adrenergic receptors, studies have shown that prazosin (an $\alpha_1$-adrenergic receptor antagonist) blocks clonidine-induced contractions of the tail artery (Kennedy et al., 2006). This supports the finding that modulation of clonidine- and centhaquin-induced cardiovascular responses by ET-1 could be completely blocked by prazosin. Involvement of $\alpha_1$-adrenergic receptors is further supported by studies where it was found that these receptors mediate contractile responses to norepinephrine in femoral artery (Jarajapu et al., 2001). Vascular ring preparations of the rabbit ear artery and rat thoracic aorta showed that subtypes of $\alpha_1$-adrenergic receptors are involved in the contractions (Fagura et al., 1997). A recent study shows that there is an increase in sympathetic drive and reduced parasympathetic activity followed 7 day treatment with a non-selective $ET_A/ET_B$ receptor antagonist, bosentan, (Souza et al., 2008) indicating that endogenous ET plays an important role in autonomic control.

It is interesting to note that a non-selective $ET_A/ET_B$ receptor antagonist, TAK-044, was significantly more effective in potentiating clonidine-induced hypotension and bradycardia compared to centhaquin. On the other hand, a selective $ET_A$ receptor antagonist, BMS-182874 was more effective in potentiating the centhaquin-induced hypotension and bradycardia compared to clonidine. Furthermore, TAK-044 produced more or less similar potentiation of MAP, PP, and HR responses of clonidine and centhaquin, while BMS-182874 produced significantly more marked potentiation of centhaquin effect on MAP, PP and HR compared to clonidine (Table 2). These results indicate that in addition to $\alpha_1$-adrenergic receptors other receptors also may be playing a role, and that the mechanism of action of clonidine and centhaquin is different. This also supports the involvement of $ET_A$ rather than $ET_B$ receptors in the modulation of cardiovascular effects of adrenergic drugs by ET.

Other receptors also may be involved because it has been found that repeated administration of clonidine or centhaquin produced up-regulation of $5-HT_1$ receptors in the medulla (Gulati et al., 1991a; Gulati et al., 1991b) indicating that both centhaquin and clonidine also may be acting on $5-HT_1$ receptors. Several reports have shown that threshold or near threshold concentrations of ET-1 potentiate contractile response to other vasoactive agents like 5-HT (Consigny, 1990; Nakayama et al., 1991). Clonidine or centhaquin treatment did not produce any change in plasma ET-1 levels, it is more likely that there is an interaction of ET receptors with adrenergic receptors.

When clonidine is administered to a patient with intact autonomic function, a transient rise in blood pressure results, followed by a sustained fall in blood pressure and, in order for clonidine to be effective in lowering blood pressure, autonomic integrity is a necessity (Naftchi and Richardson, 1997). In patients with the injury of the spinal cord, the peripherally acting effects of clonidine and centhaquin may dominate leading to vasoconstriction and hypertension (Backo et al., 2002). In such cases, use of an ET antagonist along with an adrenergic agent, e.g., clonidine or centhaquin, may be a useful therapeutic option to prevent adverse effects.

Cases of clonidine intoxication have been reported (Pal and Lipsitz, 1976), and the symptoms of intoxication generally result from the central action of clonidine, although hypertension complicating the over dosage has also been reported (Kobinger and Walland, 1967; Hunyor et al., 1975). A case of hypertensive emergency was reported in a patient maintained with clonidine and mirtazepine prescribed concurrently (Abo-Zena et al., 2000). A possible speculative mechanism of this interaction and hypertensive urgency is that clonidine exerts its antihypertensive effect through agonist activity at central $\alpha_2$-adrenergic inhibitory receptors and the antidepressant mirtazepine acts as an antagonist at the same $\alpha_2$-adrenergic receptors (Troncoso and Gill, 2004). At a high dose, it displaces clonidine, leading to a possible loss of antihypertensive effect. The additional rebound hypertension of clonidine withdrawal appears to exacerbate the prior hypertensive state. It may be speculated that in such cases ET antagonists may be of use to reduce the adverse effects of clonidine.

It has been found that ET can modulate the cardiovascular effects mediated through vascular adrenergic receptors. This is the first report showing that ET antagonists can potentiate the antihypertensive effects of clonidine and centhaquin. An ET antagonist can therefore be useful in the treatment of toxic effects due to an overdose of clonidine. Since two ET antagonists already in US market for the treatment of pulmonary hypertension, and several are in pipeline, it may important to explore the interaction of these agents with other antihypertensive drugs acting on the adrenergic system. Because the use of clonidine is limited due to its adverse effects, a combination of ET antagonist with clonidine or centhaquin can be a useful option to treat hypertension.

Table 3 summarizes the proposed mechanism by which ET-1 and ET receptor antagonist modulate clonidine- and centhaquin-induced changes in mean arterial pressure. Clonidine and centhaquin act on central as well as peripheral adrenergic receptors. Stimulation of (a) peripheral receptors produces vasoconstriction, and (b) central receptors decreases the sympathetic drive producing vasodilatation, the net result is fall in blood pressure because central effect dominates over the peripheral effect. Treatment with ET-1 markedly increases the peripheral vasoconstrictor effect and now the peripheral effect dominates over the central and net result is an increase in blood pressure. However, treatment with ET antagonist decreases the peripheral vasoconstrictor effect, therefore the central effect over dominates and the net result is a marked hypotensive effect.

| Treatment | Mean Arterial Pressure | | |
|---|---|---|---|
| | Central Vasodilatation | Peripheral Vasoconstriction | Change in blood pressure |
| None | +++ | + | ↓↓ |
| ET-1 | +++ | ++++ | ↑ |
| ET antagonist | +++ | − | ↓↓↓↓ |

FIG. 1 shows the cardiovascular effects of clonidine (10, 30, and 90 μg/kg) in urethane anaesthetized rats. Dose-response effect of clonidine was recorded for 60 minutes and values for MAP (FIG. 1A), PP (FIG. 1B), and HR (FIG. 1C) are expressed as mean±SEM with n=4 in each group. *p<0.05 compared to baseline and # p<0.05 compared to 10 μg/kg dose of clonidine.

FIG. 2 shows the effect of ET-1 (100, 300 and 900 ng/kg) treatment on clonidine-induced cardiovascular responses in urethane anaesthetized rats. The MAP (FIG. 2A), PP (FIG. 2B), and HR (FIG. 2C) was recorded for 60 minutes after clonidine (10 µg/kg) administration, and the values are expressed as mean±SEM with n=4 in each group. *p<0.05 compared to baseline and # p<0.05 compared to 10 µg/kg dose of clonidine.

FIG. 3 shows the effect of the non-selective $ET_A/ET_B$ receptor antagonist TAK-044 (1 mg/kg) and the selective $ET_A$ receptor antagonist BMS-182874 (9 mg/kg) treatment on clonidine-induced cardiovascular responses in urethane anaesthetized rats. The MAP (FIG. 3A), PP (FIG. 3B), and HR (FIG. 3C) was recorded for 60 minutes after clonidine (10 µg/kg) administration, and the values are expressed as mean±SEM with n=4 in each group. *p<0.05 compared to baseline and # p<0.05 compared to 10 µg/kg dose of clonidine.

FIG. 4 shows the effect of prazosin (0.1 mg/kg) on ET-1 (300 ng/kg) induced changes in cardiovascular responses of clonidine (10 µg/kg) in urethane anaesthetized rats. The MAP (FIG. 4A), PP (FIG. 4B), and HR (FIG. 4C) was recorded for 60 minutes after clonidine (10 µg/kg) administration, and the values are expressed as mean±SEM with n=4 in each group. *p<0.05 compared to baseline and # p<0.05 compared to 10 µg/kg dose of clonidine.

FIG. 5 shows the cardiovascular effects of centhaquin (0.05, 0.15, and 0.45 mg/kg) in urethane anaesthetized rats. Dose-response effect of centhaquin was recorded for 60 minutes, and values for MAP (FIG. 5A), PP (FIG. 5B) and HR (FIG. 5C) are expressed as mean±SEM with n=4 in each group. *p<0.05 compared to baseline and # p<0.05 compared to 0.33 mg/kg dose of centhaquin.

FIG. 6 shows the effect of ET-1 (100, 300, and 900 ng/kg) treatment on centhaquin-induced cardiovascular responses in urethane anaesthetized rats. The MAP (FIG. 6A), PP (FIG. 6B), and HR (FIG. 6C) was recorded for 60 minutes after centhaquin (0.15 mg/kg) administration, and the values are expressed as mean±SEM with n=4 in each group. *p<0.05 compared to baseline and # p<0.05 compared to 0.15 mg/kg dose of centhaquin.

FIG. 7 shows the effect of non-selective $ET_A/ET_B$ receptor antagonist TAK-044 (1 mg/kg) and selective $ET_A$ receptor antagonist BMS-182874 (9 mg/kg) treatment on centhaquin-induced cardiovascular responses in urethane anaesthetized rats. The MAP (FIG. 7A), PP (FIG. 7B), and HR (FIG. 7C) was recorded for 60 minutes after centhaquin (0.15 mg/kg) administration, and the values are expressed as mean±SEM with n=4 in each group. *p<0.05 compared to baseline and # p<0.05 compared to 0.33 mg/kg dose of clonidine.

FIG. 8 shows the effect of prazosin (0.1 mg/kg) on ET-1 (300 ng/kg) induced changes in cardiovascular responses of centhaquin (0.15 mg/kg) in urethane anaesthetized rats. The MAP (FIG. 8A), PP (FIG. 8B), and HR (FIG. 8C) was recorded for 60 minutes after centhaquin (0.33 mg/kg) administration, and the values are expressed as mean±SEM with n=4 in each group. *p<0.05 compared to baseline and # p<0.05 compared to 0.15 mg/kg dose of centhaquin.

REFERENCES

R A Abo-Zena et al., *Pharmacotherapy* 20:476-478 (2000).
A L Backo et al., *Ann Pharmacother* 36:1396-1398 (2002).
U C Bajpai et al., *J. Molecular Structure* 516:15-21 (2000).
M Bhatnagar et al., *Arzneimittelforschung* 35:693-697 (1985).
P Bousquet et al., *Biochem Pharmacol* 32:1459-1465 (1983).
R Brondani et al., Clin Biochem 40:282-284 (2007).
A Carpy et al., *Acta Crystallographica* C47:227-229 (1991).
G O Carrier et al., *J Pharmacol Exp Ther* 232:682-687 (1985).
R Charu et al. *Thorax* 61:1011-1012 2006).
H I Chen *Circulation* 90:970-975 (1994).
P M Consigny *Eur J Pharmacol* 186:239-245 (1990).
G D'Angelo *Am J Physiol Heart Circ Physiol* 290:H1251-1258 (2006).
M S Fagura et al., *Br J Pharmacol* 120:247-258 (1997).
M Gondre et al., J Pharmacol Exp Ther 286:635-642 (1998).
A Gulati *Life Sci* 50:153-160 (1992).
A Gulati et al. *Drug Development Research* 23:307-323 (1991a).
A Gulati *Drug Development Research* 22:141-152 (1991b).
A Gulati et al. *Neuropeptides* 31:301-309 (1997a).
A Gulati et al. *Am J Physiol* 273:H1177-1186 (1997b).
A Gulati et al. (1993) *Eur J Pharmacol* 230:293-300.
P G Guyenet et al. *J Neurosci* 1:908-917 (1981).
K A Hickey et al. *Am J Physiol* 248:C550-556 (1985).
S N Hunyor et al. *Br Med J* 4:23 (1975).
S Ikeda et al. *J Pharmacol Exp Ther* 270:728-733 (1994).
Y P Jarajapu et al. *Eur J Pharmacol* 422:127-135 (2001).
W B Kennedy et al. *Cell Mol Neurobiol* 26:645-657 (2006).
W Kobinger *Rev Physiol Biochem Pharmacol* 81:39-100 (1978).
W Kobinger et al. *Arzneimittelforschung* 17:292-300 (1967).
T Kuwaki et al. *Jpn J Physiol* 40:97-116 (1990).
S Z Langer et al. *Hypertension* 2:372-382 (1980).
O H Lowry et al. *J Biol Chem* 193:265-275 (1951).
V A Murthi et al. in (Patent US ed), *Council of Scientific and Industrial Research* (1976).
N E Naftchi et al. *J Spinal Cord Med* 20:355-360 (1997).
K Nakayama et al. *Br J Pharmacol* 104:978-986 (1991).
P T Nowicki et al. *J Pediatr* 146:805-810 (2005).
Y Ouchi et al. *Am J Physiol* 256:H1747-1751 (1989).
P Pacher et al. *Nat Protoc* 3:1422-1434 (2008).
G S Pal et al. *Pediatrics* 58:749-750 (1976).
T Radovits et al. Vascul Pharmacol 51:37-43 (2009).
A Sakamoto et al. *J Biol Chem* 268:8547-8553 (1993).
H Schmitt *Eur J Pharmacol* 6:8-12 (1969).
S S Shetty et al. *Biochem Biophys Res Commun* 191:459-464 (1993).
H C Souza et al. Clin Exp Pharmacol Physiol 35:751-756 (2008).
R C Srimal et al. *Pharmacol Res* 22:319-329 (1990).
P D Stein et al. *J Med Chem* 37:329-331 (1994).
Y Tabuchi et al. *Biochem Biophys Res Commun* 161:803-808 (1989).
P B Timmermans et al. *Eur J Pharmacol* 63:199-202 (1980).
A L Troncoso et al. *Psychosomatics* 45:449-450 (2004).
D C U'Prichard et al. *Mol Pharmacol* 13:454-473 (1977).
P A van Zwieten et al. *Hypertension* 6:1128-33 (1984).
J Vazquez-Prado et al., *J Biol Chem* 272:27330-27337 (1997).
S W Watts *Am J Physiol Regul Integr Comp Physiol* (2009).
S W Watts *Hypertension* 35:244-248 (2000).
N P Wiklund et al., *Acta Physiol Scand* 134:311-312 (1988).
M Yanagisawa et al., *Nature* 332:411-415 (1988).

Methods to Treat Pain

The present invention also relates to the use of centhaquin as an analgesic to treat pain in a subject.

In one aspect, the invention provides a method of treating or preventing pain comprising administering to a mammal in need thereof a therapeutically effective amount of centhaquin. In one embodiment, the centhaquin is coadministered with an opiate analgesic.

In one embodiment, the centhaquin is administered in a dose range from about 10 µg to about 300 µg.

The present method contemplates that the subject to be treated is a mammal. In one embodiment, the mammalian subject is human, or any non-human animal model for human medical research, or an animal of importance as livestock or pets, for example, companion animals. In a related embodiment, the subject is a human.

In one embodiment, the pain to be treated is chronic pain or acute pain. In a related embodiment, the pain is selected from the group consisting of causalgia, tactile allodynia, neuropathic pain, hyperalgesia, hyperpathia, inflammatory pain, post-operative pain, chronic lower back pain, cluster headaches, postherpetic neuralgia, phantom limb and stump pain, central pain, dental pain, neuropathic pain, opioid-resistant pain, visceral pain, surgical pain, bone injury pain, diabetic neuropathy pain, post-surgery or traumatic neuropathy pain, peripheral neuropathy pain, entrapment neuropathy pain, neuropathy caused by alcohol abuse, pain from HIV infection, multiple sclerosis hypothyroidism or anticancer chemotherapy pain, pain during labor and delivery, pain resulting from burns, including sunburn, post partum pain, migraine, angina pain, and genitourinary tract-related pain including cystitis.

In a further aspect, centhaquin is useful to potentiate the analgesic effects of an opiate analgesic. As such, the invention provides a method of treating or preventing pain comprising administering to a mammal in need thereof a therapeutically effective amount of an opiate analgesic and a therapeutically effective amount of a centhaquin.

The opiate analgesic is selected from the group consisting of morphine, morphine sulfate, codeine, diacetylmorphine, dextromethorphan, hydrocodone, hydromorphone, hydromorphone, levorphanol, oxymorphone, oxycodone, levallorphan, and salts thereof.

In an embodiment, the opiate analgesic and centhaquin are administered simultaneously. In a related embodiment, the opiate analgesic and centhaquin are administered from a single composition or from separate compositions. In a further embodiment, the opiate analgesic and centhaquin are administered sequentially.

In one embodiment, the present invention relates to methods of treating pain using centhaquin which produces significant analgesia and relief from pain stimulation.

The term "treatment" as used herein, refers to preventing, reducing or otherwise ameliorating or eliminating pain. As such, the term "treatment" includes both medical therapeutic and/or prophylactic administration, as appropriate. Treatment and relief of pain symptoms may be measured using pain assessment scales known in the art. Exemplary protocols include measurement of the subjective pain threshold (visual analog scale) and the objective nociceptive flexion reflex (R III) threshold.

The term "pain" as used herein, refers to all types of pain. In one aspect, the term refers to acute and chronic pains. Exemplary types of pain include, but are not limited to, causalgia, tactile allodynia, neuropathic pain, hyperalgesia, hyperpathia, inflammatory pain, post-operative pain, chronic lower back pain, cluster headaches, postherpetic neuralgia, phantom limb and stump pain, central pain, dental pain, neuropathic pain, opioid-resistant pain, visceral pain, surgical pain, bone injury pain, diabetic neuropathy pain, post-surgery or traumatic neuropathy pain, peripheral neuropathy pain, entrapment neuropathy pain, neuropathy caused by alcohol abuse, pain from HIV infection, multiple sclerosis hypothyroidism or anticancer chemotherapy pain, pain during labor and delivery, pain resulting from burns, including sunburn, post partum pain, migraine, angina pain, and genitourinary tract-related pain including cystitis.

The term "analgesic" as used herein refer to an active agent that relieves pain in a subject. The term "opiate analgesic" or "opioid analgesic" refers to a narcotic analgesic used, for example, as an adjunct to anesthesia, or to alleviate pain. The term "non-opiate analgesic" refers to a non-narcotic agent indicated for pain.

A "therapeutically effective dose" refers to that amount of the active agent or agents that results in achieving the desired effect. Toxicity and therapeutic efficacy of such active agents are determined by standard pharmaceutical procedures in cell cultures or experimental animals, e.g., determining the LD50 (the dose lethal to 50% of the population) and the ED50 (the dose therapeutically effective in 50% of the population). The dose ratio between toxic and therapeutic effects is the therapeutic index, which is expressed as the ratio between LD50 and ED50. A high therapeutic index is preferred. The data obtained from such data is used in formulating a range of dosage for use in humans. The dosage of the active agents, in one aspect, lies within a range of circulating concentrations that include the ED50 with little or no toxicity. The dosage varies within this range depending upon the dosage form employed, and the route of administration utilized.

"Concurrent administration," "administered in combination," "simultaneous administration" or similar phrases mean that a composition comprising two or more agents are administered concurrently to the subject being treated. By "concurrently," it is meant that each agent is administered at the same time or sequentially in any order at different points in time. However, if not administered at the same time, they are, in one aspect, administered sufficiently closely in time so as to provide the desired potentiation of treatment effect. Suitable dosing intervals and dosing order with such compounds will be readily apparent to those skilled in the art. It is also contemplated that two or more agents are administered in separate compositions, and in one aspect, one composition is administered prior to or subsequent to administration of the first agent. Prior administration refers to administration of the agents within the range of one day (24 hours) prior to treatment up to 30 minutes before treatment. It is further contemplated that one agent is administered subsequent to administration of the other agent. Subsequent administration is meant to describe administration from 30 minutes after administration of the first agent up to one day (24 hours) after administration of the first agent. Within 30 minutes to 24 hours may includes administration at 30 minutes, 1, 2, 3, 4, 5, 6, 7, 8, 9, 10, 11, 12, 16, 20, or 24 hours.

The term "low dose" as used herein refers to a dose of an active ingredient in a composition, wherein the amount of active ingredient in the composition is lower than that typically given in treatment of a subject. For example, the low dose of active agent may be administered in combination with a second active agent such that the active agents exhibit a synergistic effect, and the dose of each active agent in the combination treatment is lower than the dose necessary when the agent is administered not in combination with a second active ingredient.

Available opiate and opioid analgesics are derivatives of five chemical groups (i.e., phenanthrenes, phenylheptylamines, phenylpiperidines, morphinans, and benzomorphans). Pharmacologically, opiates and nonopiates differ significantly in activity. Some are strong agonists (morphine), others are moderates-to-mild agonists (codeine). In contrast, some opiate derivatives exhibit mixed agonist-antagonist activity (nalbuphine), whereas others are opiate antagonists (naloxone). Morphine is the prototype of the opiate and opioid analgesics, all of which have similar actions on the central nervous system.

Morphine is chemically derived from opium. Other drugs, such as heroin, are processed from morphine or codeine. Such opiates have been used both medically and nonmedically for centuries. By the early 19th century, morphine had been extracted in a pure form suitable for solution. With the introduction of the hypodermic needle, injection of a morphine solution became the common method of administration. Of the twenty alkaloids contained in opium, only codeine and morphine are still in widespread clinical use.

The opium group of narcotic drugs are among the most powerfully acting and clinically useful drugs producing depression of the central nervous system. Drugs of this group are used principally as analgesics, but possess numerous other useful properties. Morphine, for example, is used to relieve pain, induce sleep in the presence of pain, check diarrhea, suppress cough, ease dyspnea, and facilitate anesthesia.

When morphine and related compounds are administered over a long period of time, tolerance to the analgesic effect develops, and the dose then must be increased periodically to obtain equivalent pain relief. Eventually, tolerance and physical dependence develop, which, combined with euphoria, result in excessive use and addiction of those patients having susceptible personalities. For these reasons, morphine and its derivatives must be used only as directed by a physician (i.e., not in greater dose, more often, or longer than prescribed), and should not be used to treat pain when a different analgesic will suffice.

It is contemplated that centhaquin is useful to potentiate the analgesic effects of an opiate analgesic. Opiate analgesics include, but are not limited to, (a) opium; (b) opium alkaloids, such as morphine, morphine sulfate, codeine, codeine phosphate, codeine sulfate, diacetylmorphine, morphine hydrochloride, morphine tartrate, and diacetylmorphine hydrochloride; and (c) semisynthetic opiate analgesics, such as dextromethorphan hydrobromide, hydrocodone bitartrate, hydromorphone, hydromorphone hydrochloride, levorphanol tartrate, oxymorphone hydrochloride, and oxycodone hydrochloride.

It is contemplated that the subject treated using the methods described herein is a mammalian subject. The mammalian subject may be human, or any non-human animal model for human medical research, or an animal of importance as livestock or pets, for example, companion animals.

Administration of the pharmaceutical composition(s) can be performed before, during, or after the onset of pain.

The present invention provides methods for alleviating and treating symptoms that arise in a subject experiencing pain. In one aspect, the invention provides a method of treating or preventing pain comprising administering to a mammal a therapeutically effective amount of centhaquin.

The causes of pain include, but are not limited to inflammation, injury, disease, muscle spasm and the onset of a neuropathic event or syndrome. Acute pain is usually self-limited, whereas chronic pain generally persists for 3 months or longer and can lead to significant changes in a patient's personality, lifestyle, functional ability and overall quality of life. Ineffectively treated pain can be detrimental to the person experiencing it by limiting function, reducing mobility, complicating sleep, and interfering with general quality of life.

Inflammatory (nociceptive) pain can occur when tissue is damaged, as can result from surgery or due to an adverse physical, chemical or thermal event or to infection by a biologic agent. Neuropathic pain is a persistent or chronic pain syndrome that can result from damage to the nervous system, the peripheral nerves, the dorsal root ganglion or dorsal root, or to the central nervous system. Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is characterized by spontaneous burning pain combined with hyperalgesia and allodynia. Hyperalgesia is characterized by extreme sensitivity to a painful stimulus. (Meller et al., Neuropharmacol. 33:1471-8, 1994). This condition can include visceral hyperalgesia which generates the feeling of pain in internal organs. Neuropathic pain also includes hyperpathia, wherein a stimulus that is normally innocuous if given for a prolonged period of time results in severe pain.

Treatment of chronic pain in human patients is carried out generally as described in U.S. Pat. No. 6,372,226. In one aspect, a patient experiencing acute inflammatory pain, neuropathic pain, spastic conditions, or other chronic pain from an injury is treated by intrathecal administration, for example by spinal tap to the lumbar region, with an appropriate dose of a composition described herein for use in a method of the invention. In an additional example, if the subject suffers from arthritis or other joint pain, compositions are administered intraarticularly. The particular dose and site of injection, as well as the frequency of administrations, depend upon a variety of factors within the skill of the treating physician.

Amelioration of pain symptoms is measured using methods known in the art, including the visual analog scale (VAS), the verbal rating scale (VRS) and the numerical rating scale (NRS) (Williamson et al., J Clin Nurs. 14:798-804, 2005; Carlsson, A., Pain. 1983 16:87-101, 1983). For the visual analog scale, the verbal rating scale, and the numeric rating scale, generally, patients are asked to rate their pain on a numeric scale before and after pain stimulus. Chronic pain is also assessed by an objective scaled test such as the Leeds Assessment of Neuropathic Symptoms and Signs (LANSS) Pain Scale (Bennett, M. Pain. 92:147-157, 2001). A decrease in hypersensitivity to pain stimulus after treatment with a composition comprising an $\alpha_2$ adrenergic agonist and/or an endothelin receptor antagonist indicates that interfering with normal activity a $\alpha_2$ adrenergic receptors and/or endothelin receptors alleviates symptoms associated with chronic pain. It another aspect of the invention, the compositions described herein are administered in conjunction with another pain medications as described above, wherein the therapies provide a synergistic effect in relieving symptoms of chronic pain.

Improvement in pain is measured at varying timepoints after administration of analgesic is administered and the reduction in pain based on the measurement scale is assessed. In one embodiment, assessment of pain symptoms is carried out every 1, 2, 3, 4, 5, 6, or 8 weeks, or as determined by a treating physician. In one embodiment, the improvement in pain symptoms in a subject, when compared to assessment of pain symptoms before treatment, may be at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% as measured using art-recognized pain scales.

As an additional aspect, the invention includes kits which comprise one or more compounds or compositions packaged in a manner which facilitates their use to practice methods of the invention. In a simplest embodiment, such a kit includes a compound or composition described herein as useful for practice of a method of the invention (i.e., centhaquin), packaged in a container such as a sealed bottle or vessel, with a label affixed to the container or included in the package that describes use of the compound or composition to practice the method of the invention. Preferably, the compound or composition is packaged in a unit dosage form. The kit may further include a device suitable for administering the composition according to a preferred route of administration.

The data in FIGS. 9-13 show that:

(a) centhaquin (0.1, 0.3 and 0.9 mg/kg, iv) produced dose-dependent analgesia;

(b) centhaquin (0.3 and 0.9 mg/kg, iv) potentiated morphine analgesia;

(c) the analgesic effect of centhaquin (0.3 mg/kg, iv) was comparable to 4 mg/kg dose of morphine analgesia; and (d) the analgesic effect of centhaquin (0.9 mg/kg, iv) was significantly greater than 4 mg/kg dose of morphine analgesia.

REFERENCES

L G Hegde et al. *Pharmacol Res* 36:109-114 (1997).

A Gulati et al. *Eur J Pharmacol* 231:151-156 (1993).

R C Srimal et al. *Pharmacol Res* 22:319-329 (1990).

M Bhatnagar et al. *Arzneimittel-Forschung* 35:693-697 (1985).

A Gulati et al. *Drug Development Research* 23:307-323 (1991).

A Murti et al. *Indian Journal of Chemistry Section B-Organic Chemistry Including Medicinal Chemistry* 28B, 934 (1989).

Methods to Treat Resuscitative Hemorrhagic Shock

The present invention also is directed to methods of treating resuscitative hemorrhagic shock comprising the administration of a therapeutically effective amount of centhaquin to an individual in need thereof.

In general, hemorrhagic shock is marked by a critical reduction in tissue perfusion, leading to tissue acidosis and hypoxia, compromising the cellular metabolic activity, and cellular and organ function. Hyporesponsiveness to vasoconstrictors during hemorrhagic shock has been documented. Hemorrhagic shock states ranging from mild to severe encompass a number of pathophysiologic, immunologic, and metabolic processes. An increase in base deficit during traumatic shock correlates well with multiple organ failure and a state of decompensation followed by mortality in humans. Base deficit paralleled the hemodynamic variables including mean arterial pressure, heart rate, and cardiac output. The changes in the oxygen delivery and consumption during resuscitation that improved compensation of shock are accurately reflected in base deficit alterations. Whereas base deficit is an indicator of metabolic stress with onset and progression of shock, endothelial and smooth muscle cells in the blood vessels can release a number of vasomediators with injury and onset of blood loss.

However, limited information is available to define the role of vasomediators in the state of vascular decompensation during hemorrhagic shock. An elevation in the concentration of circulating plasma ET-1 has been observed. It is not clear whether the duration of hemorrhagic shock correlates with the systemic or regional (local) ET-1 levels during different states of hemorrhagic shock. It is possible that a need for rapid compensation for loss of blood volume during hemorrhagic shock stimulates production of ET-1, which in turn can modulate adrenergic receptors. Therefore, centhaquin was used as an adrenergic agent as a main component of a resuscitative solution for the treat of conditions associated with compensatory and decompensatory states of hemorrhagic shock. The method is not be limited to hemorrhagic shock, but can be used to treat any shock due to circulatory failure.

Figure 14A:
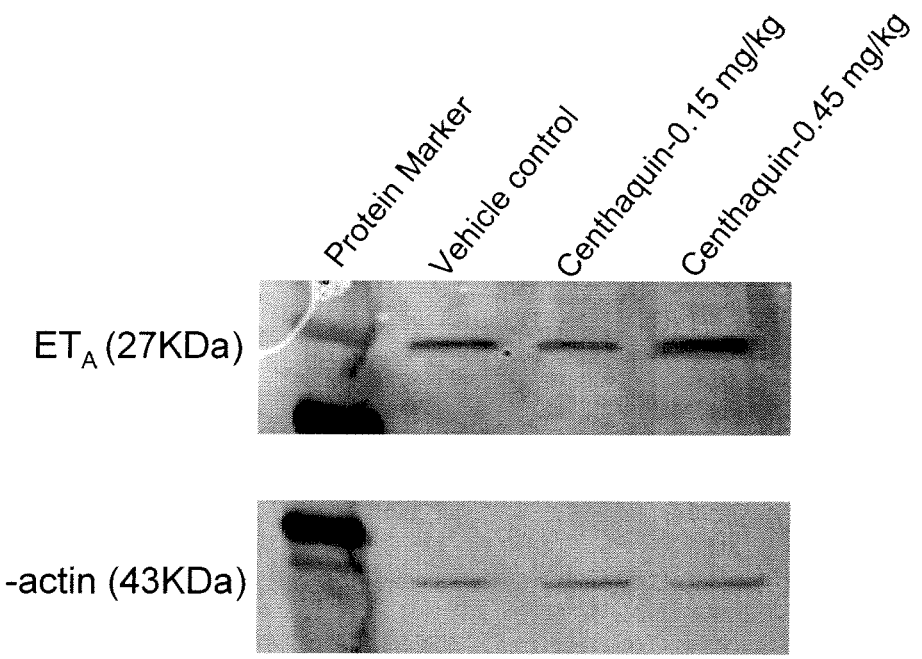
FIG. 14A contains an immunoblot showing $ET_A$ receptor expression in rat brain after 1 hour of centhaquin treatment.
Figure 14B:
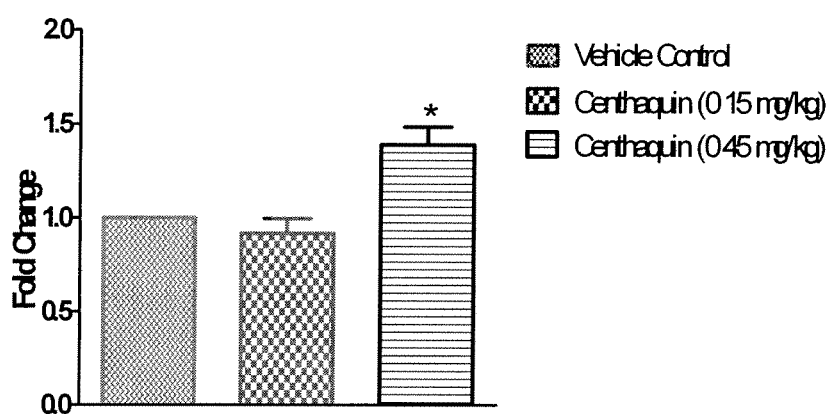
FIG. 14B contains bar graphs of fold change in the expression of $ET_A$ receptor normalized to β-actin, as assessed by densitometry.

FIG. 14 shows the fold change in the expression of $ET_A$ receptors normalized to β-action assessed by densitometry. The values are expressed as mean±SEM. *$p<0.05$ compared to a vehicle control. More particularly, FIG. 14 is an immunoblot showing $ET_A r$ expression in rat brain (Lane-2 to Lane-4) and abdominal aorta (Lane-5 to lane-7) after 1 h of clonidine treatment. Lane-1: Protein marker; Lane-2: Vehicle treatment; Lane-3: Clonidine (10 µg·ml$^{-1}$) treatment; Lane-4 clonidine (90 µg·ml$^{-1}$) treatment; Lane-5: Vehicle treatment; Lane-6: Clonidine (10 µg·ml$^{-1}$) treatment; Lane-7: Clonidine (90 µg·ml$^{-1}$) treatment. The blot is representative of four different experiments with similar results (A). Bar graph showing fold change in the expression of $ET_A r$ in rat brain and abdominal aorta normalized to β-actin assessed by densitometry. Values are expressed as mean±SEM, with n=4 rats in each group. *$p<0.05$ compared with vehicle treatment.

Figure 15:
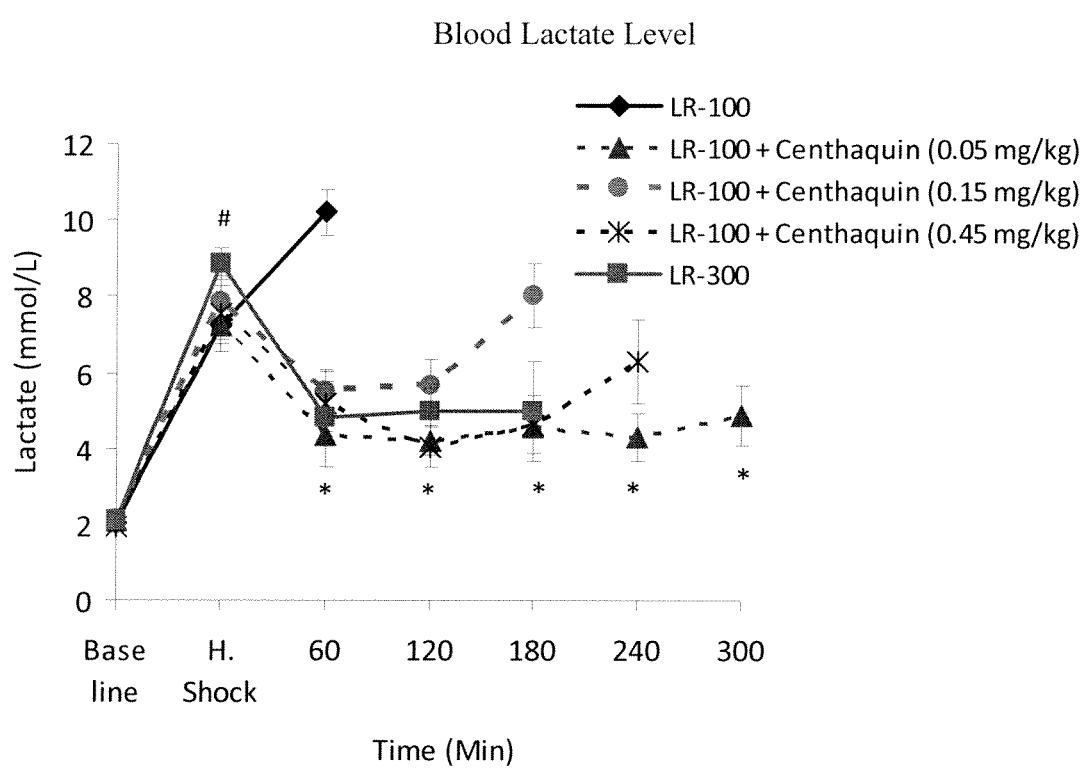
FIG. 15 contains graphs of blood lactate (mmol/L) vs. time (min) in rats resuscitated with Ringer lactate alone or with centhaquin in the hemorrhagic shock model.

FIG. 15 shows the lactate levels in rats resuscitated with Ringer's lactate and centhaquin in a hemorrhagic shock model. Values for lactate are expressed as mean±SEM. With n=5 rats/group. # $p<0.05$ compared to baseline and *$p<0.05$ compared to LR-100 and baseline lactate level after induction of shock. LR-100 is not effective in reversing the blood lactate levels. LR-300 is effective in reducing the blood lactate levels. The graphs show a drop in lactate (mmol/L) with administration of 0.05-0.45 mg/kg of centhaquin. The lower doses of centhaquin were more effective than the higher doses.

Figure 16:
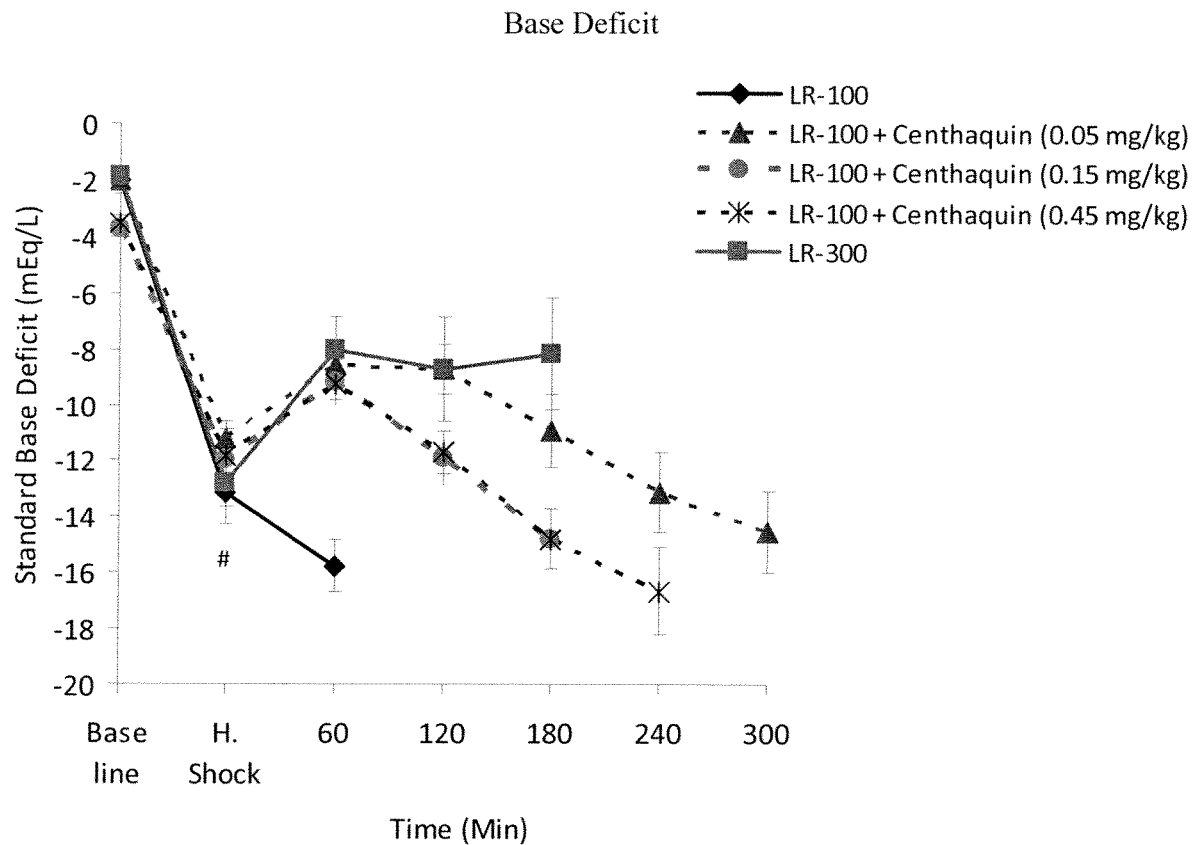
FIG. 16 contains graphs of standard base deficit (mEq/L) vs. time (min) in rats resuscitated with Ringer's lactate alone or with centhaquin in the hemorrhagic shock model.

FIG. 16 shows the standard base deficit (mEq/L) over time for rats resuscitated with Ringer's lactate and centhaquin in hemorrhagic shock model. Values for base deficit are expressed as mean±SEM with n=5 rats/group. # $p<0.05$ compared to baseline. ↑, ↓$p<0.05$ compared to baseline base after hemorrhagic shock (⌑-high base deficit, ↓-low base deficit).

Figure 17:
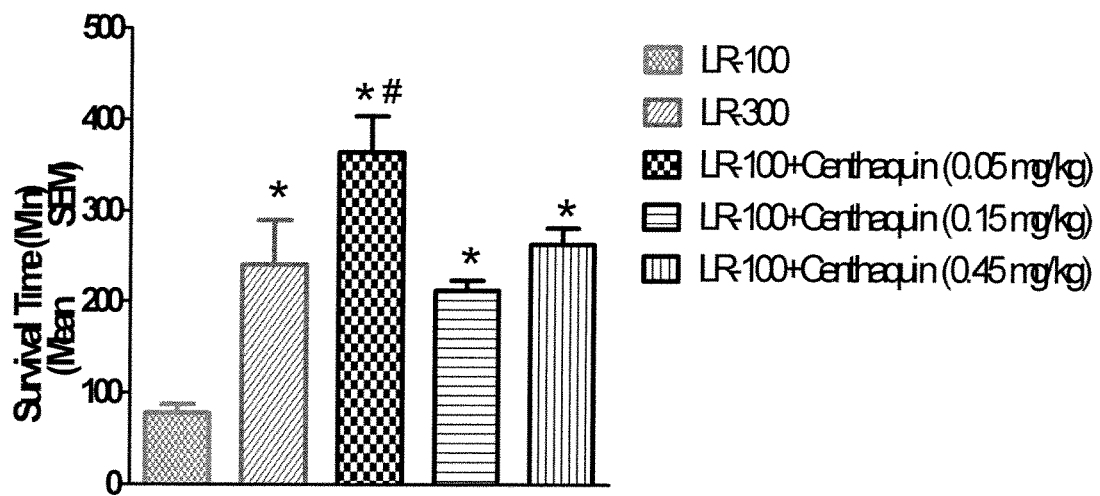
FIG. 17 contains bar graphs showing survival time (min) in rats resuscitated with Ringer's lactate alone or with centhaquin in the hemorrhagic shock model.
Figure 18A:
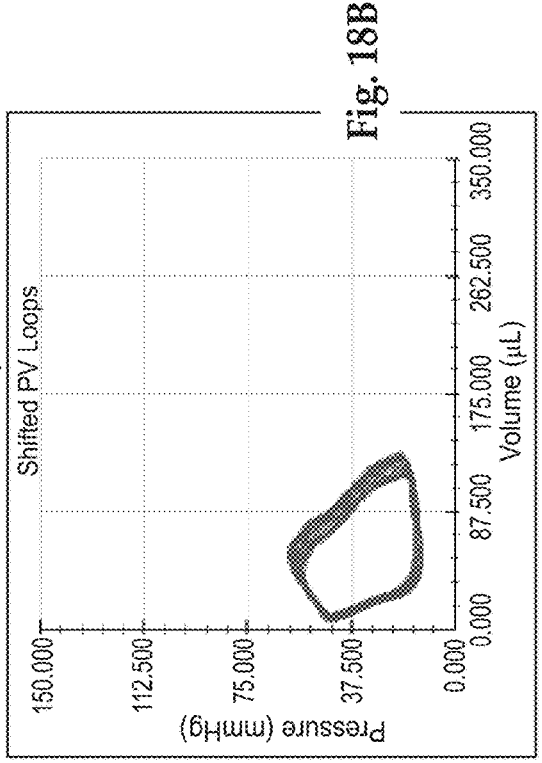
Figure 18B:
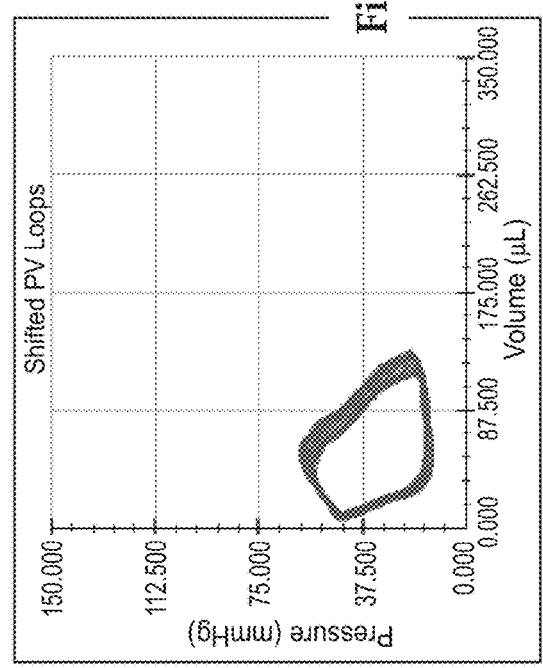
Figure 18C:
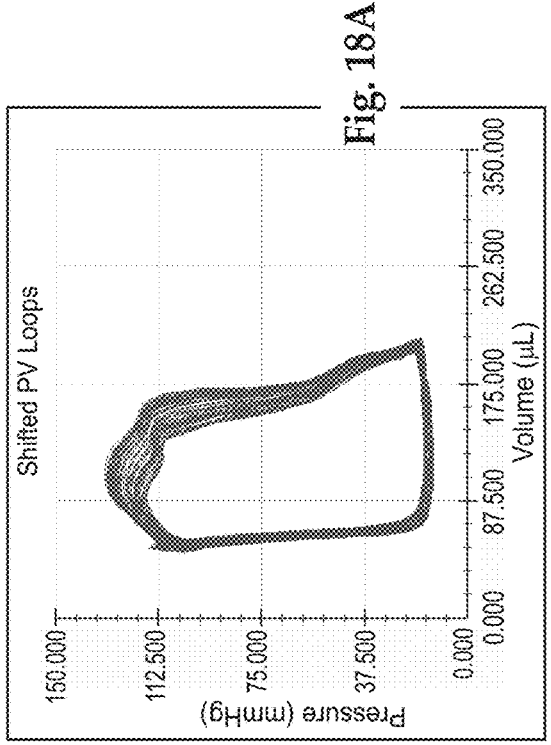
Figure 18D:
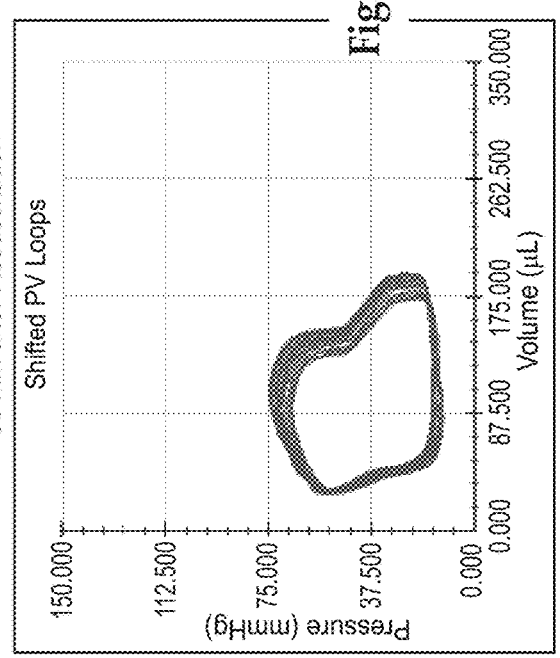

FIG. 17 shows the improvement in survival time for rats resuscitated with Ringer lactate and centhaquin in the hemorrhagic shock model. Values are expressed as mean±SEM with n>5 rats/group. *$p<0.05$ compared to LR-100. # $p<0.05$ compared to LR-300. The data shows an increase in survival time when centhaquin is administered with LR-100.

Figure 20:
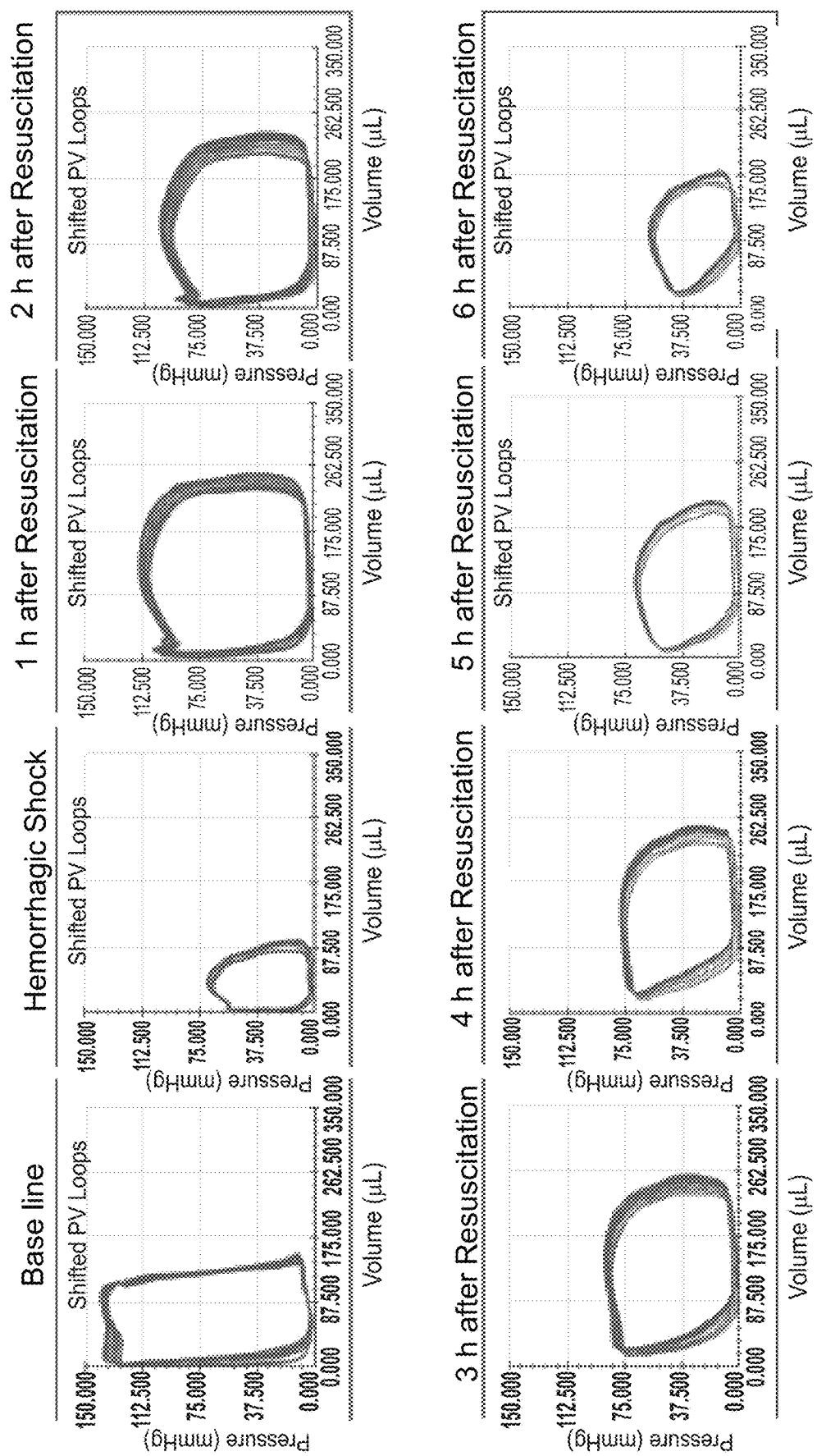
FIG. 20 contains pressure-volume loops for rats resuscitated with Ringer's lactate and centhaquin.

FIGS. 18 and 19 are pressure volume loops for resuscitation of rats with LR-100 and LR-300 over time, respectively. FIG. 20 contains pressure-volume loops showing the effect of resuscitating with LR-100 and centhaquin (0.05 mg/kg). The improvement by administering centhaquin in addition to LR-100 is observed by comparing the pressure-volume loops of FIG. 20 to the loops of FIG. 18.

APPENDIX A
Selective Et$_A$ Antagonists
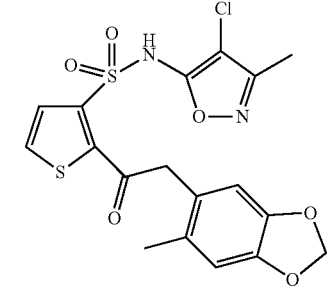
sitaxsentan
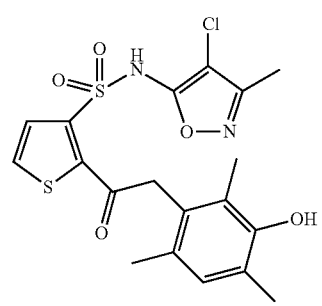
TBC2576
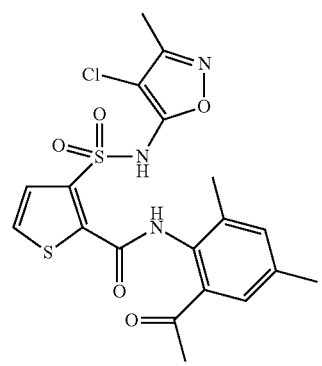
TBC3214
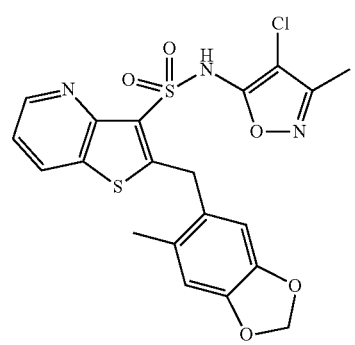
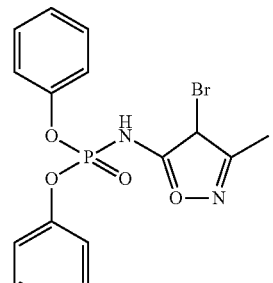
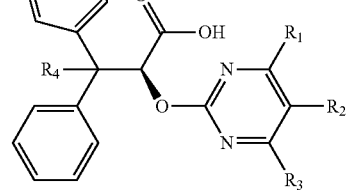
6 R$_1$ = R$_3$ = R$_4$ = CH$_3$, R$_2$ = H
7 R$_1$ = R$_3$ = R$_4$ = OCH$_3$, R$_2$ = F
8 R$_1$ = OCH$_3$, R$_2$ = H, R$_3$ = CH$_3$, R$_4$ = —OCH$_2$CON(CH$_3$)C$_6$H$_5$
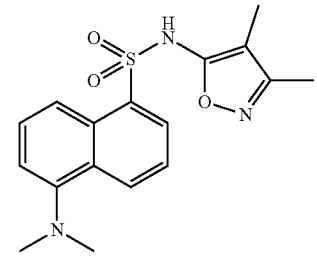
BMS 182, 874
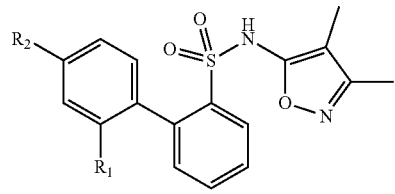
10 R$_1$ = CH$_2$OH, R$_2$ = H
11 R$_1$ = H, R$_2$ = 2-oxazolyl
12 R$_1$ = H, R$_2$ = 2-pyrimidinyl
13 R$_1$ = H, R$_2$ = 4-methoxyethoxymethyl-4-oxo-1, 2, 4-triazol-2-yl
14 R$_1$ = H, R$_2$ = 1, 3 diazo-2-butyl-4-oxospiro (4, 4) -1-nonen-3-ylmethyl
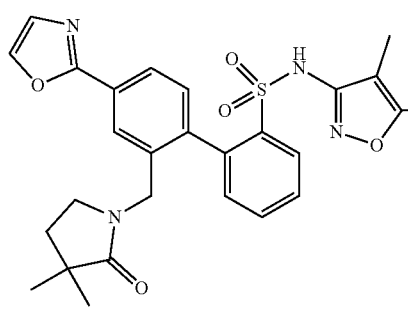

-continued
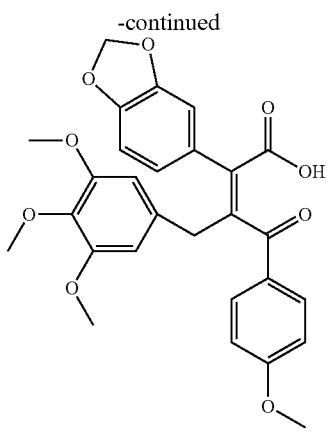
16 R = CH₃ (PD156707)
17 R = CH₂CH₂CH₂SO₃H
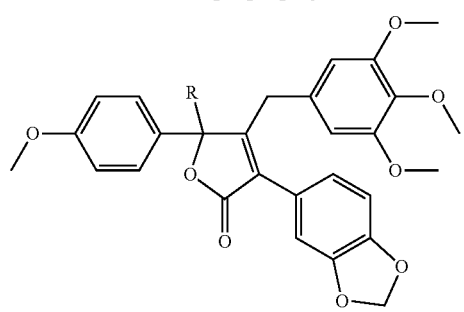
18 R = OCH₂CH₂CH₂SO₃H
19 R = OCONHCH₂CO₂C₂H₅
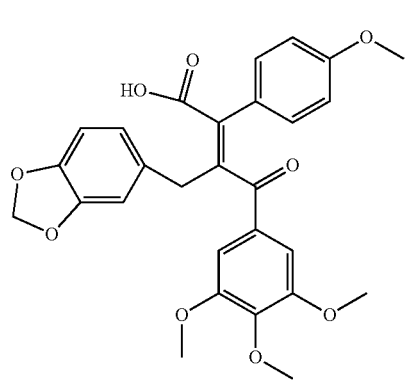
20
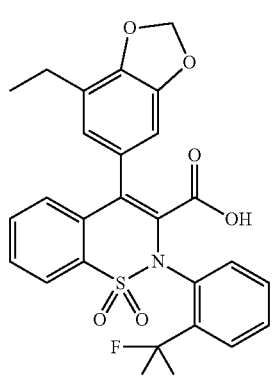
21
PD180988
-continued
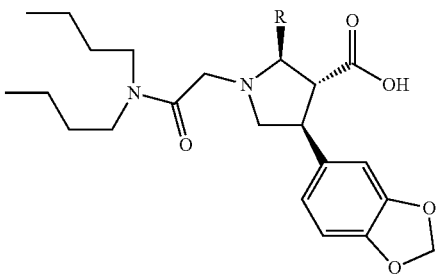
22 R = C₅H₄-4-OCH₃ (ABT-627)
23 R = CH₂CH₂-2-pyridyl
24
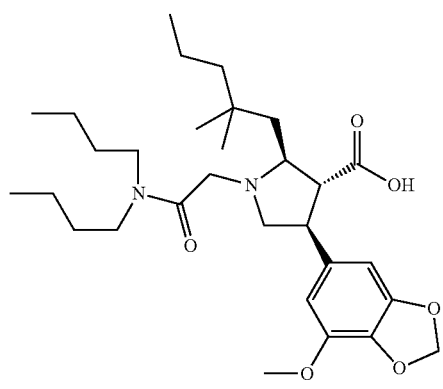
ABT-546
25
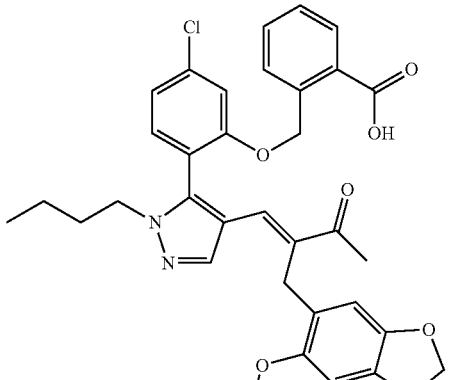
SB247083
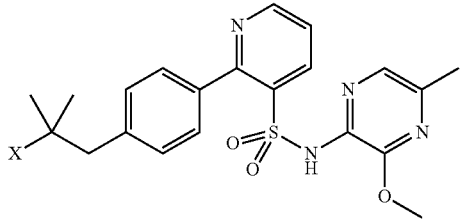
26 X = CO₂H (Z1611)
27 X = H 28
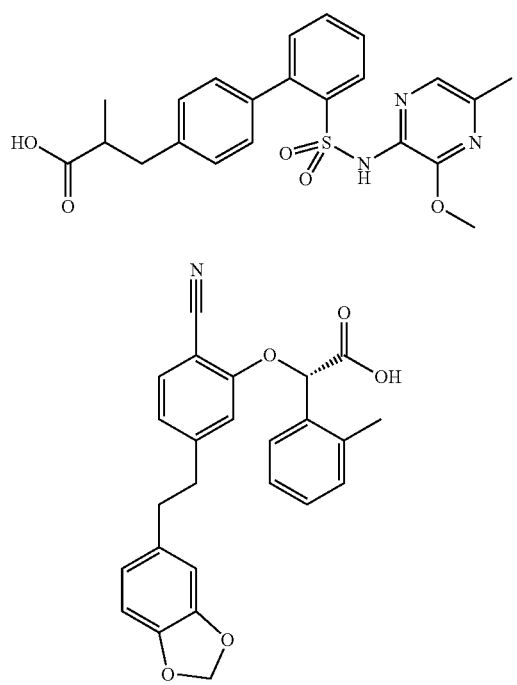
RPR118031A
29
30
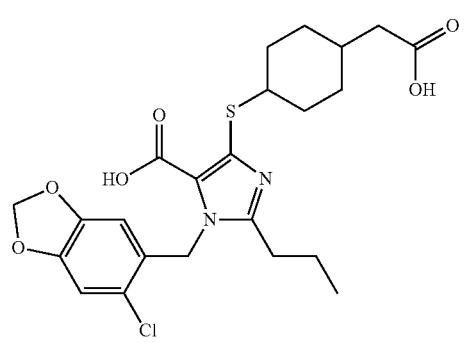
31
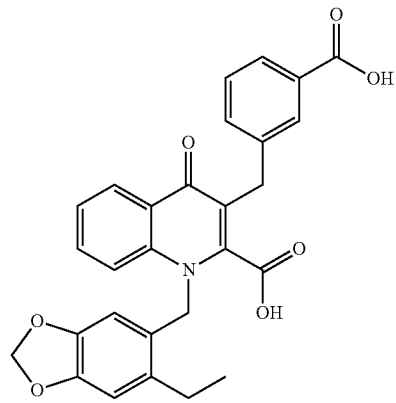
32
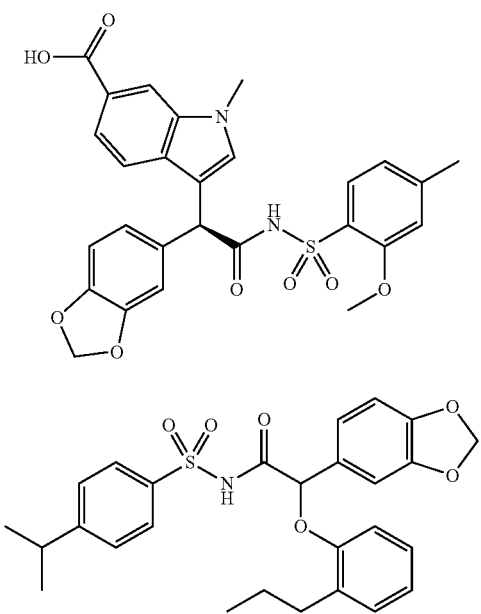
33
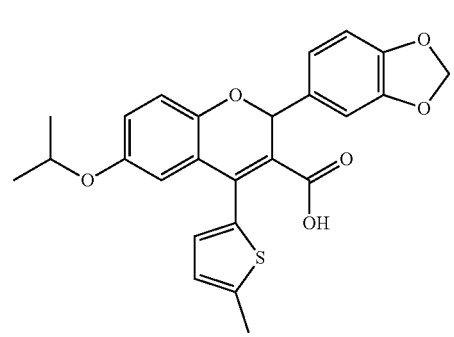
34
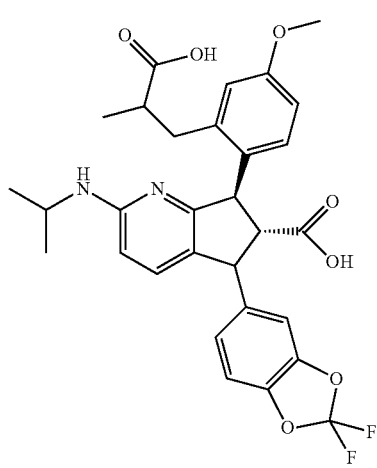
35

37
-continued
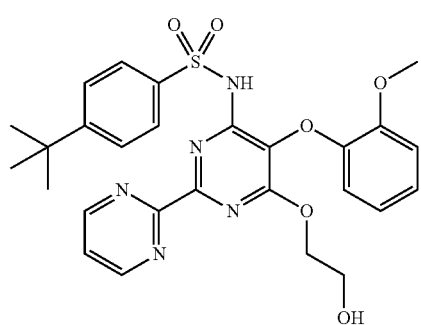
46
bosentan
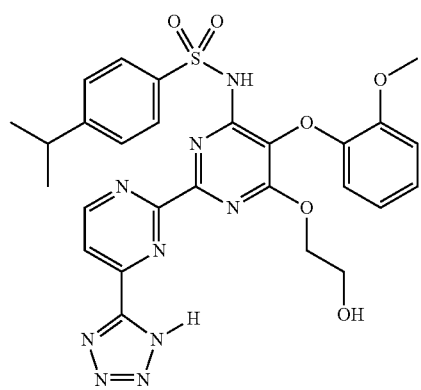
47
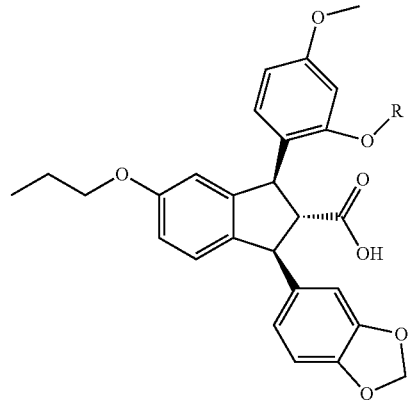
48 R = CH₂CO₂H SB209670
49 R = CH₂CH₂OH SB217242
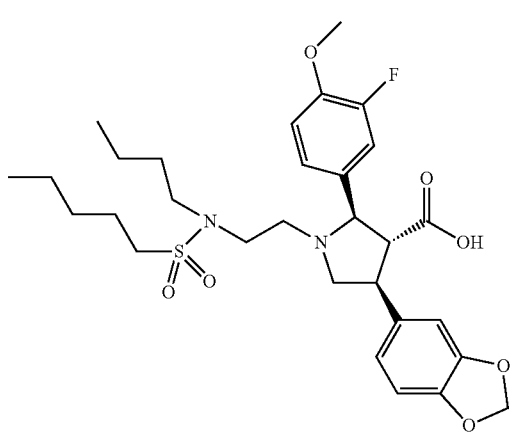
50
38
-continued
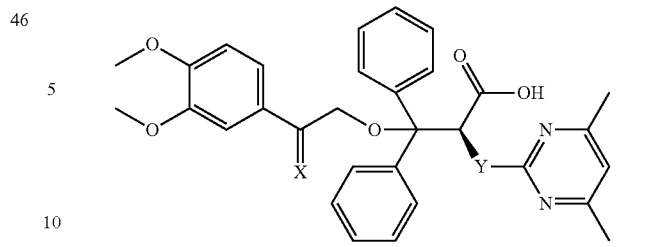
51 X = H₂, Y = CH₂ S-LU 302872
52 X = O, Y = O
53
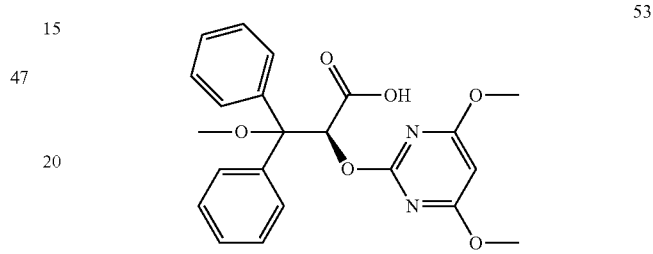
54
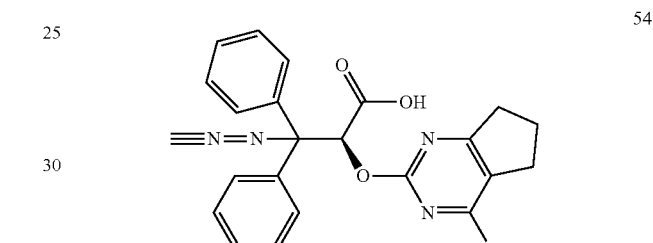
55
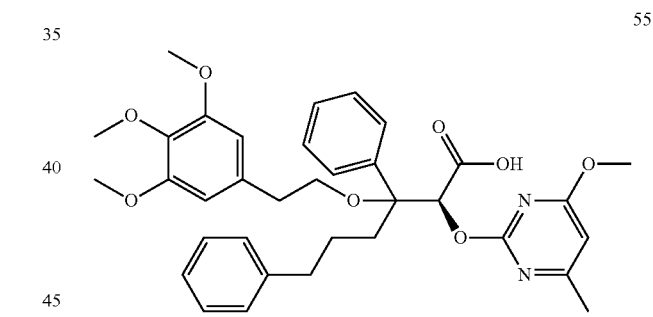
56
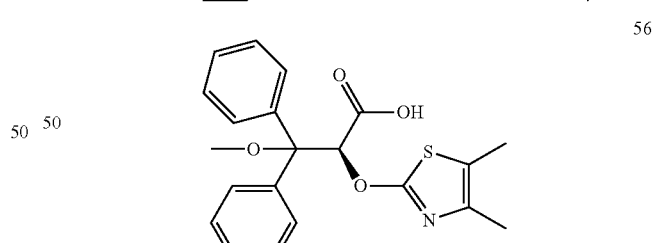
57
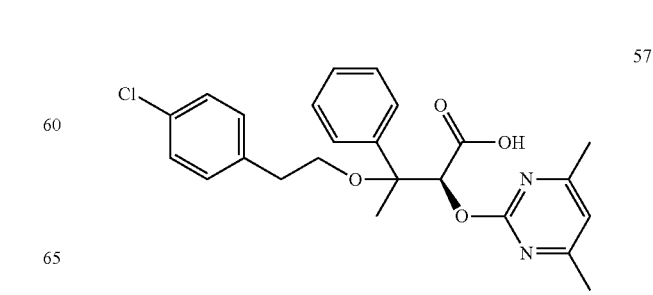

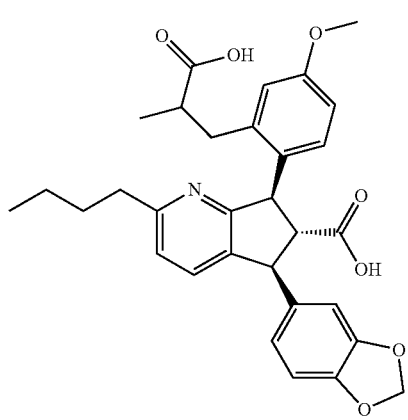
J-104132
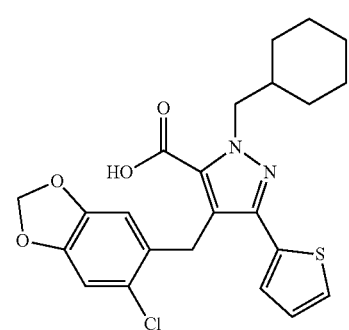
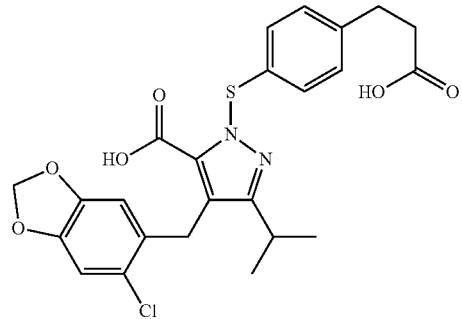
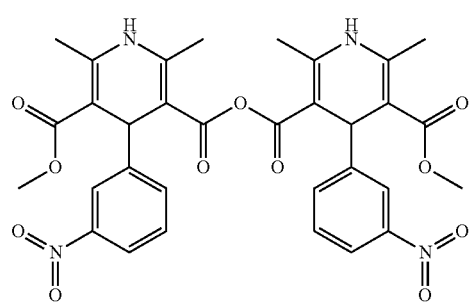
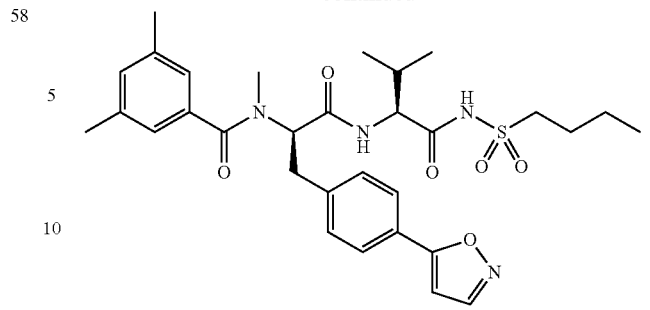
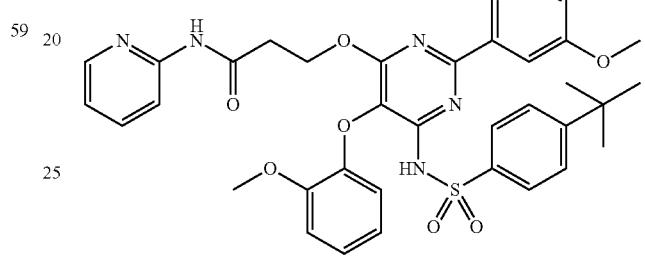
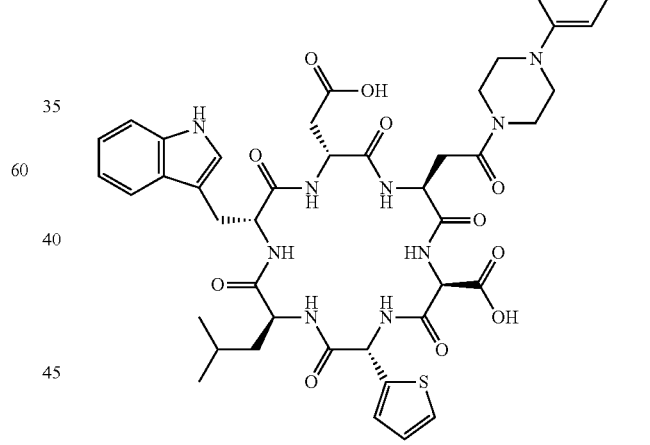
TAK-044
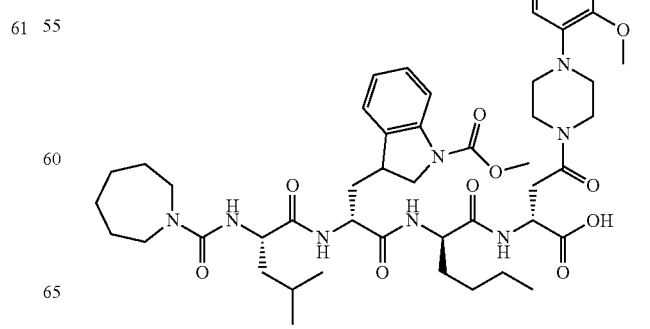

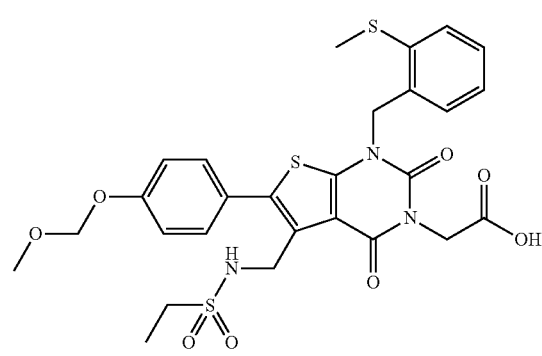
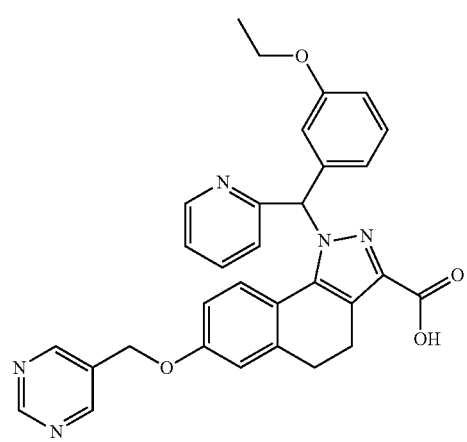
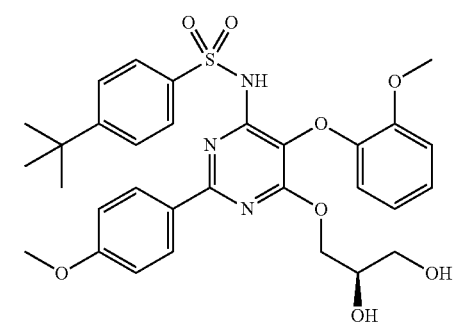
Ro 46-8443
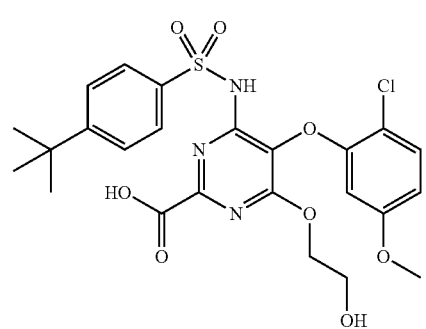
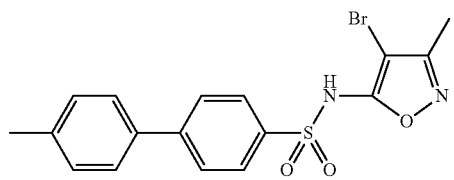
TBC10950
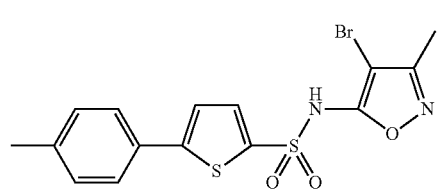
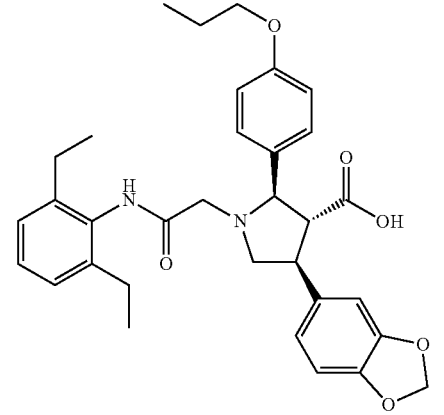
A192621
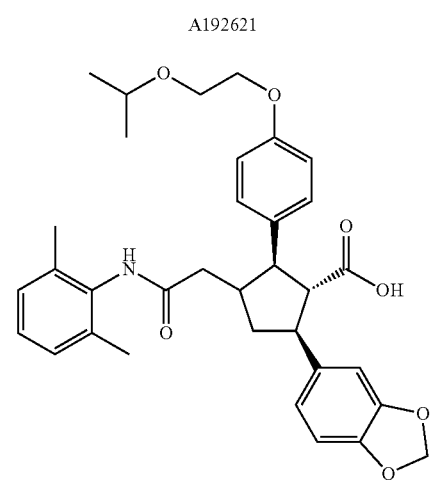
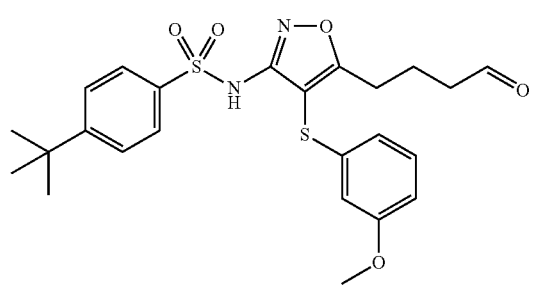

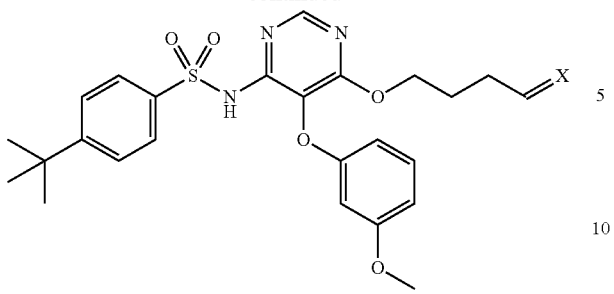
43 X = O
44 X = NNHCO-3-pyridyl
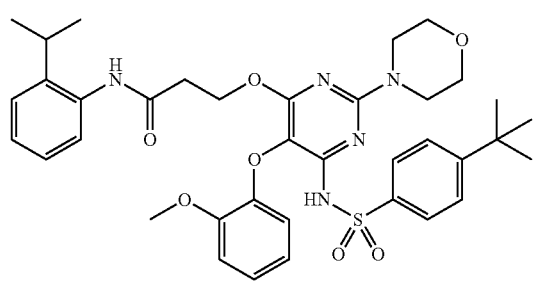
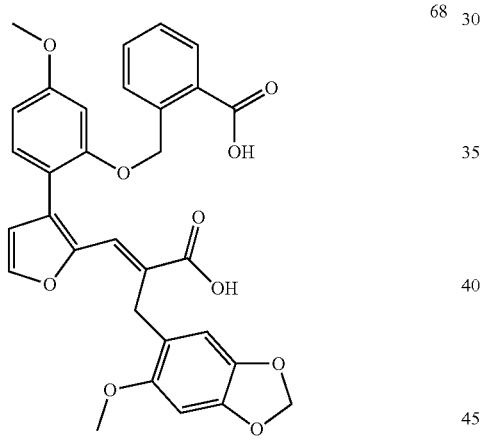
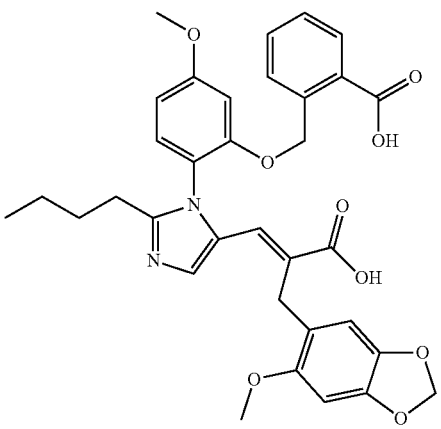
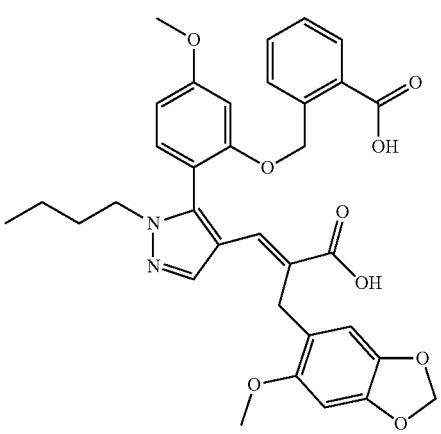
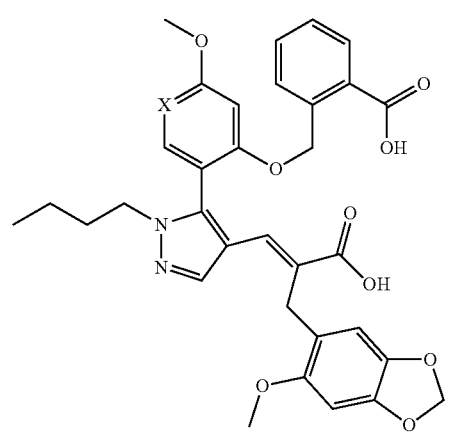
72 X = C
73 X = N

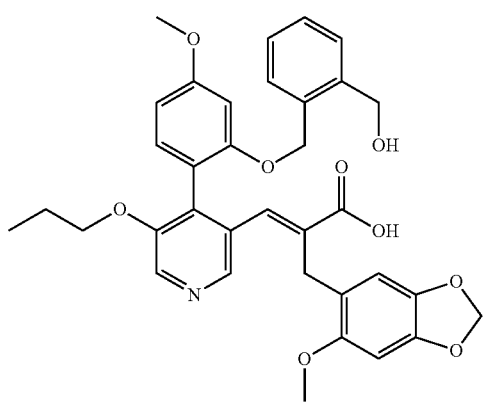
74
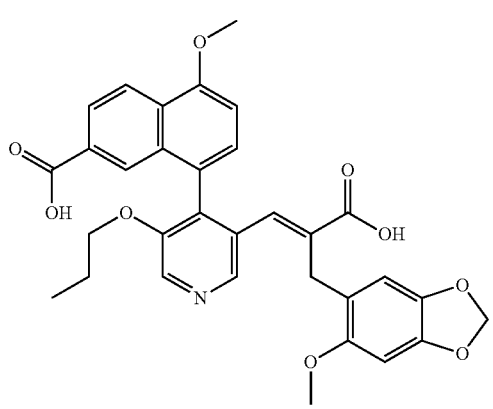
75
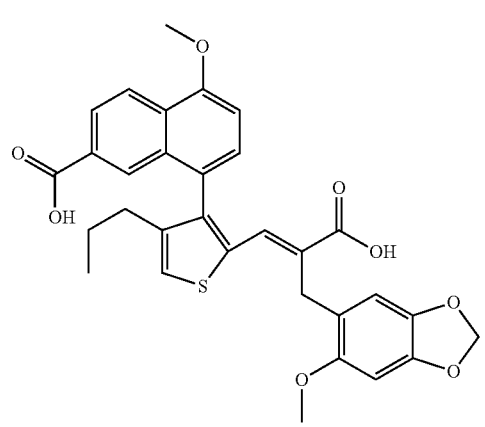
76
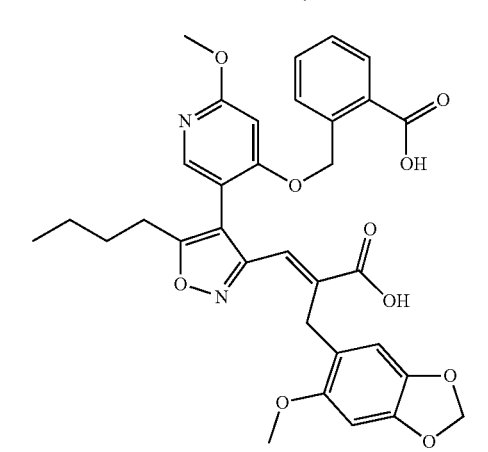
77
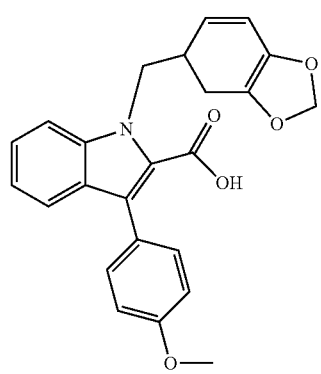
78
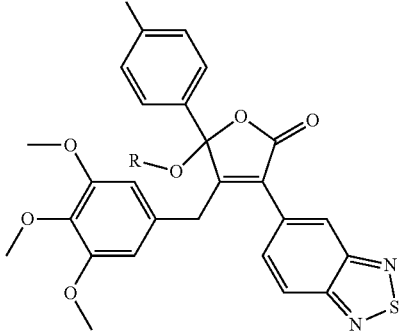
79 R = H
80 R = CONHCH₂CO₂C₂H₅
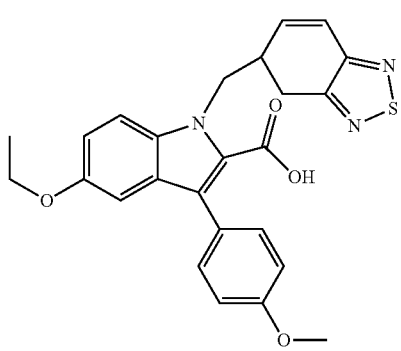
81
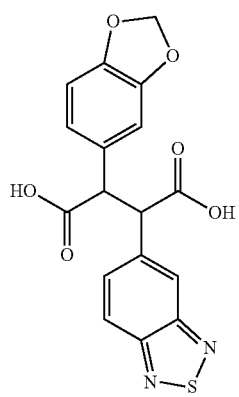
82

US 10,828,368 B2
47 -continued | 48 -continued
83
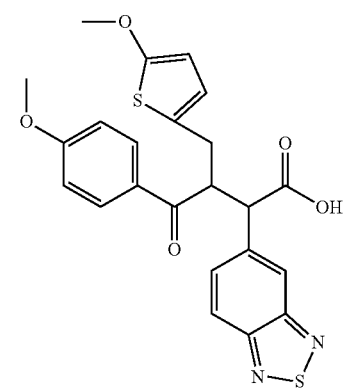
84
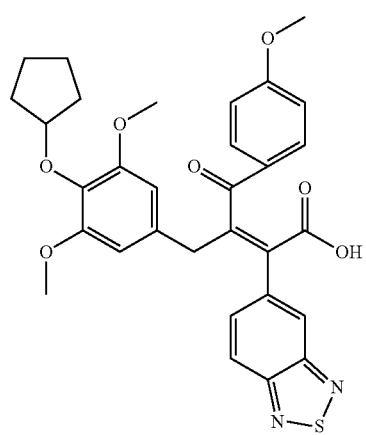
85
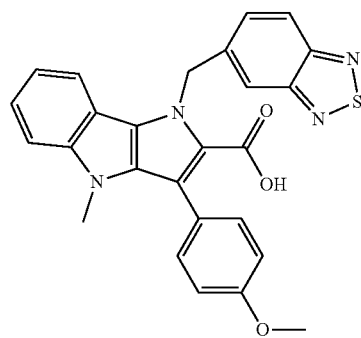
86
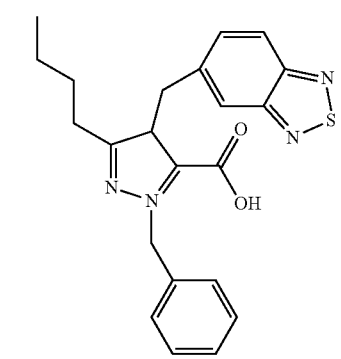
87
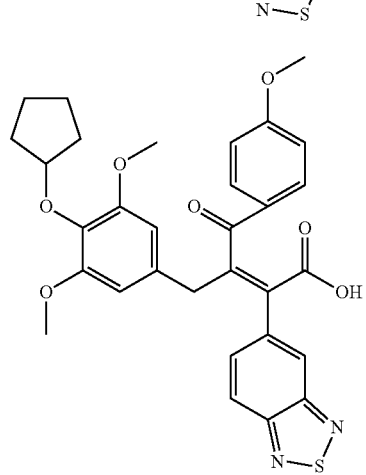
88
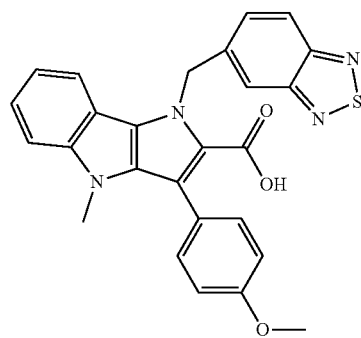
89
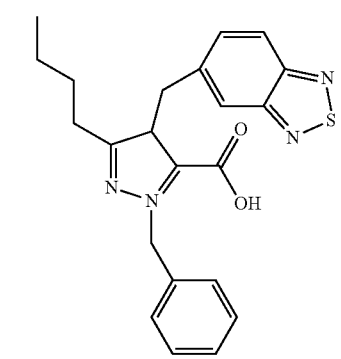
90
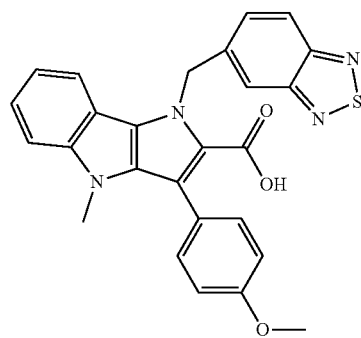
91
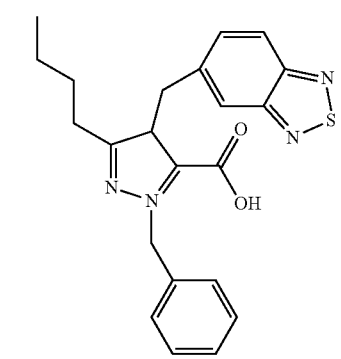

92 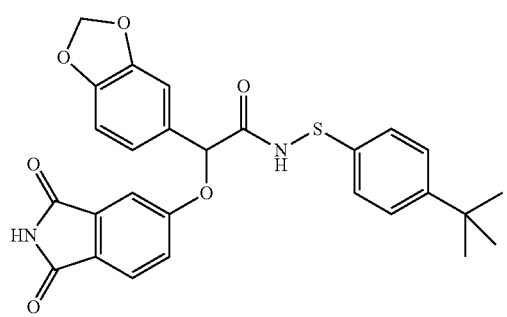
93 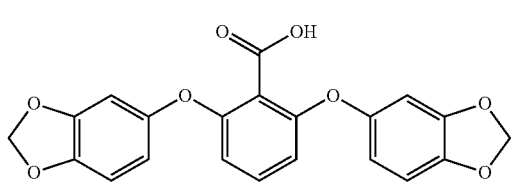
94 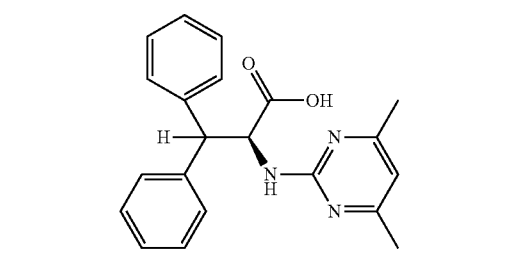
95 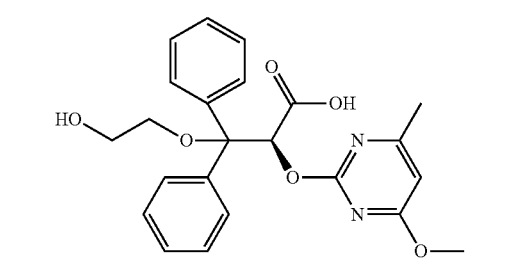
96 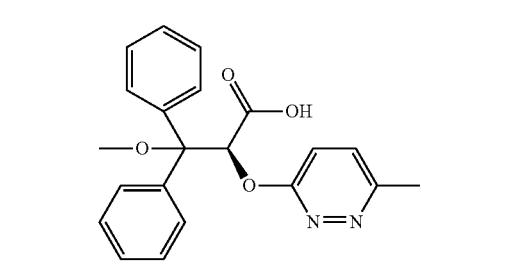
97 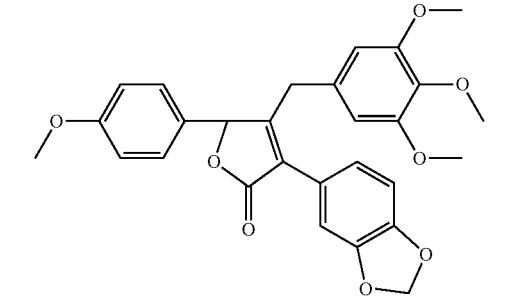
98 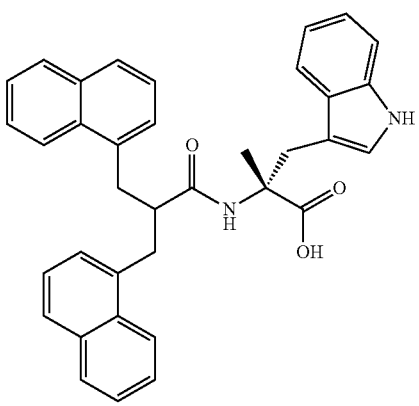
99 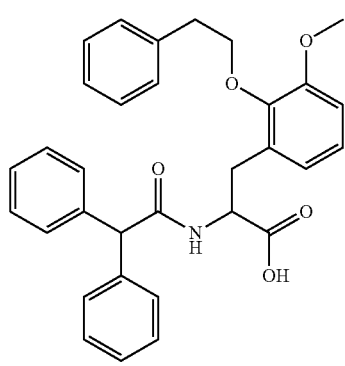
100 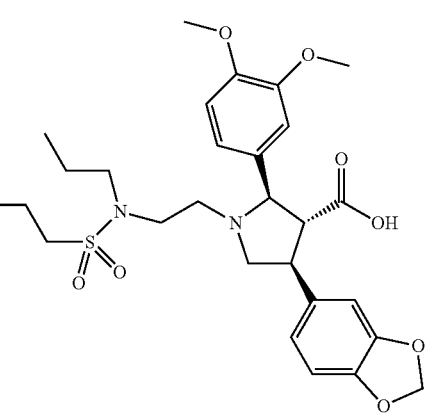
101 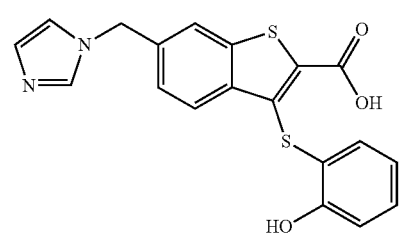

102

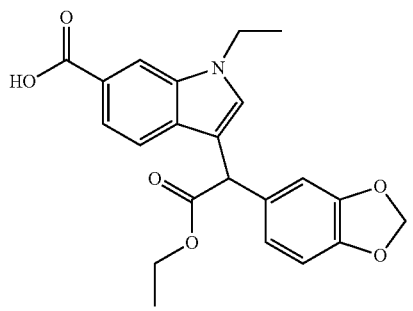

103

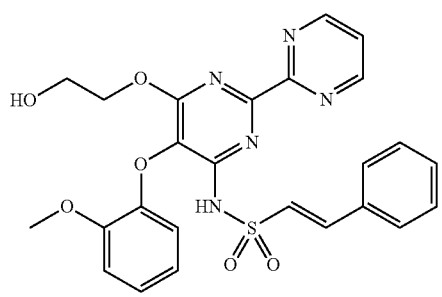

104

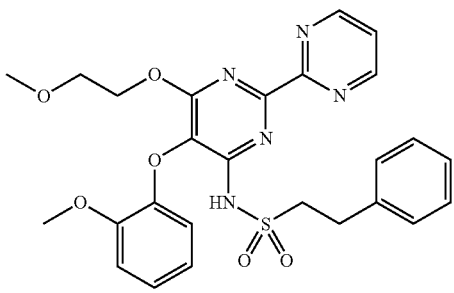

105

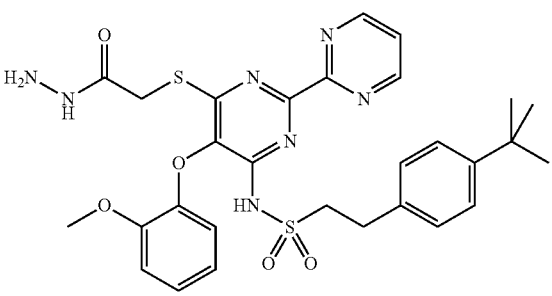

106

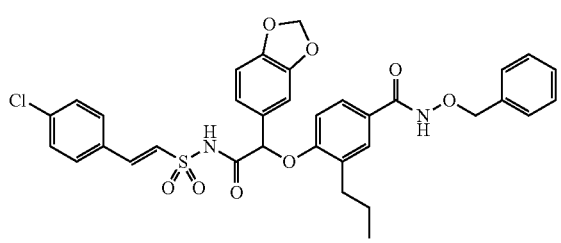

107

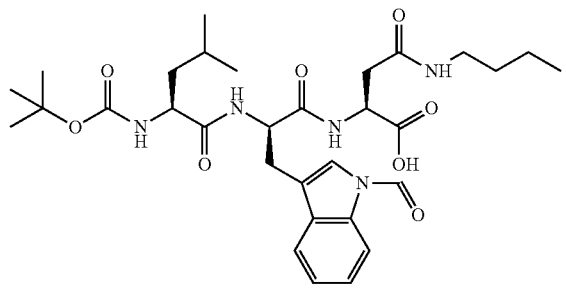

108

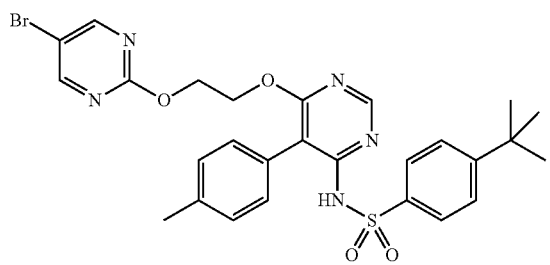

109

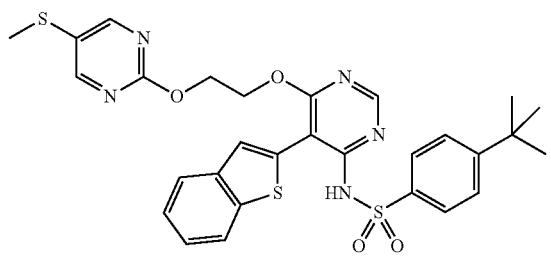

APPENDIX B

Balanced $Et_A/Et_B$ Antagonists

APPENDIX C

Selective $Et_B$ Antagonists

APPENDIX D

Miscellaneous ET Antagonists

Modifications and variations of the invention as hereinbefore set forth can be made without departing from the spirit and scope thereof, and, therefore, only such limitations should be imposed as are indicated by the appended claims.

What is claimed is:

1. A method of treating hemorrhagic shock or shock due to circulatory failure comprising administering Ringer's lactate and a therapeutically effective amount of centhaquin to a mammal suffering from blood loss.

2. The method of claim 1 wherein the centhaquin is administered at a dose of about 0.05 to about 0.15 mg/kg.

3. The method of claim 1 wherein Ringer's lactate is administered in a volume amount of up to 100% of a volume amount of blood loss (LR-100).

4. The method of claim 1 wherein Ringer's lactate is administered in a volume amount of up to 300% of a volume amount of blood loss (LR-300).

5. The method of claim 1 wherein the centhaquin is administered by parenteral administration.

6. The method of claim 5 wherein the parenteral administration is intravenous administration.

7. The method of claim 1 wherein the centhaquin is administered at a dose of about 0.05 mg/kg.

8. The method of claim 1 wherein the centhaquin is administered in a dose range from 10 μg to about 300 μg.

9. The method of claim 1 wherein the centhaquin is administered at a dose of about 0.05 to about 0.45 mg/kg.

10. The method of claim 1 wherein the mammal is a human.

\* \* \* \* \*